United States Patent
Church et al.

(10) Patent No.: US 11,359,211 B2
(45) Date of Patent: *Jun. 14, 2022

(54) RNA-GUIDED HUMAN GENOME ENGINEERING

(71) Applicant: President and Fellows of Harvard College, Cambridge, MA (US)

(72) Inventors: George M. Church, Brookline, MA (US); Prashant G. Mali, La Jolla, CA (US); Luhan Yang, Somerville, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/397,423

(22) Filed: Apr. 29, 2019

(65) Prior Publication Data

US 2019/0249194 A1 Aug. 15, 2019

Related U.S. Application Data

(63) Continuation of application No. 14/790,147, filed on Jul. 2, 2015, now Pat. No. 10,273,501, which is a continuation of application No. 14/653,144, filed as application No. PCT/US2013/075317 on Dec. 16, 2013, now Pat. No. 9,970,024.

(60) Provisional application No. 61/779,169, filed on Mar. 13, 2013, provisional application No. 61/738,355, filed on Dec. 17, 2012.

(51) Int. Cl.

| | |
|---|---|
| *C12N 15/00* | (2006.01) |
| *C12N 15/85* | (2006.01) |
| *C12N 15/10* | (2006.01) |
| *C12N 15/63* | (2006.01) |
| *C12N 15/90* | (2006.01) |
| *C12N 15/01* | (2006.01) |
| *C12N 15/81* | (2006.01) |
| *C12N 15/82* | (2006.01) |
| *C12N 15/87* | (2006.01) |
| *C12N 9/22* | (2006.01) |

(52) U.S. Cl.
CPC ............ *C12N 15/85* (2013.01); *C12N 9/22* (2013.01); *C12N 15/01* (2013.01); *C12N 15/10* (2013.01); *C12N 15/102* (2013.01); *C12N 15/1024* (2013.01); *C12N 15/63* (2013.01); *C12N 15/81* (2013.01); *C12N 15/8201* (2013.01); *C12N 15/87* (2013.01); *C12N 15/90* (2013.01); *C12N 15/907* (2013.01); *C12N 2310/20* (2017.05); *C12N 2800/80* (2013.01); *C12N 2810/55* (2013.01); *C12Y 301/00* (2013.01)

(58) Field of Classification Search
CPC .......... C12N 15/85; C12N 9/22; C12N 15/01; C12N 15/10; C12N 15/102; C12N 15/1024; C12N 15/63; C12N 15/81; C12N 15/8201; C12N 15/87; C12N 15/90; C12N 15/907; C12N 2310/20; C12N 2800/80; C12N 2810/55; C12Y 301/00

See application file for complete search history.

(56) References Cited

U.S. PATENT DOCUMENTS

| | | |
|---|---|---|
| 6,534,261 B1 | 3/2003 | Cox, III et al. |
| 6,586,240 B1 | 7/2003 | Singer et al. |
| 8,697,359 B1 | 4/2014 | Zhang |
| 8,795,965 B2 | 8/2014 | Zhang |
| 8,871,445 B2 | 10/2014 | Cong et al. |
| 8,889,394 B2 | 11/2014 | Chalasani |
| 8,906,616 B2 | 12/2014 | Zhang et al. |
| 8,932,814 B2 | 1/2015 | Cong et al. |
| 8,993,233 B2 | 3/2015 | Zhang et al. |
| 8,999,641 B2 | 4/2015 | Zhang et al. |
| 9,023,649 B2 | 5/2015 | Mali et al. |
| 9,267,135 B2 | 2/2016 | Church et al. |
| 10,435,708 B2 | 10/2019 | Mali et al. |
| 10,526,618 B2 | 1/2020 | Esvelt et al. |
| 10,851,380 B2 | 12/2020 | Kim et al. |
| 2003/0149254 A1 | 8/2003 | Anderson et al. |
| 2005/0220796 A1† | 10/2005 | Dynan |
| 2010/0076057 A1 | 3/2010 | Sontheimer et al. |
| 2010/0093617 A1 | 4/2010 | Barrangou et al. |
| 2011/0059502 A1 | 3/2011 | Chalasani |

(Continued)

FOREIGN PATENT DOCUMENTS

| | | |
|---|---|---|
| CA | 2534296 C | 3/2013 |
| JP | 2007501626 A | 2/2007 |
| JP | 2009-136298 A | 6/2009 |
| JP | 2011-207893 A | 10/2011 |
| JP | 2016-500003 A | 1/2016 |

(Continued)

OTHER PUBLICATIONS

Brouns et al (Science vol. 337, published Aug. 17, 2012, pp. 808-809; IDS reference) (Year: 2012).*

(Continued)

*Primary Examiner* — Catherine S Hibbert
(74) *Attorney, Agent, or Firm* — Banner & Witcoff, Ltd.

(57) ABSTRACT

A method of altering a eukaryotic cell is provided including transfecting the eukaryotic cell with a nucleic acid encoding RNA complementary to genomic DNA of the eukaryotic cell, transfecting the eukaryotic cell with a nucleic acid encoding an enzyme that interacts with the RNA and cleaves the genomic DNA in a site specific manner, wherein the cell expresses the RNA and the enzyme, the RNA binds to complementary genomic DNA and the enzyme cleaves the genomic DNA in a site specific manner.

68 Claims, 42 Drawing Sheets
(38 of 42 Drawing Sheet(s) Filed in Color)
Specification includes a Sequence Listing.

(56) References Cited

U.S. PATENT DOCUMENTS

| | | |
|---|---|---|
| 2011/0189776 A1 | 8/2011 | Terns et al. |
| 2011/0223638 A1 | 9/2011 | Wiedenheft et al. |
| 2011/0301073 A1 | 12/2011 | Gregory et al. |
| 2012/0060230 A1 | 3/2012 | Collingwood et al. |
| 2013/0130248 A1 | 5/2013 | Haurwitz et al. |
| 2013/0253040 A1 | 9/2013 | Miller et al. |
| 2014/0068797 A1* | 3/2014 | Doudna .................. C12N 9/22 800/18 |
| 2014/0179006 A1 | 6/2014 | Zhang |
| 2014/0179770 A1 | 6/2014 | Zhang et al. |
| 2014/0242699 A1 | 8/2014 | Zhang |
| 2014/0256046 A1* | 9/2014 | Zhang ..................... C12N 9/22 435/455 |
| 2014/0310830 A1 | 10/2014 | Zhang et al. |
| 2014/0315985 A1 | 10/2014 | May et al. |
| 2014/0335620 A1 | 11/2014 | Zhang et al. |
| 2014/0342456 A1 | 11/2014 | Mali et al. |
| 2015/0031132 A1 | 1/2015 | Church et al. |
| 2015/0031133 A1 | 1/2015 | Church et al. |
| 2015/0166969 A1 | 6/2015 | Takeuchi et al. |
| 2015/0232833 A1 | 8/2015 | Mali et al. |
| 2015/0247150 A1 | 9/2015 | Zhang et al. |
| 2015/0259704 A1 | 9/2015 | Church et al. |
| 2015/0284727 A1 | 10/2015 | Kim et al. |
| 2015/0291965 A1 | 10/2015 | Zhang et al. |
| 2015/0322457 A1* | 11/2015 | Kim ....................... C12N 15/52 435/462 |
| 2016/0002670 A1 | 1/2016 | Church et al. |
| 2016/0017366 A1 | 1/2016 | Chen et al. |
| 2016/0153006 A1 | 6/2016 | Zhang et al. |
| 2016/0160210 A1 | 6/2016 | Mali et al. |
| 2016/0237456 A1 | 8/2016 | Church et al. |
| 2016/0298134 A1* | 10/2016 | Chen .............. C12Y 301/21004 |
| 2016/0340662 A1 | 11/2016 | Zhang et al. |
| 2016/0355795 A1 | 12/2016 | Ran et al. |
| 2017/0191078 A1 | 7/2017 | Zhang et al. |
| 2017/0191082 A1 | 7/2017 | Chen et al. |
| 2020/0277631 A1 | 9/2020 | Doudna et al. |

FOREIGN PATENT DOCUMENTS

| | | | |
|---|---|---|---|
| JP | 2016-502840 | A | 2/2016 |
| JP | 2016-504026 | A | 2/2016 |
| WO | 2008/108989 | A2 | 9/2008 |
| WO | 2010/054108 | A2 | 5/2010 |
| WO | 2011/143124 | A2 | 11/2011 |
| WO | 2011/146121 | A1 | 11/2011 |
| WO | 2012/164565 | A1 | 12/2012 |
| WO | 2013/098244 | A1 | 7/2013 |
| WO | 2013/126794 | A1 | 8/2013 |
| WO | 2013/141680 | A1 | 9/2013 |
| WO | 2013/142578 | A1 | 9/2013 |
| WO | 2013/176772 | A1 | 11/2013 |
| WO | 2014/022702 | A2 | 2/2014 |
| WO | 2014/065596 | A1 | 5/2014 |
| WO | 2014/089290 | A1 | 6/2014 |
| WO | 2014/093595 | A1 | 6/2014 |
| WO | 2014/093622 | A2 | 6/2014 |
| WO | 2014/093655 | A2 | 6/2014 |
| WO | 2014/093712 | A1 | 6/2014 |
| WO | 2014/099744 | A1 | 6/2014 |
| WO | 2014093718 | A1 | 6/2014 |

OTHER PUBLICATIONS

Kalderon et al entitled "A short amino acid sequence able to specify nuclear location" (Cell vol. 39, No. 3, part 2, Dec. 1984: pp. 499-509; abstract only). (Year: 1984).*

Al-Attar et al., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.

Baker, M., "Gene editing at CRISPR speed," Nature Biotechnology, 2014, vol. 32(4), pp. 309-312.

Bassett, A.R. and Liu, J.-L., "CRISPR/Cas9 and Genome Editing in Drosophila," Journal of Genetics and Genomics, 2014, vol. 41, pp. 7-19 (including supplementary materials).

Caroll, Dana, "Zinc-finger Nucleases as Gene Therapy Agents", Gene Ther., 2008, vol. 15, No. 22, pp. 1463-1468.

Carroll, "A CRISPR Approach to Gene Targeting" 20(9) Molecular Therapy 1658-1660 (Sep. 2012).

Cong, Le et al., Multiplex Genome Engineering Using CRISPR/Cas Systems, Science vol. 339, Issue 6121, pp. 819-823, Feb. 15, 2013.

Formal observations under Art. 115 EPC for European Patent Application No. 13863815.0 issued Feb. 26, 2019.

Formal observations under Art. 115 EPC for European Patent Application No. 13863815.0 issued Sep. 4, 2018.

Gaj, Thomas et al. , "Targeted gene knockout by direct delivery of zinc-finger nuclease proteins", Nature Methods, Aug. 2012, vol. 9, pp. 805-809.

Gasiunas, G et al Cas9-crRNA Ribonucleoprotein Complex Mediates Specific DNA Cleavage for Adaptive Immunity in Bacteria. PNAS. Sep. 4, 2012. vol. 109, No. 39; pp. E2579-E2586; p. E2583, first column, first paragraph. DOI: 1 0.1073/pnas.1208507109.

Gilbert, et al. "CRISPR-Mediated Modular RNA-Guided Regulation of Transcription in Eukaryotes", Cell, Jul. 18, 2013. vol. 154 No. 2, pp. 442-451, Elsevier, Inc.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.

International Search Report issued in corresponding PCT/US2013/075317, dated Apr. 15, 2014.

International Search Report issued in corresponding PCT/US2013/075326, dated Aug. 22, 2014.

Jinek, et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. entire document.

Jinek, M. et al. "A Programmable Dual-RNA-Guided DNA Endonuclease in Adaptive Bacterial Immunity," Science. Aug. 17, 2012. vol. 337; pp. 816-821.

Le Rhun, Anais et al., "Small RNAs in streptococci," RNA Biology, Apr. 2012, vol. 9, pp. 414-426.

Lee, Ciaran M., et al., "Correction of the DF508 Mutation in the Cystic Fibrosis Transmembrane Conductance Regulator Gene by Zinc-Finger Nuclease Homology-Directed Repair", BioResearch Open Access?Jun. 2012, vol. 1, pp. 99-108.

Letter of Payam Moradian dated Apr. 6, 2015.

Li, T. et al., "Modularly Assembled Designer TAL Effector Nucleases for Targeted Gene Knockout and Gene Replacement in Eukaryotes," Nucleic Acids Research, 2011, vol. 39(14), pp. 6315-6325.

Makarova et al., "Evolution and classification of the CRISPR-Cas systems" 9(6) Nature Reviews Microbiology 467-477 (1-23) (Jun. 2011).

Mali, Prashant et al., "RNA-Guided Human Genome Engineering via Cas9", Science, Feb. 15, 2013, vol. 339, pp. 823-826.

Mali, P. et al., "Cas9 as a Versatile Tool for Engineering Biology," Nature Methods, 2013, vol. 10 (1 0), pp. 957-963.

Miller, Jeffrey C. et al., "A TALE nuclease architecture for efficient genome editing", Nature Biotechnology, 2011, vol. 29, No. 2, pp. 143-148.

Observations under Art.115 EPC issued for EP 13863815.0, dated Feb. 21, 2019.

Office Action issued in U.S. Appl. No. 14/319,380 dated Jan. 28, 2015.

Office Action issued in U.S. Appl. No. 14/319,530, dated Apr. 1, 2015.

Porteus, Matthew H. et al., "Chimeric Nucleases Stimulate Gene Targeting in Human Cells", Science, 2003, vol. 300, p. 763.

(56) References Cited

OTHER PUBLICATIONS

Qi, L. et al., "RNA Processing Enables Predictable Programming of Gene Expression," Nature Biotechnology, 2012, vol. 30(1 0), pp. 1002-1007 (including Supplementary Information).
Raymond, C.S. and Soriano, P., "High-Efficiency FLP and PhiC31 Site-Specific Recombination in Mammalian Cells," PLoS One, 2007, vol. 2(1), p. e162.
Regalado, A., "Who Owns the Biggest Biotech Discovery of the Century?," MIT Technology 2 Review, Dec. 4, 2014, http://www.technologyreview.com/featuredstory/532796/who-owns-the-biggest-biotech-di scovery-of-the-century.
Rho, Mina et al. 'Diverse CRISPRs Evolving in Human Microbiomes.' PLoS Genetics. vol. 8, No. 6. 1-14 pp. 1-12. Jun. 2012. entire document.
Shanks, P., "CRISPR Opportunities . . . For What? And For Whom?," Biopolitical Times, Dec. 4, 2014, http://www.biopoliticaltimes.org/article.php?id=8235.
Sontheimer Erik, Project 7: Establishing RNA-Directed DNA Targeting in Eukaryotic Cells; Project dates: Nov. 16, 2011 to Dec. 31, 2012 (Feb. 4, 2012).
Sylwia Bobis-Wozowicz, Anna Osiak et al., "Targeted genome editing in pluripotent stem cells using zinc-finger nucleases", Methods, 2011, vol. 53, pp. 339-346.
Transmittal of third party observations & third party observations issued for European Patent Application No. 13863815.0 on Feb. 21, 2019.
Transmittal of third party observations and third party observations issued for European Patent Application No. 13863815.0 on Feb. 26, 2019.
Transmittal of third party observations issued for European Patent Application No. 13863815.0 on Sep. 4, 2018.
U.S. Appl. No. 61/652,086, filed May 25, 2012—Jinek et al.
U.S. Appl. No. 61/734,256, filed Dec. 6, 2012—Chen, F. et al.
U.S. Appl. No. 61/736,527, filed Dec. 12, 2012—Zhang et al.
Wiedenheft eta!., "RNA-guided genetic silencing systems in bacteria and archaea" 482 Nature 331-338 (Feb. 16, 2012).
Rebar, E.J. et al. "Induction of angiogenesis in a mouse model using engineered transcription factors." Nature Medicine. 8: 1427-1432 (2002).
Perez-Pinera, P. "Advances in Targeted Genome Editing." Current Opinion in Chemical Biology, 16 (3-4), 268-277 (2012).
Hwang, W. et al. "Efficient genome editing in zebrafish using a CRISPR-Cas system." Nature Biotechnology 31, 227-229 (2013), and Supplementary Materials.
Campeau, E. et al. "A versatile viral system for expression and depletion of proteins in mammalian cells." PLoS ONE 4, e6529 (2009).
Radulovich, N. et al. "Modified gateway system for double shRNA expression and Cre/lox based gene expression." BMC Biotech. 11, 1-9 (2011).
The ABCs of Gene Cloning, 93-124 (2005).
Gene Transfer and Expression in Mammalian Cells, Table 1 (2003).
Handel, E. et al. Versatile and efficient genome editing in human cells by combining zinc-finger nucleases with adeno-associated viral vectors. Human Gene Ther. 23:321-329 (2012).
Urnov, F. et al. "Genome editing with engineered zinc finer nucleases." Nat. Rev. Gene. 11, 636-646 (2010).
Zhang, F. et al. "Programmable Sequence-Specific Transcriptional Regulation of Mammalian Genome Using Designer TAL Effectors." Nature Biotechnol. vol. 29(2): 149-153 (2011).
Sanjana, N. et al. "A Transcription Activator-Like Effector (TALE) Toolbox for Genome Engineering." Nat. Proto. vol. 7(1):171-192 (2011).
Cong, L. et al. "Comprehensive Interrogation of Natural TALE DNA Binding Modules and Transcriptional Repressor Domains." Nature Commun. 3:968 (2012).
Dominguez, A. et al. "Beyond editing: repurposing CRISPR-Cas9 for precision genome regulation and interrogation." Nat. Rev. Mol. Cell Biol. 17(1): 5-15 (2016).

"Lipofectamine 2000 Transfection Reagent" (ThermoFisher Scientific website).
Molecular Biology of the Cell, Fifth Ed., 699-707 (2008).
Cermak, T. et al. "Efficient design and assemly of custom TALEN and other TAL effector-based constructs for DNA targeting." Nucleic Acids Research. vol. 39, No. 12 e82 (2011).
Kuzmine, I. et al. "Binding of the priming nucleotide in the initiation of transcription by T7 RNA polymerase." J. Biol. Chem. 278(5): 2819-2823 (2003).
Brouns, S. "A Swiss Army Knife of Immunity." Science, vol. 337, 808-809 (2012).
Christian, M. et al. "Targeting DNA Double-Strand Breaks with TAL Effector Nucleases," Genetics, vol. 186, pp. 757-761 (2010).
"Transcription activator-like effector nuclease," Wikipedia, Nov. 16, 2012.
Le Provost, F. et al, "Zinc finger nuclease technology heralds a new era in mammalian transgenesis," Trends in Biotechnology, vol. 28(3), pp. 134-141 (2009).
Singer, O. et al., "Applications of Lentiviral Vectors for shRNA Delivery and Transgenesis," Curr. Gene Ther., vol. 8(6), pp. 483-488 (2008).
Cho, S. et al., "Targeted genome engineering in human cells with the Cas9 RNA-guided endonuclease," Nature Biotechnol., vol. 31(3), pp. 230-232 (2013), plus Supplementary Materials.
Barrangou, R. "RNA-mediated programmable DNA cleavage." Nat. Biotechnol., vol. 30(9), pp. 836-838 (2012).
Declaration and Curriculum Vitae of Dr. Gang Bao.
Hockemeyer, D. et al. "Gene Targeting in Human Pluripotent Cells." Cold Spring Harbor Symposia for Quantitative Biology, vol. 75, pp. 201-209 (2010).
Gantz, J. et al. "Targeted Genomic Integration of a Selectable Floxed Dual Fluorescence Reporter in Human Embryonic Stem Cells." PLOS One, vol. 7(10):e46971 (2012).
Lewin, B. et al, Cells, p. 224 (2007).
CNLS Mapper Report for *S. pyogenes* Cas9.
Hu, P. et al, "Comparison of Various Nuclear Localization Signal-Fused Cas9 Proteins and Cas9 mRNA for Genome Editing in Zebrafish." G3, vol. 8, pp. 823-831 (2018).
Schultz, J. et al, "Development of a CRISPR/Cas9 system for high efficiency multiplexed gene deletion in Rhodosporidium toruloides." Biotechnology and Bioengineering, vol. 116, pp. 2103-2109 (2019).
Gustafsson, C. et al., "Codon bias and heterologous protein expression." Trends Biotech., vol. 22(7), pp. 346-353 (2004).
Joung, J. et al., "TALENs: a widely applicable technology for targeted genome editing." Nat. Rev. Mol. Cell Biol., vol. 14, pp. 49-55 (2013).
Chang, N. et al, "Genome editing with RNA-guided Cas9 nuclease in Zebrafish embryos." Call Research, vol. 23, pp. 465-472 (2013).
Gratz, S. et al., "Genome engineering of *Drosophila* with the CRISPR RNA-guided Cas9 nuclease," Genetics, vol. 194, pp. 1029-1035, plus Supplementary Material (2013).
Notice of Opposition filed Oct. 24, 2019 against EP 2825654, and Preliminary Opinion of the Opposition Division.
Deltcheva, E. et al., "CRISPR RNA maturation by trans-encoded small RNA and host factor RNase III," Nature, vol. 471(7340), pp. 602-607 (doi:10.1038/nature09886), plus Supplementary Material (2011).
Raymond, C. et al., "High-Efficiency FLP and phiC31 Site-Specific Recombination in Mammalian Cells," PLoS ONE, vol. 1 (e162), pp. 1-4 (2007).
PHcRed1 Vector Information Sheet, Clontech Laboratories, Inc. (2003).
Lyssenko, N. et al., "Cognate putative nuclear localization signal effects strong nuclear localization of a GFP reported and facilitates gene expression studies in Caenhoghabditis elegans," Biotechniques, vol. 43, pp. 596-600 (2007).
PShooter Vector User Guide, Invitrogen (2012).
Fischer-Fantuzzi, L. et al., "Cell-Dependent Efficiency of Reiterated Nuclear Signals in a Mutant Simian Virus 40 Oncoprotein Targeted to the Nucleus," Molecular and Cellular Biology, vol. 8(12), pp. 5495-5503 (1988).

(56) References Cited

OTHER PUBLICATIONS

Kim, E. et al., "Precision genome engineering with programmable DNA-nicking enzymes," Genome Res., vol. 22, pp. 1327-1333 (2012).
Chen, C. et al., "Transfection and expression of plasmid DNA in plant cells by an arginine-rich intracellular delivery peptide without protoplast preparation," FEBS Letters, vol. 581, pp. 1891-1897 (2007).
Maraia, R. et al., "3' processing of eukaryotic precursor tRNAs," Wiley Interdiscip Rev RNA, vol. 2 (3), pp. 362-375 (2010).
Gao, Z. et al., "Delineation of the Exact Transcription Termination Signal for Type 3 Polymerase III," Molecular Therapy—Nucleic Acids, vol. 10, pp. 36-44, plus Supplementary Material (2018).
Kalderon, D. et al., "A Short Amino Acid Sequence Able to Specify Nuclear Location," Cell, vol. 39, pp. 499-509 (1984).
Tuschl, T., "Expanding small RNA interference," Nature Biotechnology, vol. 20, pp. 446-448 (2002).
Carroll, D. et al., "Design, construction and in vitro testing of zinc finger nucleases." Nature Protocols, vol. 1(3), pp. 1329-1341 (2006).
Liu, P. et al., "Generation of a Triple-Gene Knockout Mammalian Cell Line Using Engineered Zinc-Finger Nucleases." Biotechnol Bioeng., vol. 106(1), pp. 97-105 (2010).
Lee, H. et al., "Targeted chromosomal deletions in human cells using zinc finger nucleases." Genome Res., vol. 20, pp. 81-89 (2010).
Brunet, E. et al., "Chromosomal translocations induced at specified loci in human stem cells." PNAS, vol. 106(26), pp. 10620-10625 (2009).
Carlson, D. et al., "Targeting DNA With Fingers and TALENs." Molecular Therapy—Nucleic Acids, vol. 1(e3), pp. 1-4 (2012).
Handel, E. et al., "Versatile and Efficient Genome Editing in Human Cells by Combining Zinc-Finger Nucleases With Adeno-Associated Viral Vectors," Human Gene Ther., vol. 23(2), pp. 321-329 (2012).
Li, T. et al., "TAL nucleases (TALNs): hybrid proteins composed of TAL effectors and FokI DNA-cleavage domain." Nucleic Adic Res., vol. 39(12), pp. 359-372 (2010).
Ma, S. et al., "Highly Efficient and Specific Genome Editing in Silkworm Using Costom TALENs." PLoS ONE, vol. 7(9), e45035 (2012).
Reiss, B. et al., "RecA protein stimulates homologous recombination in plants." PNAS, vol. 93, pp. 3094-3098 (1996).
Sauer, B. et al., "Site-specific DNA recombination in mammalian cells by the Cre recombinase of bacteriophage P1." Proc. Natl. Acad. Sci. USA, vol. 85(14), pp. 5166-5170 (1988).
Groth, A. et al., "A phage integrase directs efficient site-specific integration in human cells," Proc. Natl. Acad. Sci. USA, vol. 97(11), pp. 5995-6000 (2000).
Chapdelaine, P. et al., "Meganucleases can restore the reading frame of a mutated dystrophin." Gene Therapy, vol. 17, pp. 846-858 (2010).
Mastroianni, M. et al., "Group II Intron-Based Gene Targeting Reactions in Eukaryotes." PLoS ONE, vol. 3(9), e3121 (2008).
Morgan, W. et al., "Inducible Expression and Cytogenetic Effects of the EcoRI Restriction Endonuclease in Chinese Hanster Ovary Cells." Molecular and Cellular Biology, vol. 8(10), pp. 4204-4211 (1988).
Carney, J. et al., "Induction of DNA Double-Strand Breaks by Electrocorporation of Restriction Enzymes into Mammalian Cells." Methods in Mol. Biol., vol. 113, pp. 465-471 (1999).
Schiestl, R. et al., "Integration of DNA fragments by illegitimate recombination in *Saccharomyces cerevisiae*." Proc. Natl. Acad. Sci. USA, vol. 88(17), pp. 7585-7589 (1991).
Kuspa, A. et al., "Tagging developmental genes in Dictyostelium by restriction enzyme-mediated integration of plasmid DNA." Proc. Natl. Acad. Sci. USA, vol. 89(18), pp. 8803-8807 (1992).
Gopalan, V. et al., "RNase P: Variations and Uses*." The Journal of Biological Chemistry, vol. 277(9), pp. 6759-6762 (2002).
Link, K. et al., "Engineering ligand-responsive gene-control elements: lessons learned from natural riboswitches." Gene Therapy, vol. 16(10), pp. 1189-1201 (2009).
Wieland, M. et al., "Engineering of ribozyme-based riboswitches for mammalian cells." Methods, vol. 56., pp. 351-357 (2012).
Fieck, A. et al., "Modifications of the *E. coli* Lac repressor for expression in eukaryotic cells: effects of nuclear signal squences on protein activity and nuclear accumulation." Nucleic Acids Res., vol. 20(7), pp. 1785-1791 (1992).
Planey, S. et al., "Mechanisms of Signal Transduction: Inhibition of Glucocorticoid-induced Apoptosis in 697 Pre-B Lymphocytes by the Mineralocorticoid Receptor N-terminal Domain." J. Biol. Chem, vol. 277(44), pp. 42188-42196 (2002).
Lange, A. et al., "Classical Nuclear Localization Signals: Definition, Function, and Interaction with Importin a*s." J. Biol. Chem, vol. 282(8), pp. 5101-5105 (2007).
Notice of Opposition—James Poole Ltd., filed Nov. 4, 2019.
Notice of Opposition—Patent Boutique LLP, filed Feb. 14, 2020.
Notice of Opposition—Mathys & Squire LLP, filed Feb. 14, 2020.
Notice of Opposition—George Schlich, filed Feb. 17, 2020.
Lee, H. et al., "Targeted chromosomal duplications and inversions in the human genome using zinc finger nucleases." Genome Res., vol. 22, pp. 539-548 (2012).
Ramirez, C. et al., "Engineered zinc finger nickases induce homology-directed repair with reduced mutagenic effects." Nucleic Acid Res., vol. 40(12), pp. 5560-5568 (2012).
U.S. Appl. No. 61/835,931, filed Jun. 17, 2013—Zhang et al.
Gasiunas et al., "Cas9-crRNA ribonucleoprotein complex mediates specific DNA cleavage for adaptive immunity in bacteria" PNAS, Sep. 25, 2012, 109(39) E2579-E2586.
Office Action issued for Japanese Application No. 2018-230081 dated Oct. 29, 2019.
Liu et al., "Combinatorial RNAi Against HIV-1 Using Extended Short Hairpin RNAs," Molecular Therapy, vol. 17, No. 10, pp. 1712-1723 (2009).
Pougach et al., "CRISPR Adaptive Immunity Systems of Prokaryotes," Molecular Biology, vol. 46, No. 2, pp. 175-182 (2012).
Good et al., "Expression of small, therapeutic RNAs in human cell nuclei," Gene Ther. 4(1):45-54, (1997).†
Raymond et al., "High-Efficiency FLP and PhiC31 Site-Specific Recombination in Mammalian Cells," PLoS One 2(1):e162, (2007).†

\* cited by examiner
† cited by third party

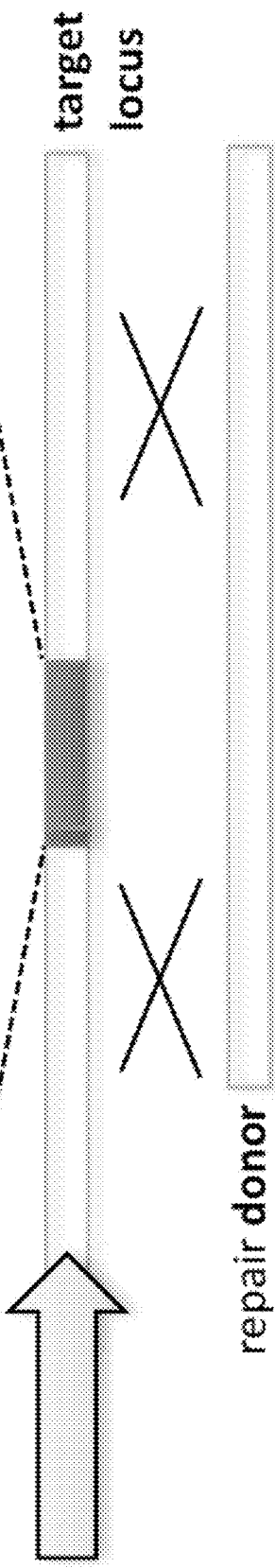
FIG. 1B
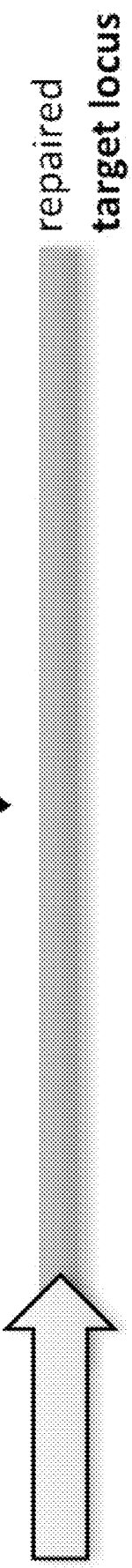
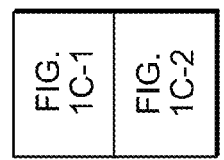
FIG. 1C

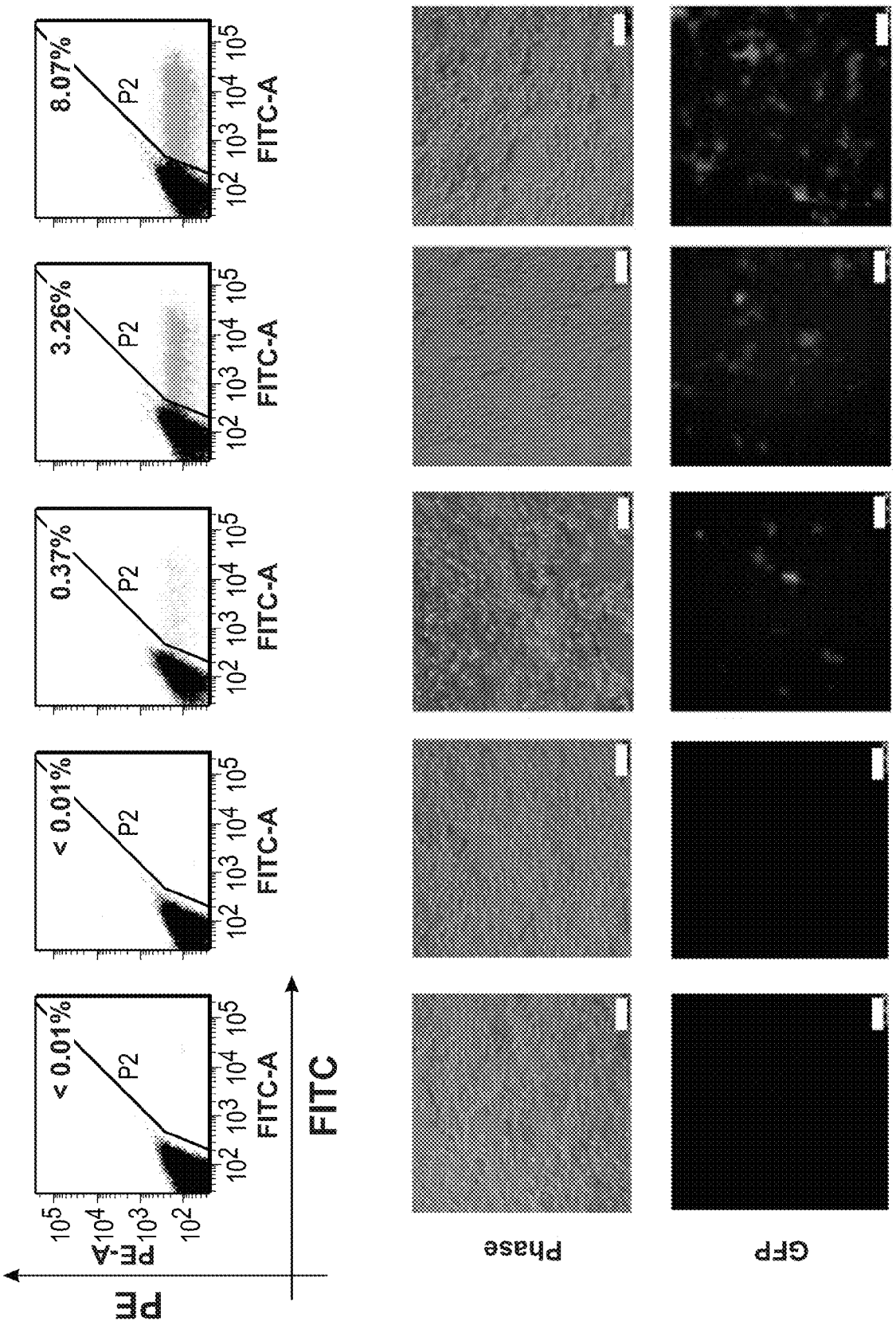

endogenous 'native' hAAVS1 locus sequence

..TTATCTGTCCCCTCCACCCCACACAGTGGGGCCACTAGGGACAGGATTGGTGA..

T1 target

T2 target

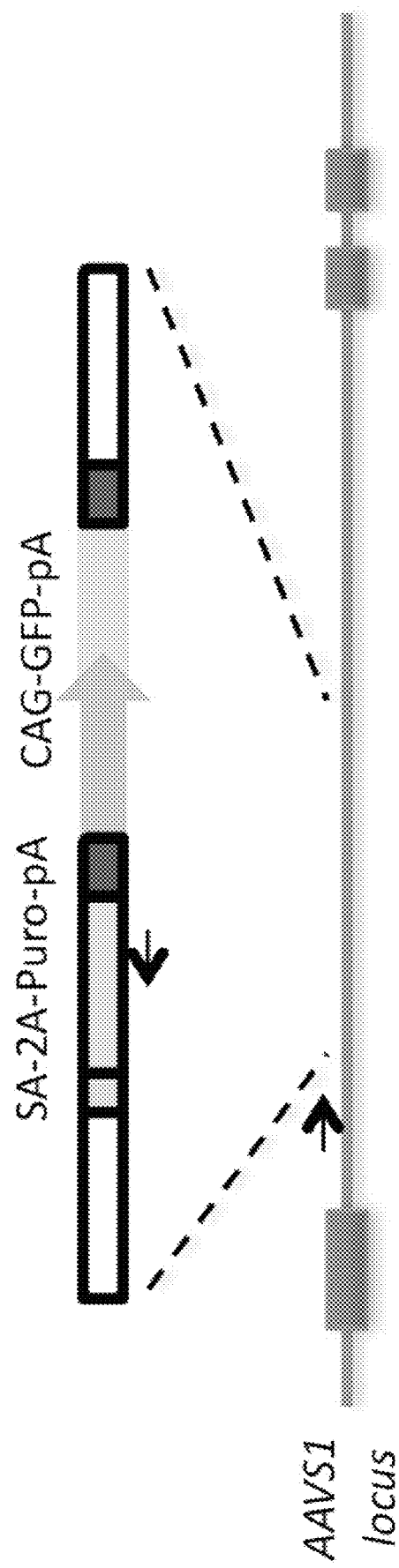

U6 promoter + target RNA + guide RNA scaffold:

TGTTACAAAAAGCAGGCTTTAAAGGAACCAATTCAGTCGACTGGATCCGGTACCAAGGTCTATATATTATTTG
CATATACGATACAAGGCTGTTAGAGAGATAATTGGAATTAATTTGACTGTAAACACAAAGATATTAGTACAAAATACG
CGGTAGTTTATCACAGTTAAATTGCTAACGCAGTCAGTGCTTCTGACACAACAGTCTCGAACTTAAGCTGCAGAAG
CACGTAGTTTGCAGTTTAAAATTATGTTTTAAAATGGACTATCATATGCTTACCGTAACTTGAAAGTATTTCGATTTCTTGGCTTT
ATATATCTTGTGGAAAGGACGAAACACCGNNNNNNNNNNNNNNNNNNNGTTTTAGAGCTAGAAATAGCAAGTTAAAATAAGGCTAGTCCGTTATCAACTTGAAAAAGTGGCACCGAGT
CGGTGCTTTTTTCTAGACCCAGCTTTCTTGTACAAAGTTGGCATTA

Guide RNA matches target sequence

5' – GNNNNNNNNNNNNNNNNNNNN gRNA scaffold

FIG. 3C

PAM general form of target sequence

GNNNNNNNNNNNNNNNNNNNNGG

| Name | Target Sequence |
|---|---|
| GFP gRNA Target 1 | GTGAACCGCATCGAGCTGAAGG |
| GFP gRNA Target 2 | GGAGCGCACCATCTTCTTCAAGG |
| AAVS1 gRNA Target 1 | GTCCCTCCACCCCACAGTGGGG |
| AAVS1 gRNA Target 2 | GGGGCCACTAGGGACAGGATTGG |
| DNMT3a gRNA Target 1 | GCATGATGCGCGGCCCAAGCAGG |
| DNMT3a gRNA Target 2 | GAGATGATGGCCCCTTCTCTGG |
| DNMT3b gRNA Target | GAATTACTCACGCCCAAGGAGG |

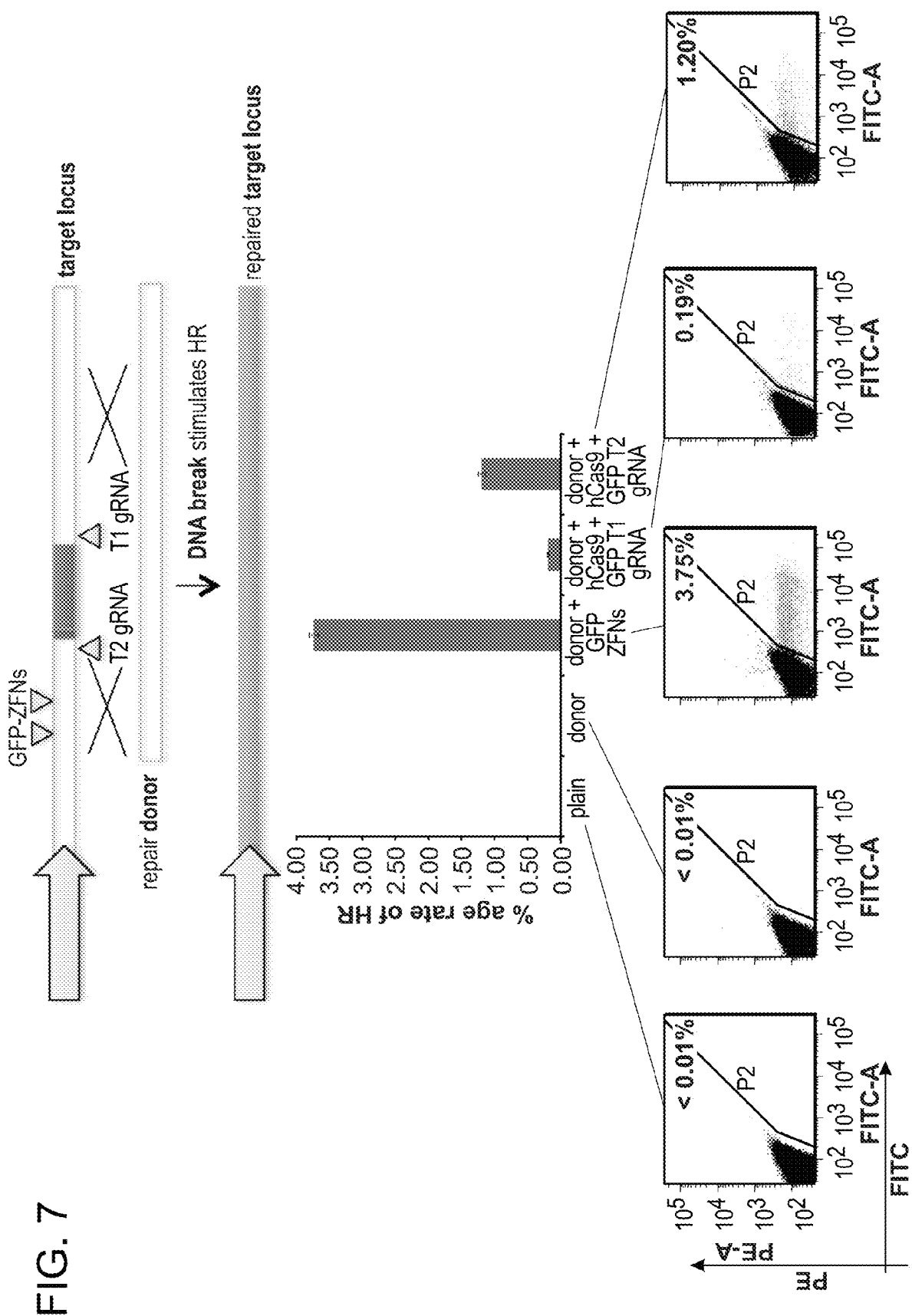

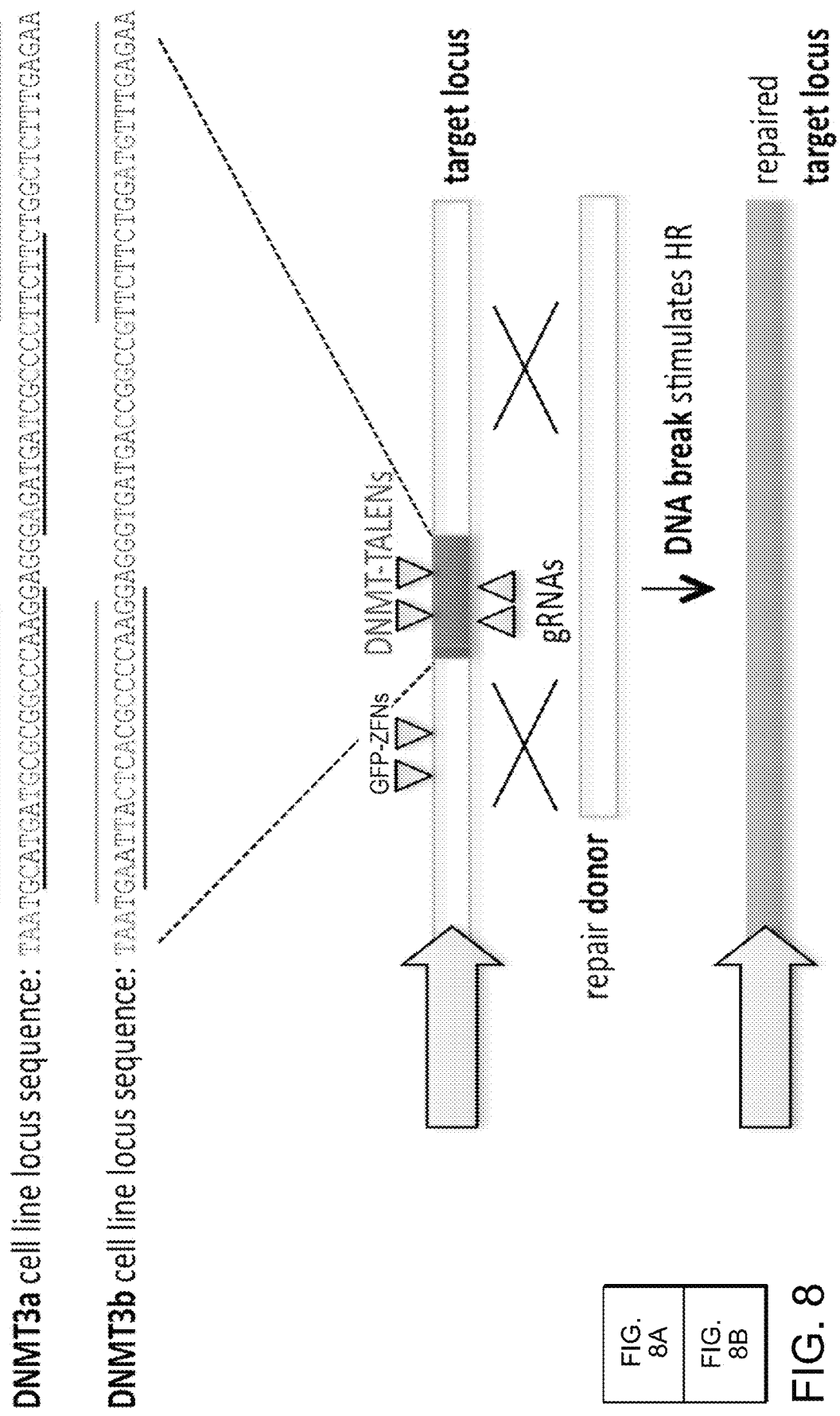

| FIG. 9A |
|---|
| FIG. 9B |
| FIG. 9C |

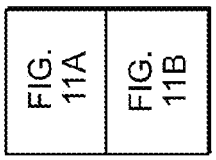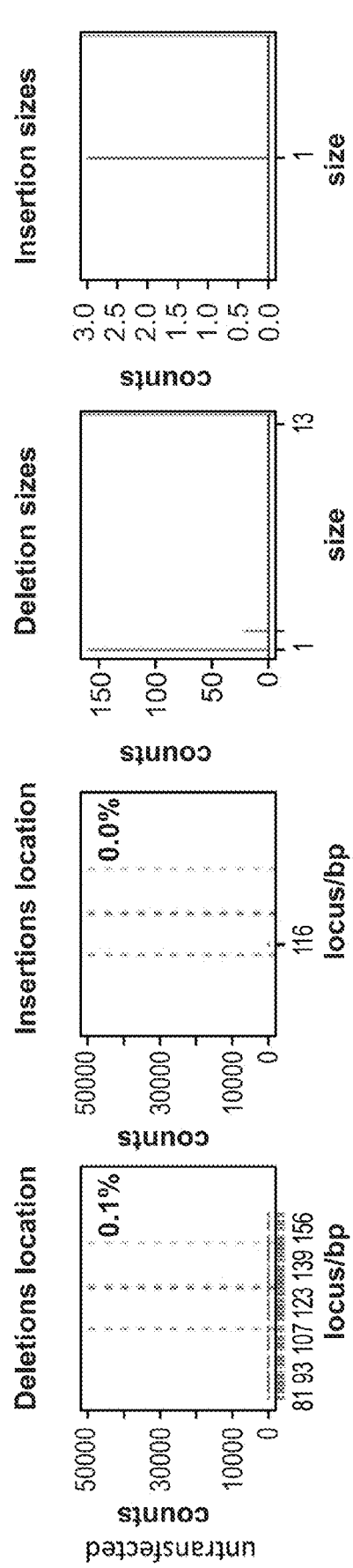
FIG. 11A

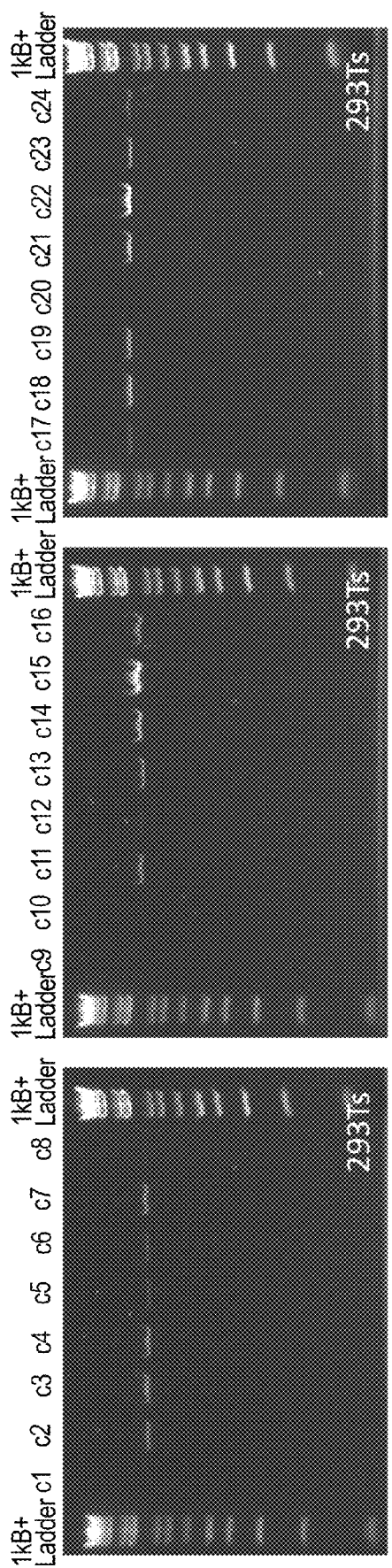
FIG. 12A
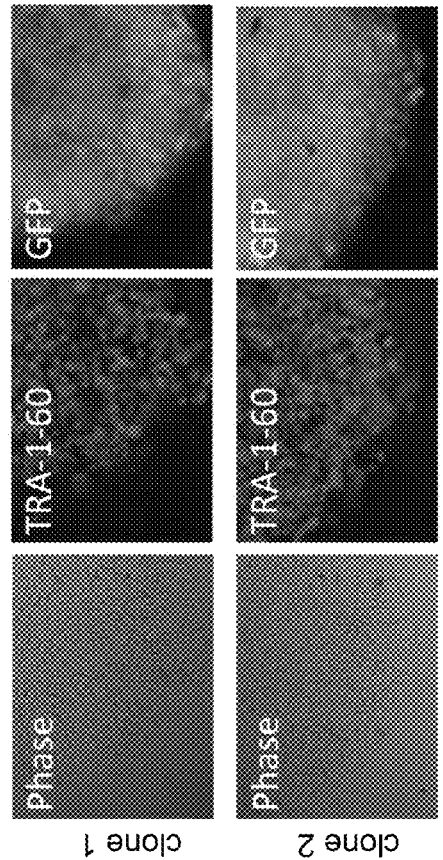
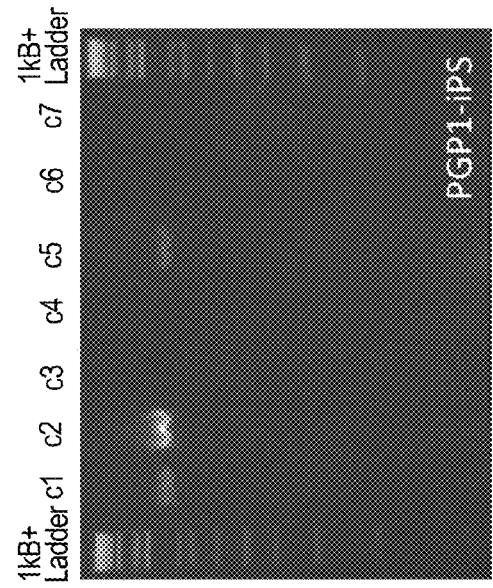
FIG. 12B

| FIG. 13A-1 |
| FIG. 13A-2 | gRNA target sites for genes in the human genome

...GNNNNNNNNNNNNNNNNNNNNGG...

↓ Incorporated into a 200bp DNA array based synthesis format

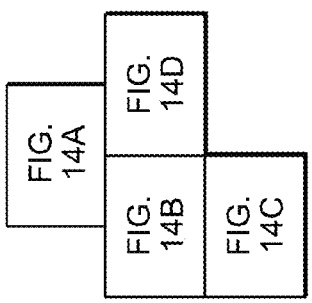
FIG. 14
FIG. 14A
Design of Reporters
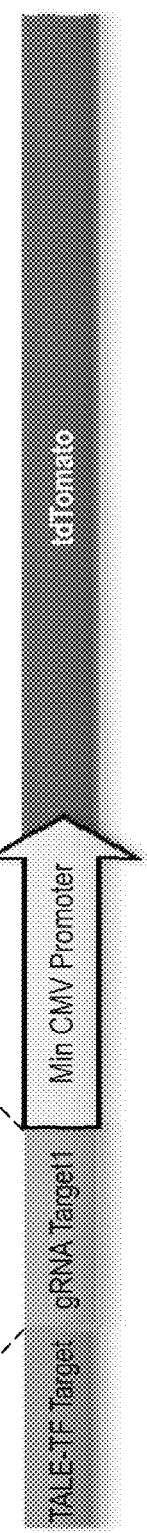
Reporter 1: GTCCCCTCCACCCCACAGTG GGG — TALE TF Target1 gRNA Target1 — Min CMV Promoter — tdTomato
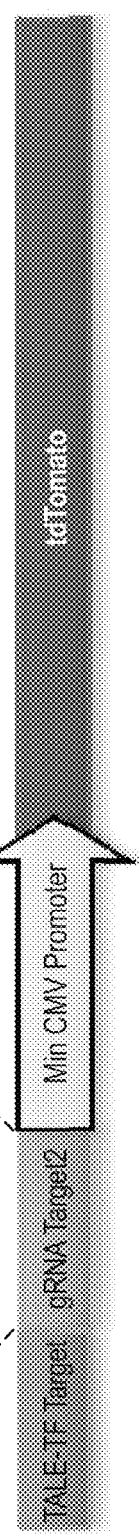
Reporter 2: GGGGCCACTAGGGACAGGAT TGG — TALE TF Target1 gRNA Target2 — Min CMV Promoter — tdTomato (a) Fluorescence Activated Cell Sorting (FACS) Analysis

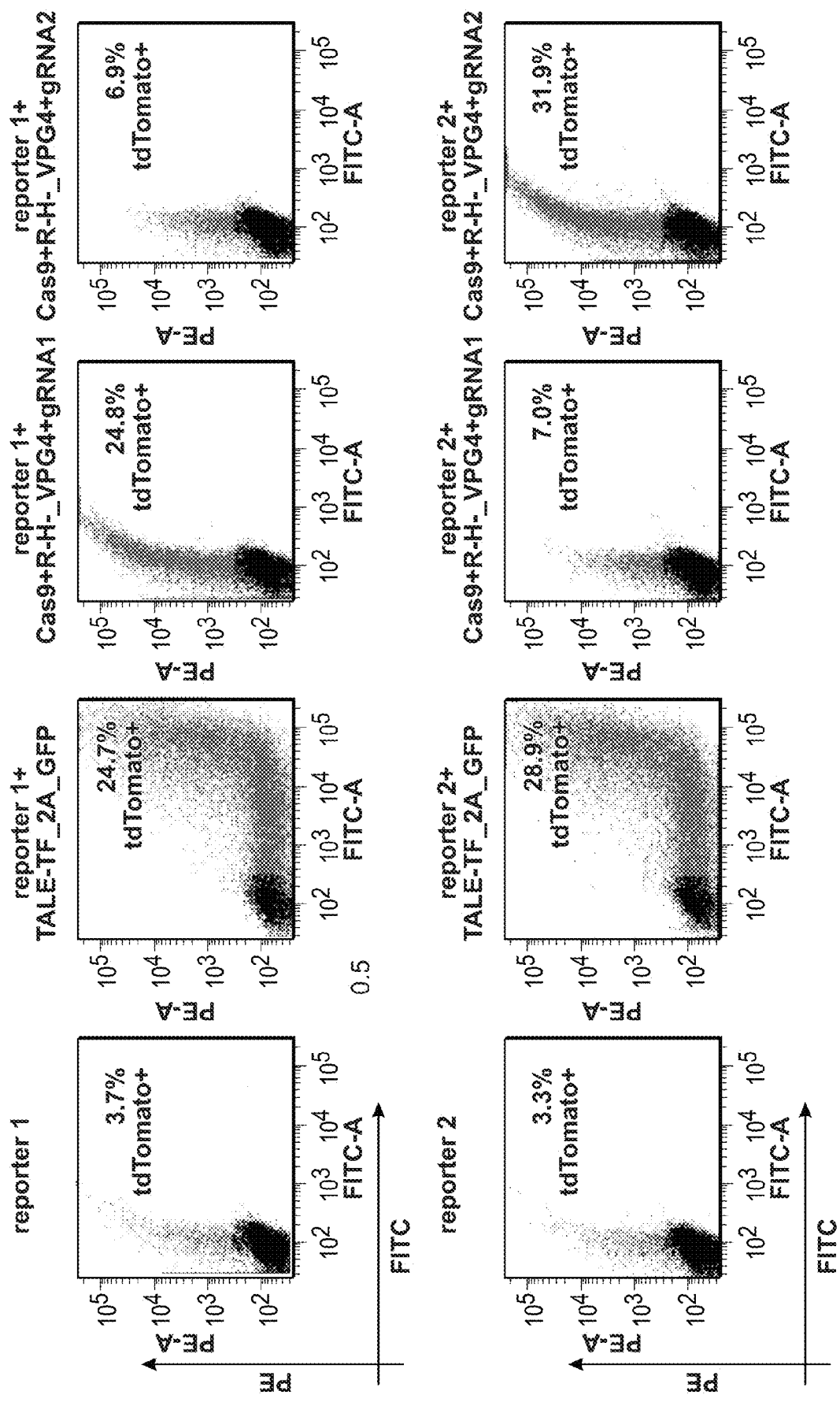

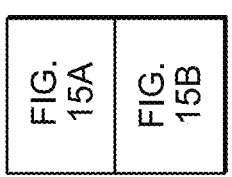
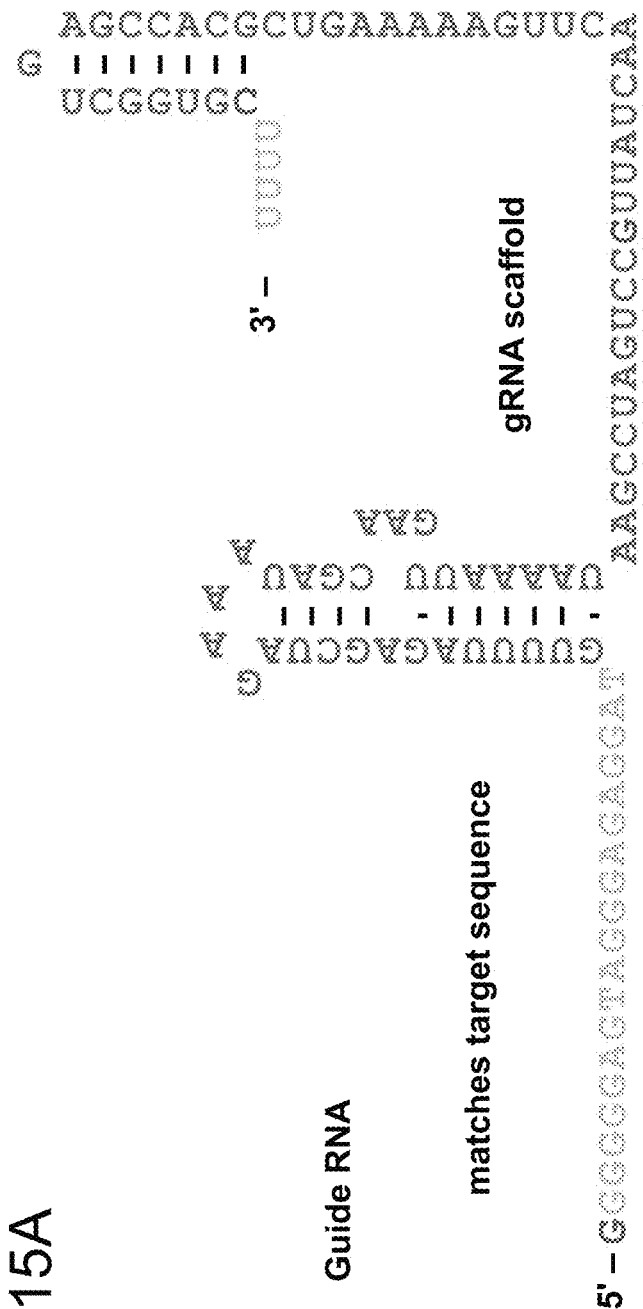
FIG. 15A

RNA-GUIDED HUMAN GENOME ENGINEERING

RELATED APPLICATION DATA

This application is a continuation application which claims priority to U.S. patent application Ser. No. 14/790,147, filed on Jul. 2, 2015, which is a continuation application which claims priority to U.S. patent application Ser. No. 14/653,144, filed on Jun. 17, 2015, which is a National Stage Application under 35 U.S.C. 371 of co-pending PCT application PCT/US2013/075317, filed Dec. 16, 2013 and U.S. provisional application No. 61/799,169, filed Mar. 13, 2013 and U.S. provisional application No. 61/738,355, filed Dec. 17, 2012 each of which is hereby incorporated herein by reference in their entirety for all purposes.

STATEMENT OF GOVERNMENT INTERESTS

This invention was made with government support under P50 HG005550 awarded by National Institutes of Health. The government has certain rights in the invention.

BACKGROUND

Bacterial and archaeal CRISPR systems rely on crRNAs in complex with Cas proteins to direct degradation of complementary sequences present within invading viral and plasmid DNA (1-3). A recent in vitro reconstitution of the *S. pyogenes* type II CRISPR system demonstrated that crRNA fused to a normally trans-encoded tracrRNA is sufficient to direct Cas9 protein to sequence-specifically cleave target DNA sequences matching the crRNA (4).

SUMMARY

The present disclosure references documents numerically which are listed at the end of the present disclosure. The document corresponding to the number is incorporated by reference into the specification as a supporting reference corresponding to the number as if fully cited.

According to one aspect of the present disclosure, a eukaryotic cell is transfected with a two component system including RNA complementary to genomic DNA and an enzyme that interacts with the RNA. The RNA and the enzyme are expressed by the cell. The RNA of the RNA/enzyme complex then binds to complementary genomic DNA. The enzyme then performs a function, such as cleavage of the genomic DNA. The RNA includes between about 10 nucleotides to about 250 nucleotides. The RNA includes between about 20 nucleotides to about 100 nucleotides. According to certain aspects, the enzyme may perform any desired function in a site specific manner for which the enzyme has been engineered. According to one aspect, the eukaryotic cell is a yeast cell, plant cell or mammalian cell. According to one aspect, the enzyme cleaves genomic sequences targeted by RNA sequences (see references (4-6)), thereby creating a genomically altered eukaryotic cell.

According to one aspect, the present disclosure provides a method of genetically altering a human cell by including a nucleic acid encoding an RNA complementary to genomic DNA into the genome of the cell and a nucleic acid encoding an enzyme that performs a desired function on genomic DNA into the genome of the cell. According to one aspect, the RNA and the enzyme are expressed. According to one aspect, the RNA hybridizes with complementary genomic DNA. According to one aspect, the enzyme is activated to perform a desired function, such as cleavage, in a site specific manner when the RNA is hybridized to the complementary genomic DNA. According to one aspect, the RNA and the enzyme are components of a bacterial Type II CRISPR system.

According to one aspect, a method of altering a eukaryotic cell is providing including transfecting the eukaryotic cell with a nucleic acid encoding RNA complementary to genomic DNA of the eukaryotic cell, transfecting the eukaryotic cell with a nucleic acid encoding an enzyme that interacts with the RNA and cleaves the genomic DNA in a site specific manner, wherein the cell expresses the RNA and the enzyme, the RNA binds to complementary genomic DNA and the enzyme cleaves the genomic DNA in a site specific manner. According to one aspect, the enzyme is Cas9 or modified Cas9 or a homolog of Cas9. According to one aspect, the eukaryotic cell is a yeast cell, a plant cell or a mammalian cell. According to one aspect, the RNA includes between about 10 to about 250 nucleotides. According to one aspect, the RNA includes between about 20 to about 100 nucleotides.

According to one aspect, a method of altering a human cell is provided including transfecting the human cell with a nucleic acid encoding RNA complementary to genomic DNA of the eukaryotic cell, transfecting the human cell with a nucleic acid encoding an enzyme that interacts with the RNA and cleaves the genomic DNA in a site specific manner, wherein the human cell expresses the RNA and the enzyme, the RNA binds to complementary genomic DNA and the enzyme cleaves the genomic DNA in a site specific manner. According to one aspect, the enzyme is Cas9 or modified Cas9 or a homolog of Cas9. According to one aspect, the RNA includes between about 10 to about 250 nucleotides. According to one aspect, the RNA includes between about 20 to about 100 nucleotides.

According to one aspect, a method of altering a eukaryotic cell at a plurality of genomic DNA sites is provided including transfecting the eukaryotic cell with a plurality of nucleic acids encoding RNAs complementary to different sites on genomic DNA of the eukaryotic cell, transfecting the eukaryotic cell with a nucleic acid encoding an enzyme that interacts with the RNA and cleaves the genomic DNA in a site specific manner, wherein the cell expresses the RNAs and the enzyme, the RNAs bind to complementary genomic DNA and the enzyme cleaves the genomic DNA in a site specific manner. According to one aspect, the enzyme is Cas9. According to one aspect, the eukaryotic cell is a yeast cell, a plant cell or a mammalian cell. According to one aspect, the RNA includes between about 10 to about 250 nucleotides. According to one aspect, the RNA includes between about 20 to about 100 nucleotides.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1B depicts a genomically integrated GFP coding sequence disrupted by the insertion of a stop codon and a 68 bp genomic fragment from the AAVS1 locus (SEQ ID NO:18). FIG. 1C-2 depicts FACS plots and microscopy images of the targeted cells.

FIG. 2A depicts RNA-guided genome editing of the native AAVS1 locus in multiple cell types (SEQ ID NO:19). FIG. 2B-1, FIG. 2B-2, and FIG. 2B-3 depict total count and location of deletions caused by NHEJ in 293Ts, K562s, and PGP1 iPS cells. FIG. 2C depicts DNA donor architecture for HR at the AAVS1 locus, and the locations of sequencing primers (arrows) for detecting successful targeted events.

FIG. 3A-1 and FIG. 3A-2 depict a human codon-optimized version of the Cas9 protein and full sequence of the cas9 gene insert (SEQ ID NO:22). FIG. 3B depicts U6 promoter based expression scheme for the guide RNAs and predicted RNA transcript secondary structure (SEQ ID NO:23). FIG. 3C depicts targeted $GN_{20}GG$ genomic sites and selected gRNAs (SEQ ID NOs:24-31).

FIG. 7 depicts gRNAs targeting the flanking GFP sequences of the reporter described in FIG. 1B (in 293Ts).

FIGS. 8A-8B depict 293T stable lines each bearing a distinct GFP reporter construct (SEQ ID NOs:35-36).

FIG. 11A-11B depict RNA-guided NHEJ in 293T cells (SEQ ID NO:19).

FIGS. 12A-12C depict HR at the endogenous AAVS1 locus using either a dsDNA donor or a short oligonucleotide donor (SEQ ID NOs:37-38).

FIG. 13A-1 and FIG. 13A-2 and FIG. 13B depict the methodology for multiplex synthesis, retrieval and U6 expression vector cloning of guide RNAs targeting genes in the human genome (SEQ ID NOs:39-41).

FIGS. 14A-14D depict CRISPR mediated RNA-guided transcriptional activation (SEQ ID NOs:42-43).

FIGS. 15A-15B depict gRNA sequence flexibility and applications thereof (SEQ ID NO:44-46).

DETAILED DESCRIPTION

Figure 1A:
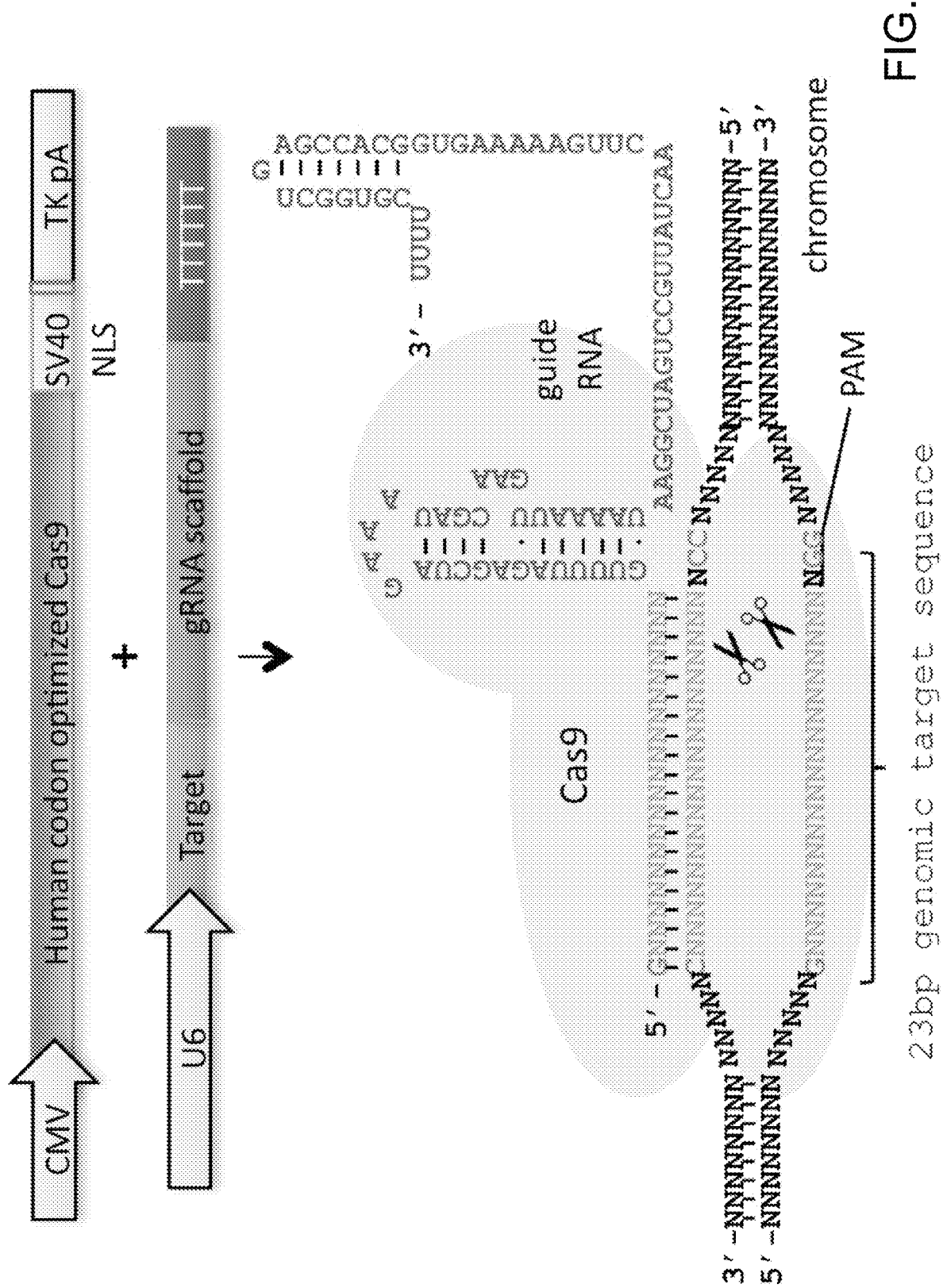
FIG. 1A depicts genome editing in human cells using an engineered type II CRISPR system (SEQ ID NO:17 and 45-46).
Figures 1, 1C:
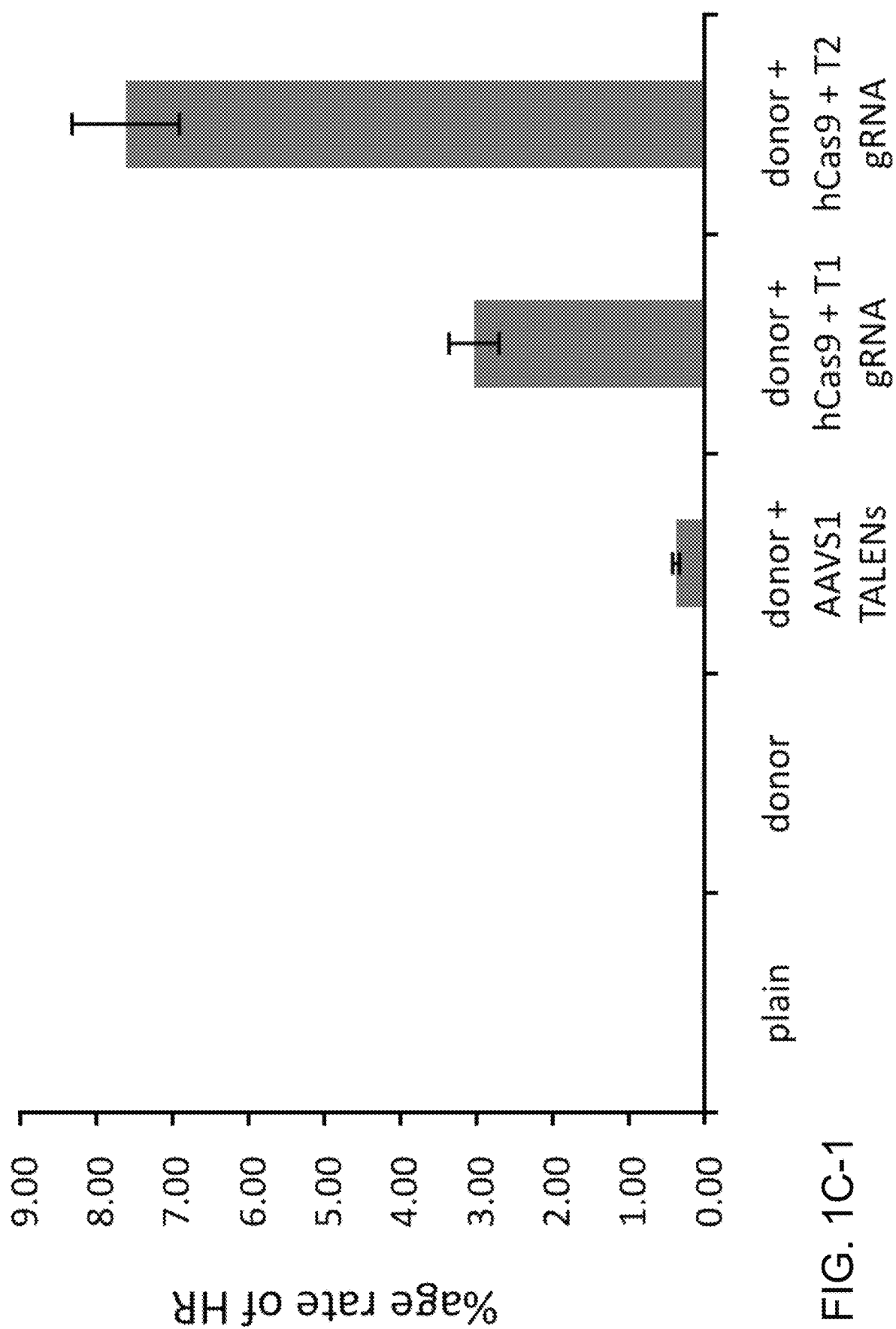
FIG. 1C-1 bar graph depicts HR efficiencies induced by T1, T2, and TALEN-mediated nuclease activity at the target locus, as measured by FACS.
Figures 2A, 2B:
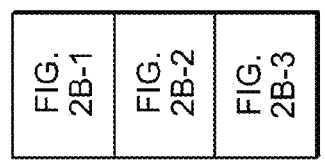
Figures 1, 2B:
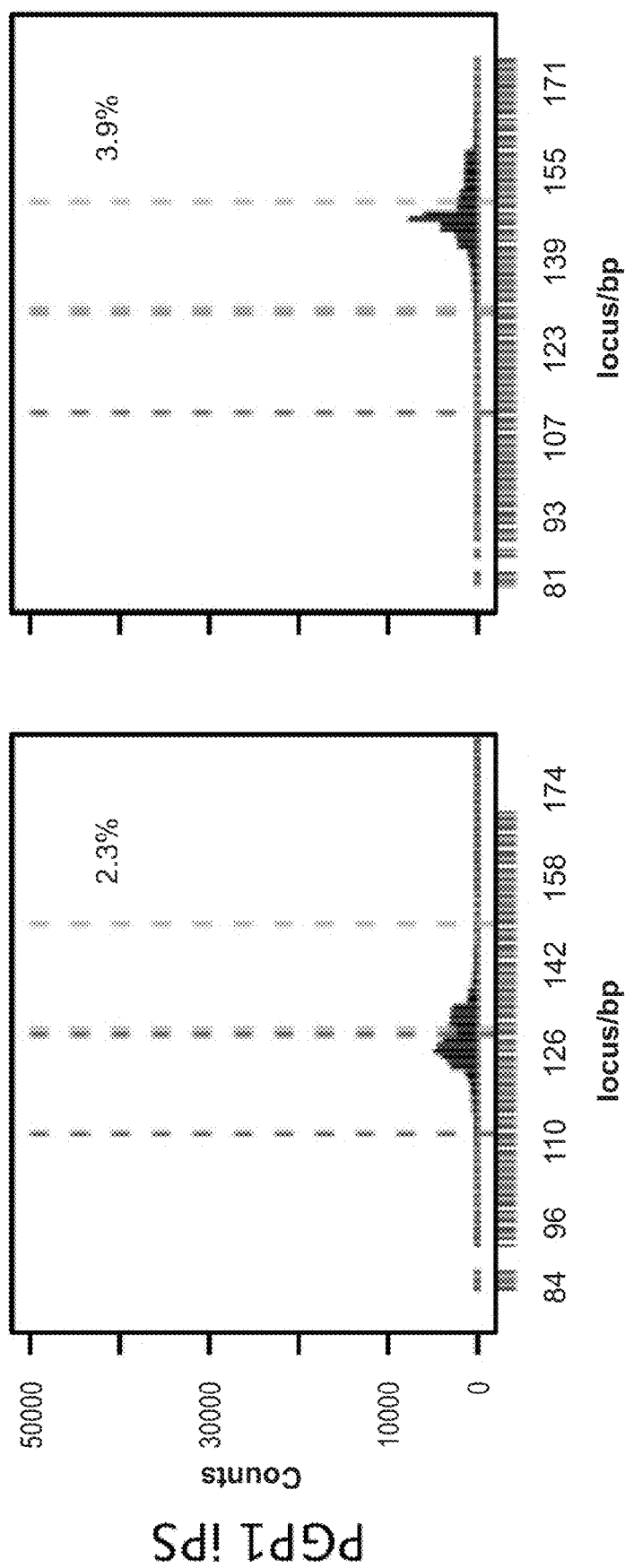
Figures 2, 2B:
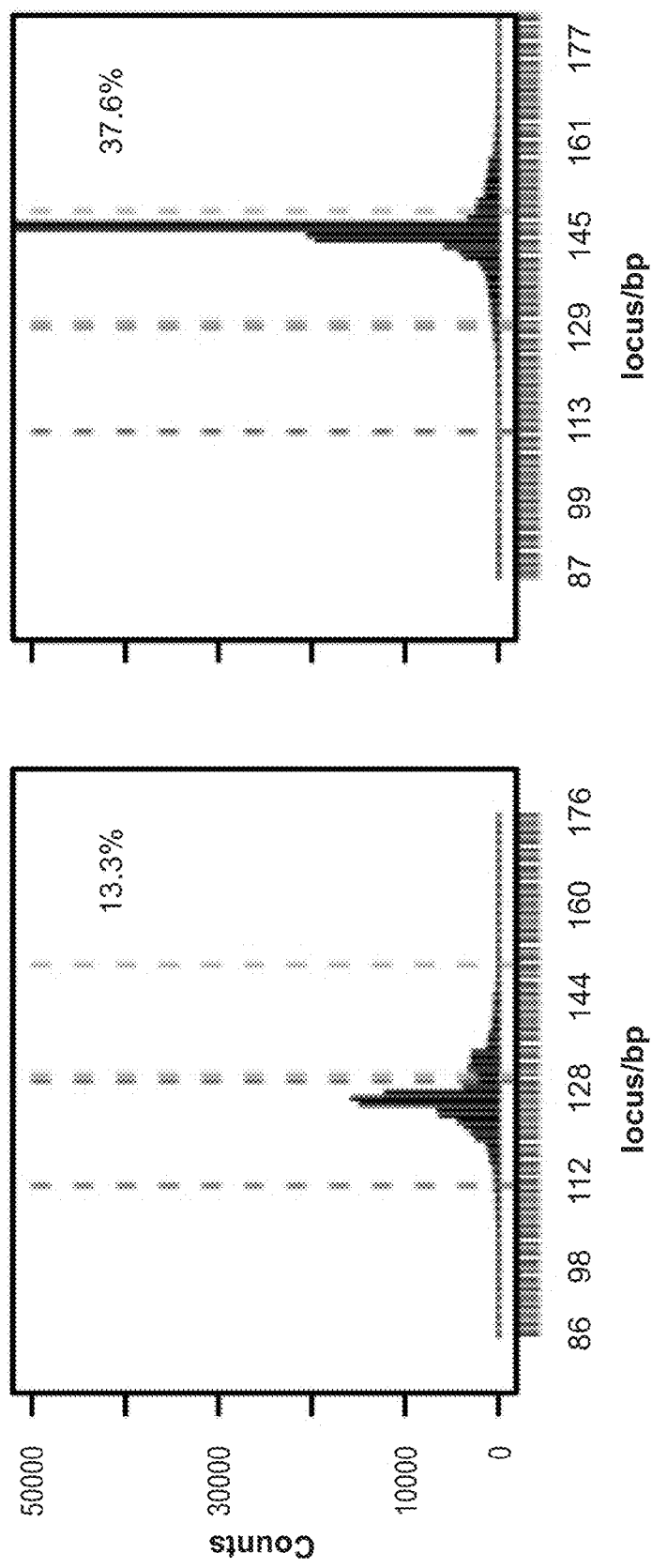

According to one aspect, a human codon-optimized version of the Cas9 protein bearing a C-terminus SV40 nuclear localization signal is synthetized and cloned into a mammalian expression system (FIG. 1A and FIGS. 3A-1 and 3A-2). Accordingly, FIG. 1 is directed to genome editing in human cells using an engineered type II CRISPR system. As shown in FIG. 1A, RNA-guided gene targeting in human cells involves co-expression of the Cas9 protein bearing a C-terminus SV40 nuclear localization signal with one or more guide RNAs (gRNAs) expressed from the human U6 polymerase III promoter. Cas9 unwinds the DNA duplex and cleaves both strands upon recognition of a target sequence by the gRNA, but only if the correct protospacer-adjacent motif (PAM) is present at the 3' end. Any genomic sequence of the form $GN_{20}GG$ can in principle be targeted. As shown in FIG. 1B, a genomically integrated GFP coding sequence is disrupted by the insertion of a stop codon and a 68 bp genomic fragment from the AAVS1 locus. Restoration of the GFP sequence by homologous recombination (HR) with an appropriate donor sequence results in GFP cells that can be quantitated by FACS. T1 and T2 gRNAs target sequences within the AAVS1 fragment. Binding sites for the two halves of the TAL effector nuclease heterodimer (TALEN) are underlined. As shown in FIG. 1C-1, bar graph depict HR efficiencies induced by T1, T2, and TALEN-mediated nuclease activity at the target locus, as measured by FACS. Representative FACS plots and microscopy images of the targeted cells, FIG. 1C-2, are depicted below (scale bar is 100 microns). Data is mean+/−SEM (N=3).

According to one aspect, to direct Cas9 to cleave sequences of interest, crRNA-tracrRNA fusion transcripts are expressed, hereafter referred to as guide RNAs (gRNAs), from the human U6 polymerase III promoter. According to one aspect, gRNAs are directly transcribed by the cell. This aspect advantageously avoids reconstituting the RNA processing machinery employed by bacterial CRISPR systems (FIG. 1A and FIG. 3B) (see references (4, 7-9)). According to one aspect, a method is provided for altering genomic DNA using a U6 transcription initiating with G and a PAM (protospacer-adjacent motif) sequence -NGG following the 20 bp crRNA target. According to this aspect, the target genomic site is in the form of $GN_{20}GG$ (See FIG. 3C).

According to one aspect, a GFP reporter assay (FIG. 1B) in 293T cells was developed similar to one previously described (see reference (10)) to test the functionality of the genome engineering methods described herein. According to one aspect, a stable cell line was established bearing a genomically integrated GFP coding sequence disrupted by the insertion of a stop codon and a 68 bp genomic fragment from the AAVS1 locus that renders the expressed protein fragment non-fluorescent. Homologous recombination (HR) using an appropriate repair donor can restore the normal GFP sequence, which allows one to quantify the resulting GFP cells by flow activated cell sorting (FACS).

Figure 4:
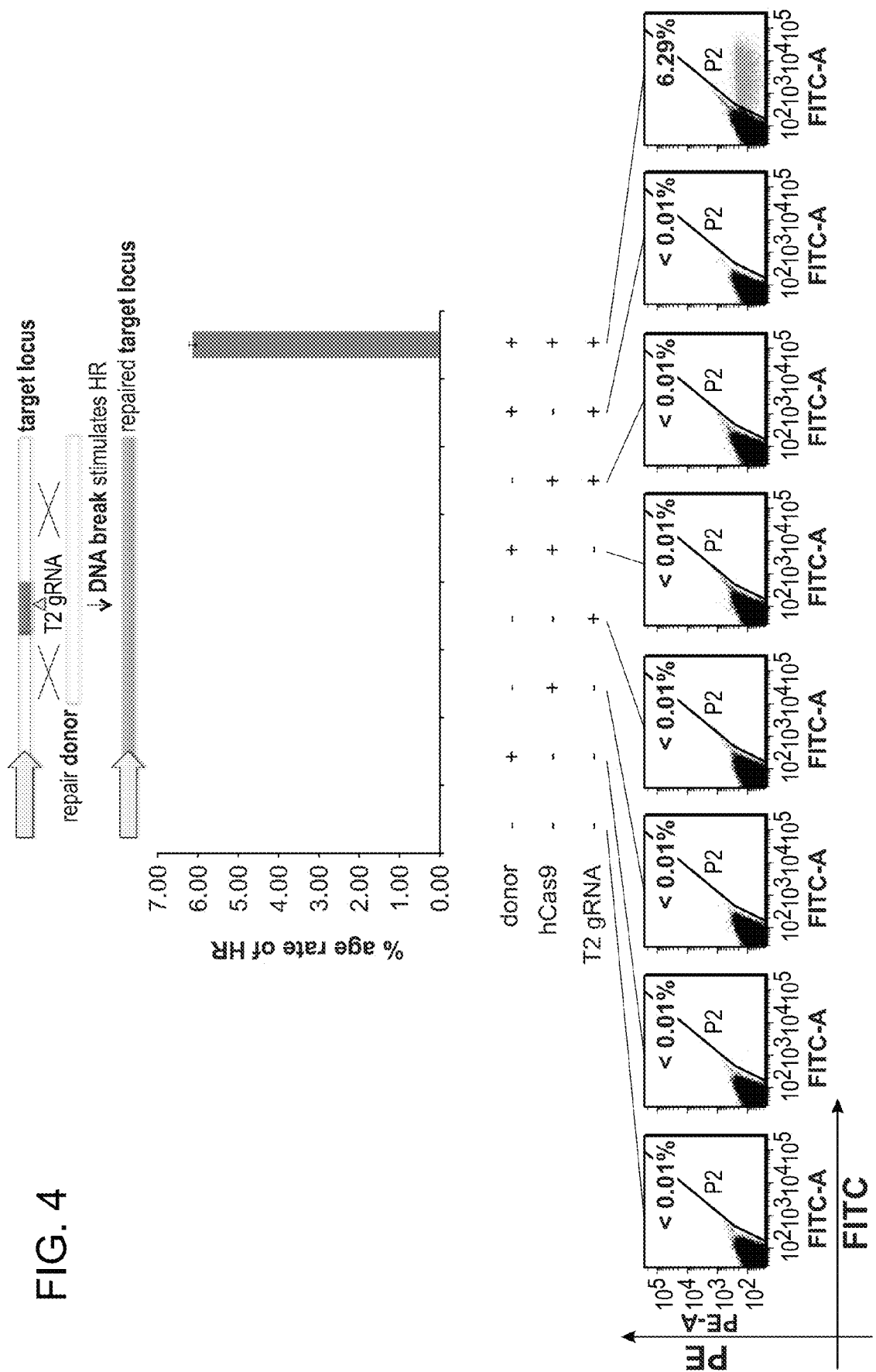
FIG. 4 depicts that all possible combinations of the repair DNA donor, Cas9 protein, and gRNA were tested for their ability to effect successful HR in 293Ts.

According to one aspect, a method is provided of homologous recombination (HR). Two gRNAs are constructed, T1 and T2, that target the intervening AAVS1 fragment (FIG. 1b). Their activity to that of a previously described TAL effector nuclease heterodimer (TALEN) targeting the same region (see reference (11)) was compared. Successful HR events were observed using all three targeting reagents, with gene correction rates using the T1 and T2 gRNAs approaching 3% and 8% respectively (FIG. 1C-1). This RNA-mediated editing process was notably rapid, with the first detectable GFP cells appearing ~20 hours post transfection compared to ~40 hours for the AAVS1 TALENs. HR was observed only upon simultaneous introduction of the repair donor, Cas9 protein, and gRNA, confirming that all components are required for genome editing (FIG. 4). While no apparent toxicity associated with Cas9/crRNA expression was noted, work with ZFNs and TALENs has shown that nicking only one strand further reduces toxicity. Accordingly, a Cas9D10A mutant was tested that is known to function as a nickase in vitro, which yielded similar HR but lower non-homologous end joining (NHEJ) rates (FIG. 5) (see references (4, 5)). Consistent with (4) where a related Cas9 protein is shown to cut both strands 6 bp upstream of the PAM, NHEJ data confirmed that most deletions or insertions occurred at the 3' end of the target sequence (FIG.

Figures 6, 6A:
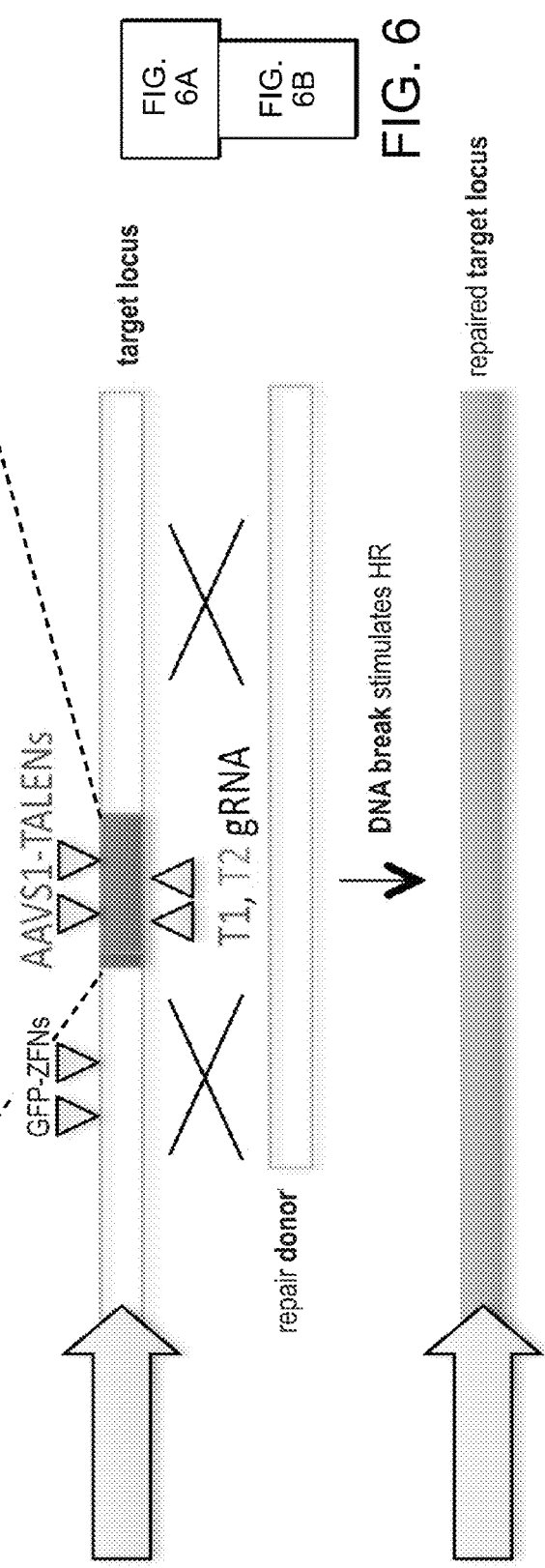
FIGS. 6A-6B depict 293T stable lines each bearing a distinct GFP reporter construct (SEQ ID NOs:32-34).
Figure 6B:
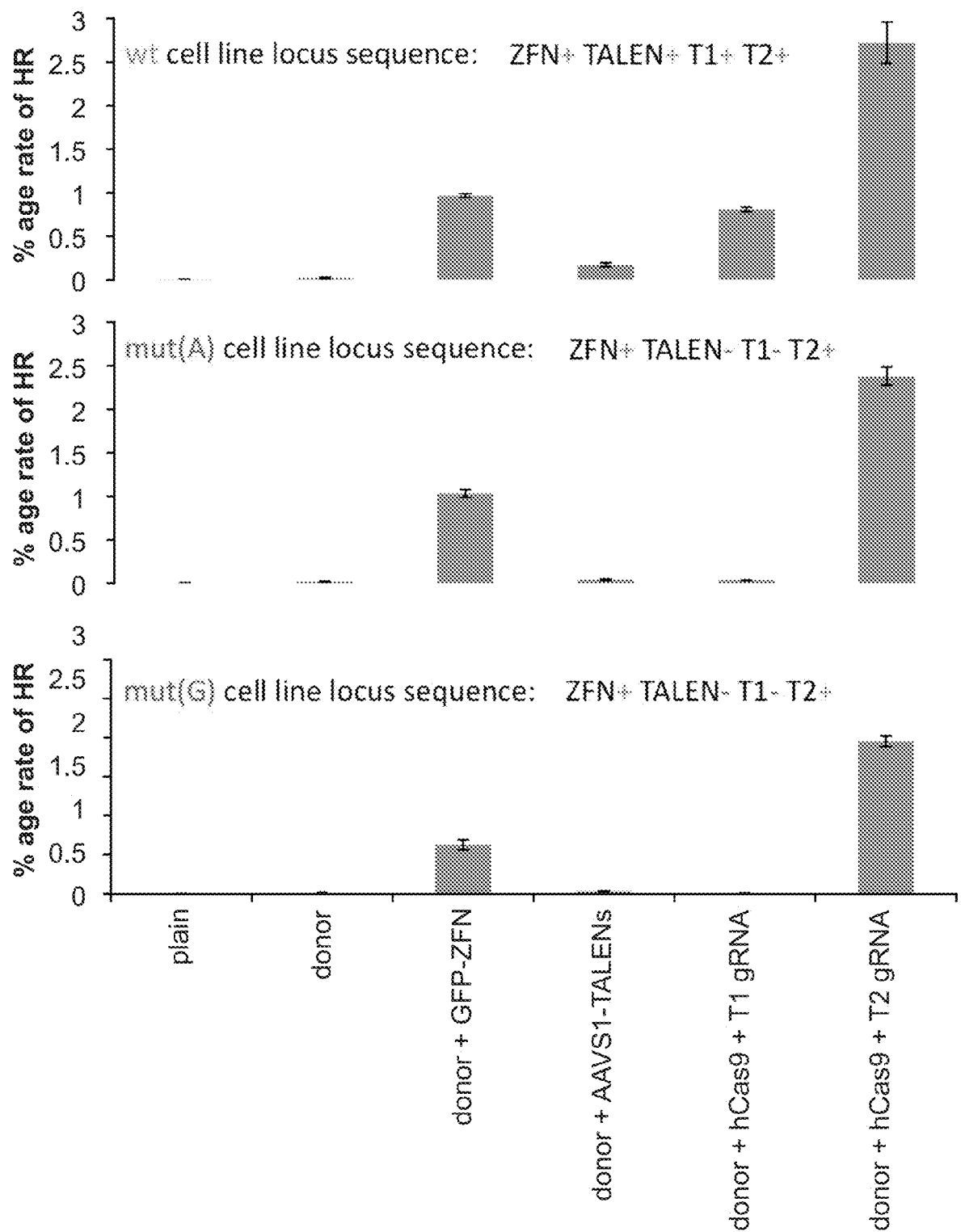

5B). Also confirmed was that mutating the target genomic site prevents the gRNA from effecting HR at that locus, demonstrating that CRISPR-mediated genome editing is sequence specific (FIGS. 6A and 6B). It was showed that two gRNAs targeting sites in the GFP gene, and also three additional gRNAs targeting fragments from homologous regions of the DNA methyl transferase 3a (DNMT3a) and DNMT3b genes could sequence specifically induce significant HR in the engineered reporter cell lines (FIG. 7, 8). Together these results confirm that RNA-guided genome targeting in human cells induces robust HR across multiple target sites.

According to certain aspects, a native locus was modified. gRNAs were used to target the AAVS1 locus located in the PPP1R12C gene on chromosome 19, which is ubiquitously expressed across most tissues (FIG. 2A) in 293Ts, K562s, and PGP1 human iPS cells (see reference (12)) and analyzed the results by next-generation sequencing of the targeted locus. Accordingly, FIG. 2 is directed to RNA-guided genome editing of the native AAVS1 locus in multiple cell types. As shown in FIG. 2A, T1 (red) and T2 (green) gRNAs target sequences in an intron of the PPP1R12C gene within the chromosome 19 AAVS1 locus. As shown in FIGS. 2B-1, 2B-2, and 2B-3, total count and location of deletions caused by NHEJ in 293Ts, K562s, and PGP1 iPS cells following expression of Cas9 and either T1 or T2 gRNAs as quantified by next-generation sequencing is provided. Red and green dash lines demarcate the boundaries of the T1 and T2 gRNA targeting sites. NHEJ frequencies for T1 and T2 gRNAs were 10% and 25% in 293T, 13% and 38% in K562, and 2% and 4% in PGP1 iPS cells, respectively. As shown in FIG. 2C, DNA donor architecture for HR at the AAVS1 locus, and the locations of sequencing primers (arrows) for detecting successful targeted events, are depicted. As shown in FIG. 2D, PCR assay three days post transfection demonstrates that only cells expressing the donor, Cas9 and T2 gRNA exhibit successful HR events. As shown in FIG. 2E, successful HR was confirmed by Sanger sequencing of the PCR amplicon showing that the expected DNA bases at both the genome-donor and donor-insert boundaries are present. As shown in FIG. 2F, successfully targeted clones of 293T cells were selected with puromycin for 2 weeks. Microscope images of two representative GFP+ clones is shown (scale bar is 100 microns).

Figure 9:
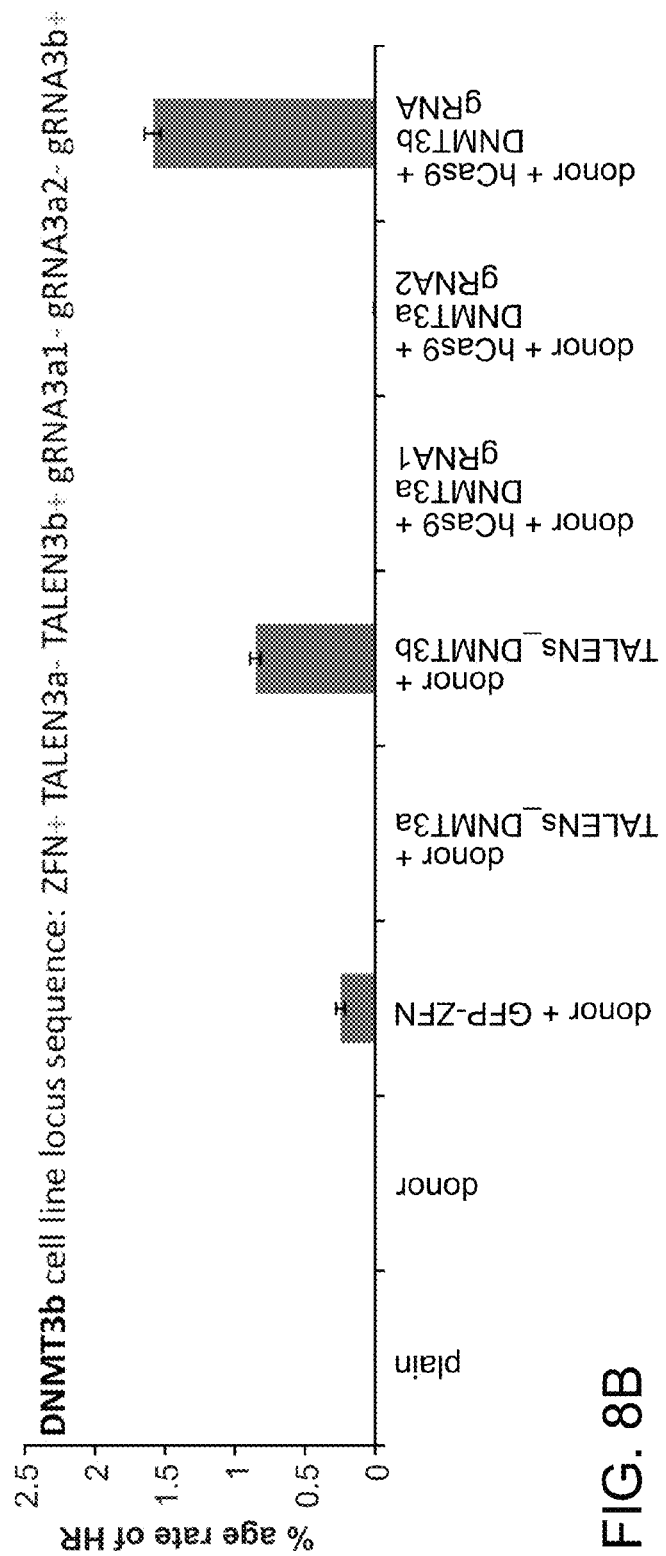
FIGS. 9A-9C depict human iPS cells (PGP1) that were nucleofected with constructs (SEQ ID NO:19).
Figure 9A:
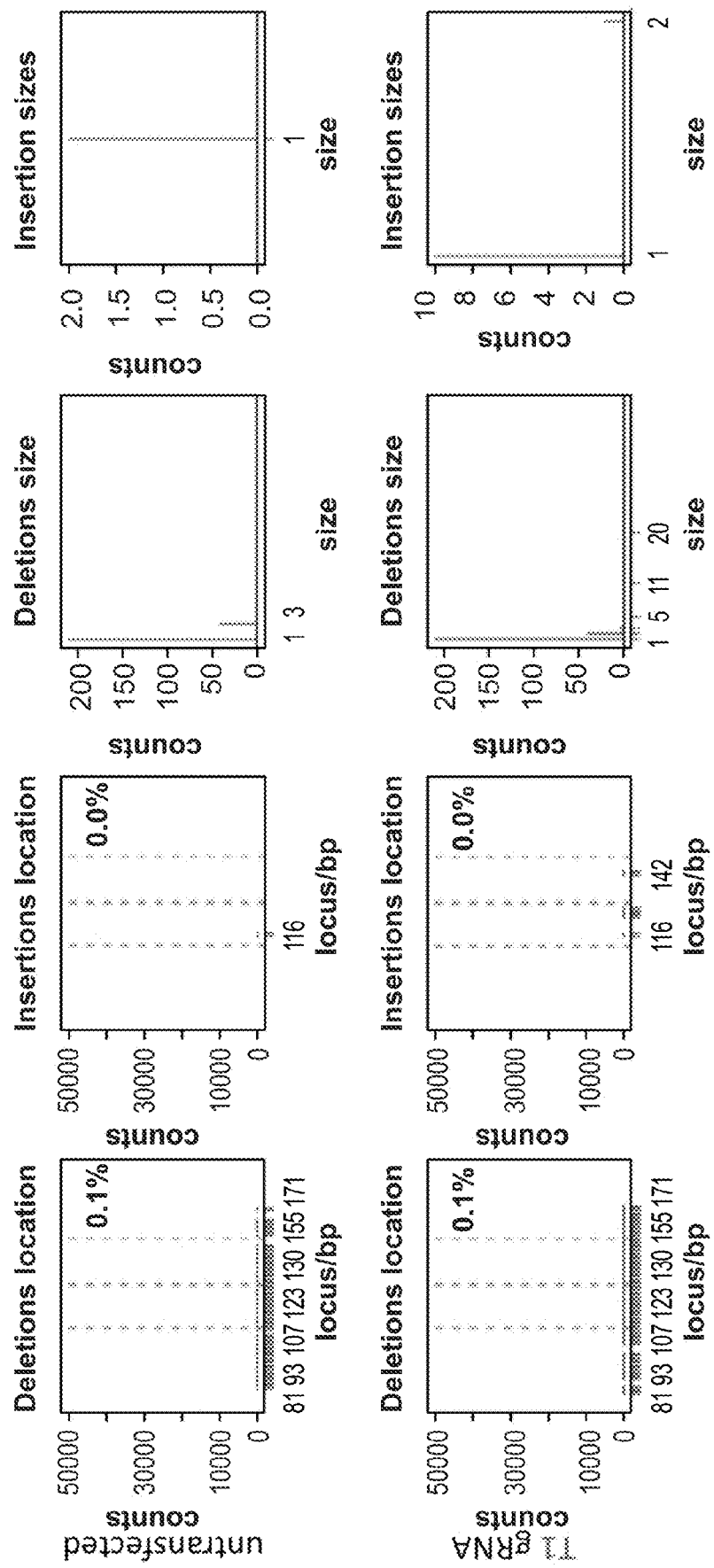
Figure 9B:
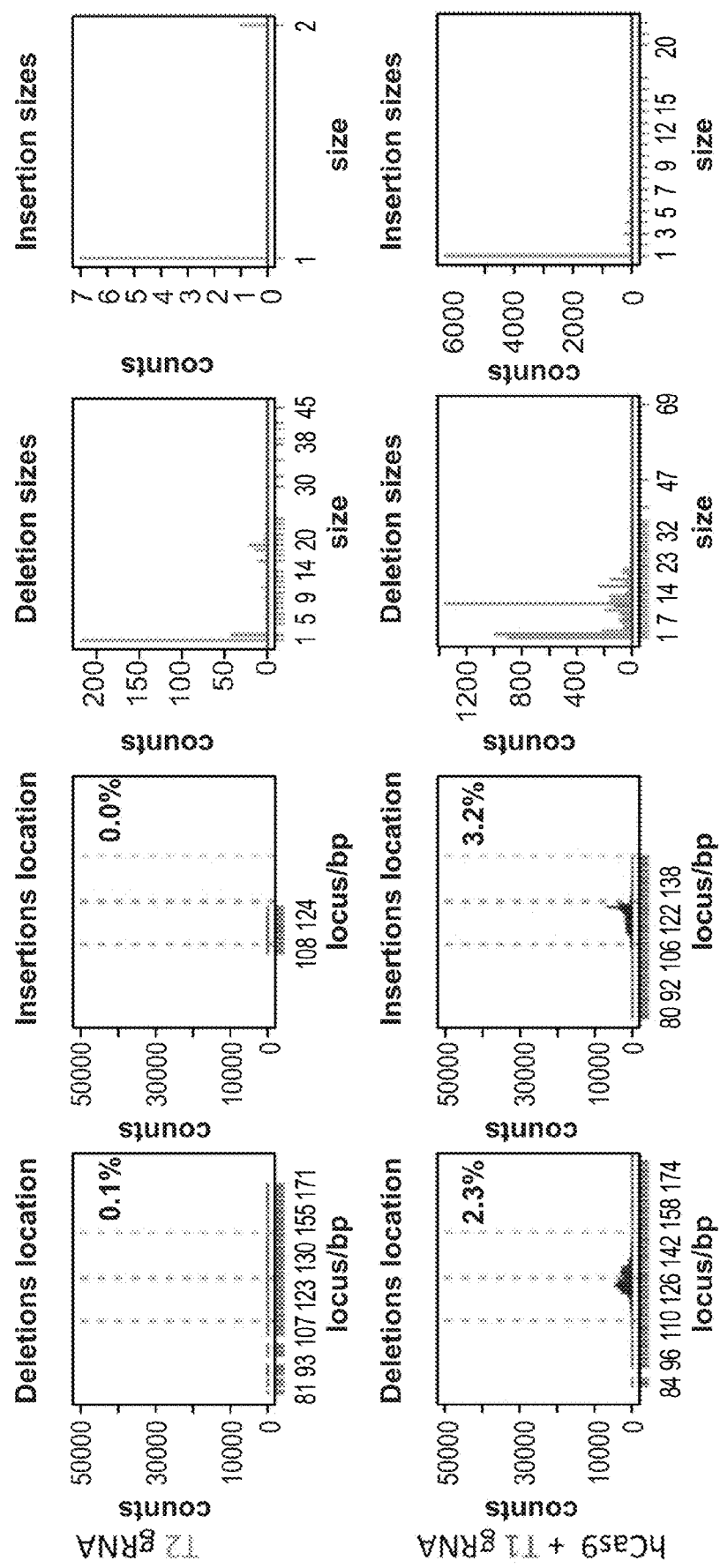
Figure 9C:
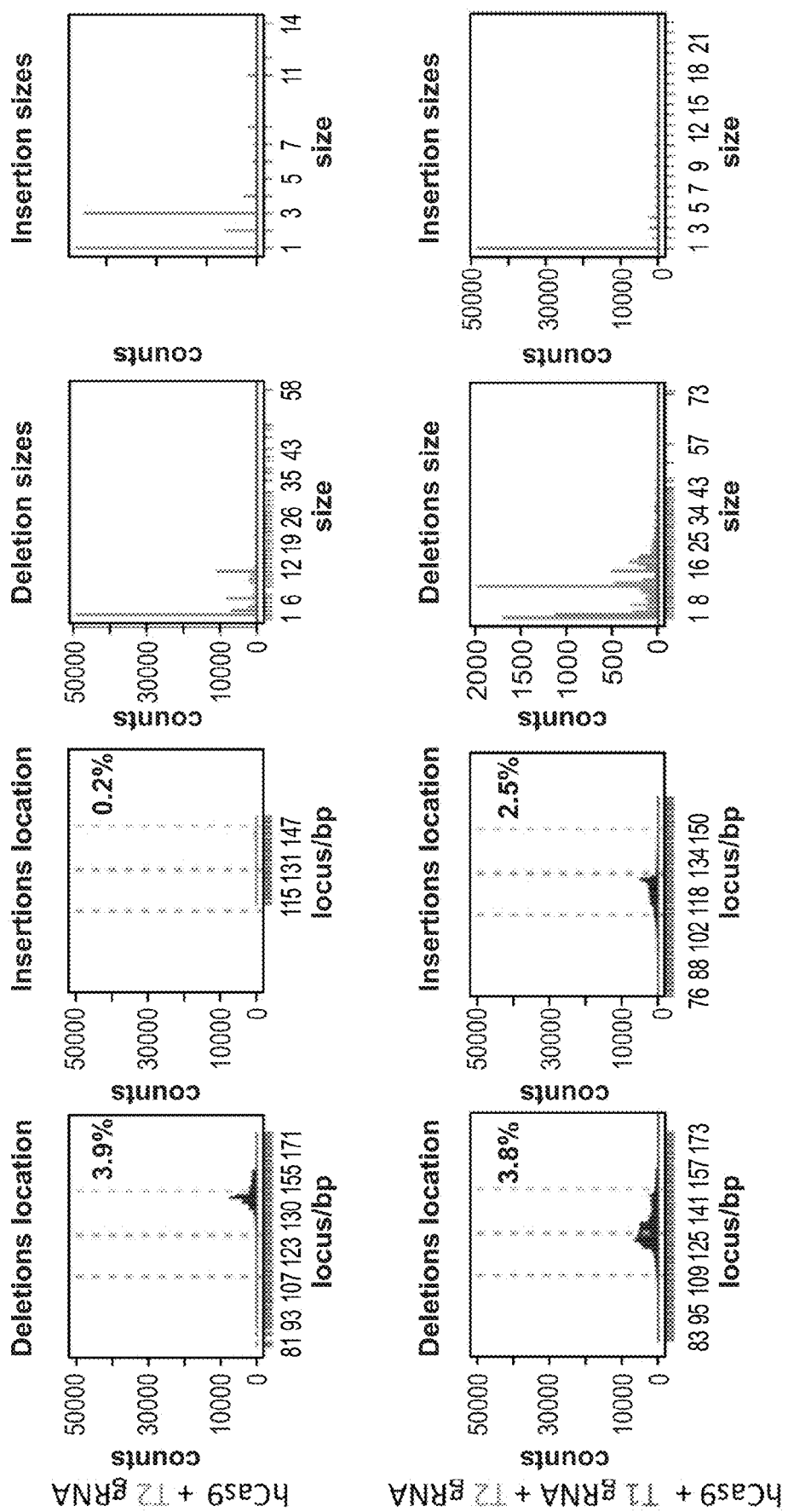

Consistent with results for the GFP reporter assay, high numbers of NHEJ events were observed at the endogenous locus for all three cell types. The two gRNAs T1 and T2 achieved NHEJ rates of 10 and 25% in 293Ts, 13 and 38% in K562s, and 2 and 4% in PGP1-iPS cells, respectively (FIGS. 2B-1, 2B-2, and 2B-3). No overt toxicity was observed from the Cas9 and crRNA expression required to induce NHEJ in any of these cell types (FIGS. 9A, 9B, and 9C). As expected, NHEJ-mediated deletions for T1 and T2 were centered around the target site positions, further validating the sequence specificity of this targeting process (FIGS. 9A-C, 10, 11). Simultaneous introduction of both T1 and T2 gRNAs resulted in high efficiency deletion of the intervening 19 bp fragment (FIGS. 10A and 10B), demonstrating that multiplexed editing of genomic loci is feasible using this approach.

Figure 12C:
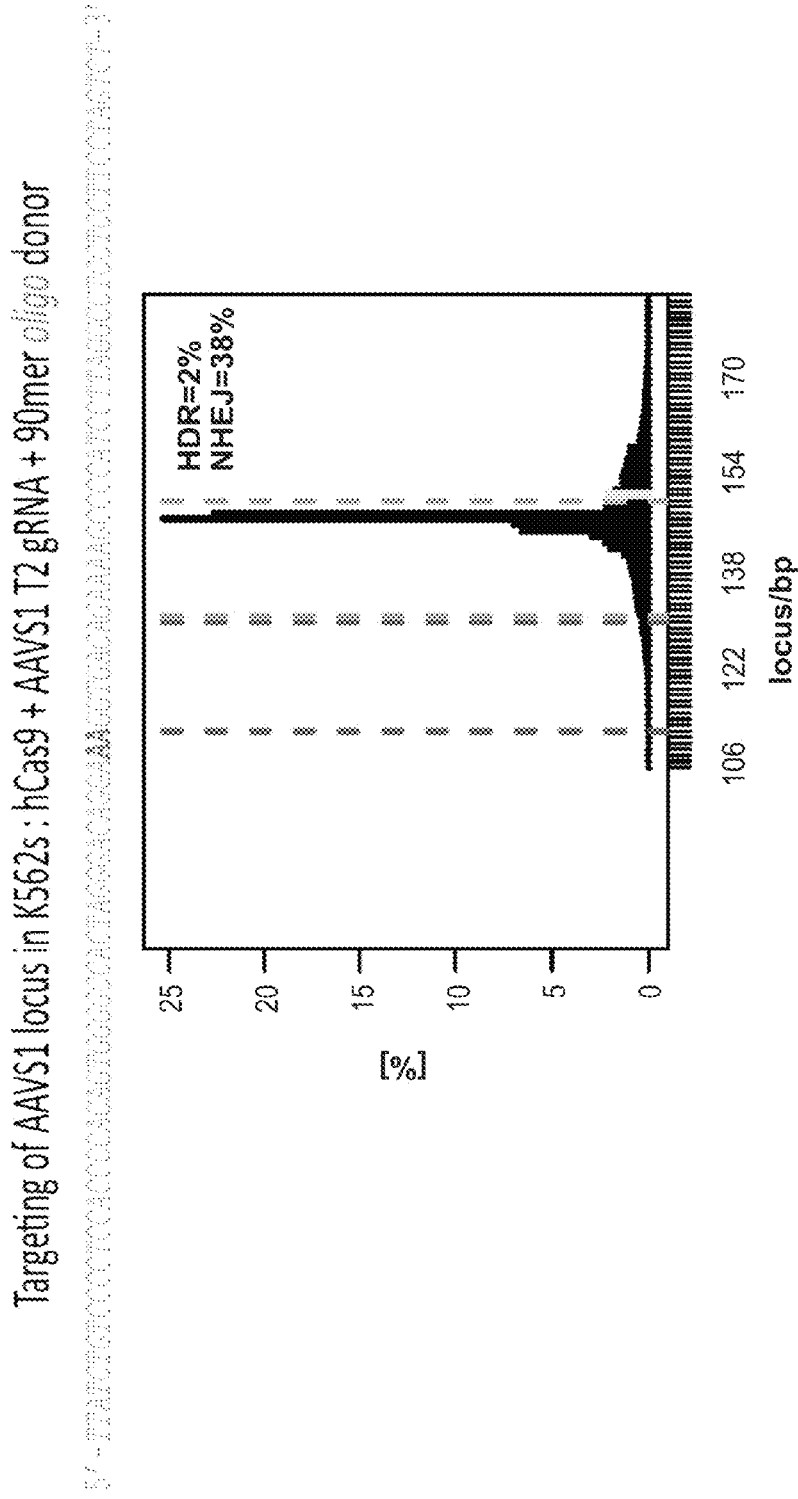

According to one aspect, HR is used to integrate either a dsDNA donor construct (see reference (13)) or an oligo donor into the native AAVS1 locus (FIG. 2C, FIG. 12C). HR-mediated integration was confirmed using both approaches by PCR (FIG. 2D, FIG. 12A) and Sanger sequencing (FIG. 2E). 293T or iPS clones were readily derived from the pool of modified cells using puromycin selection over two weeks (FIG. 2F, FIG. 12B). These results demonstrate that Cas9 is capable of efficiently integrating foreign DNA at endogenous loci in human cells. Accordingly, one aspect of the present disclosure includes a method of integrating foreign DNA into the genome of a cell using homologous recombination and Cas9.

Figures 2, 13A:
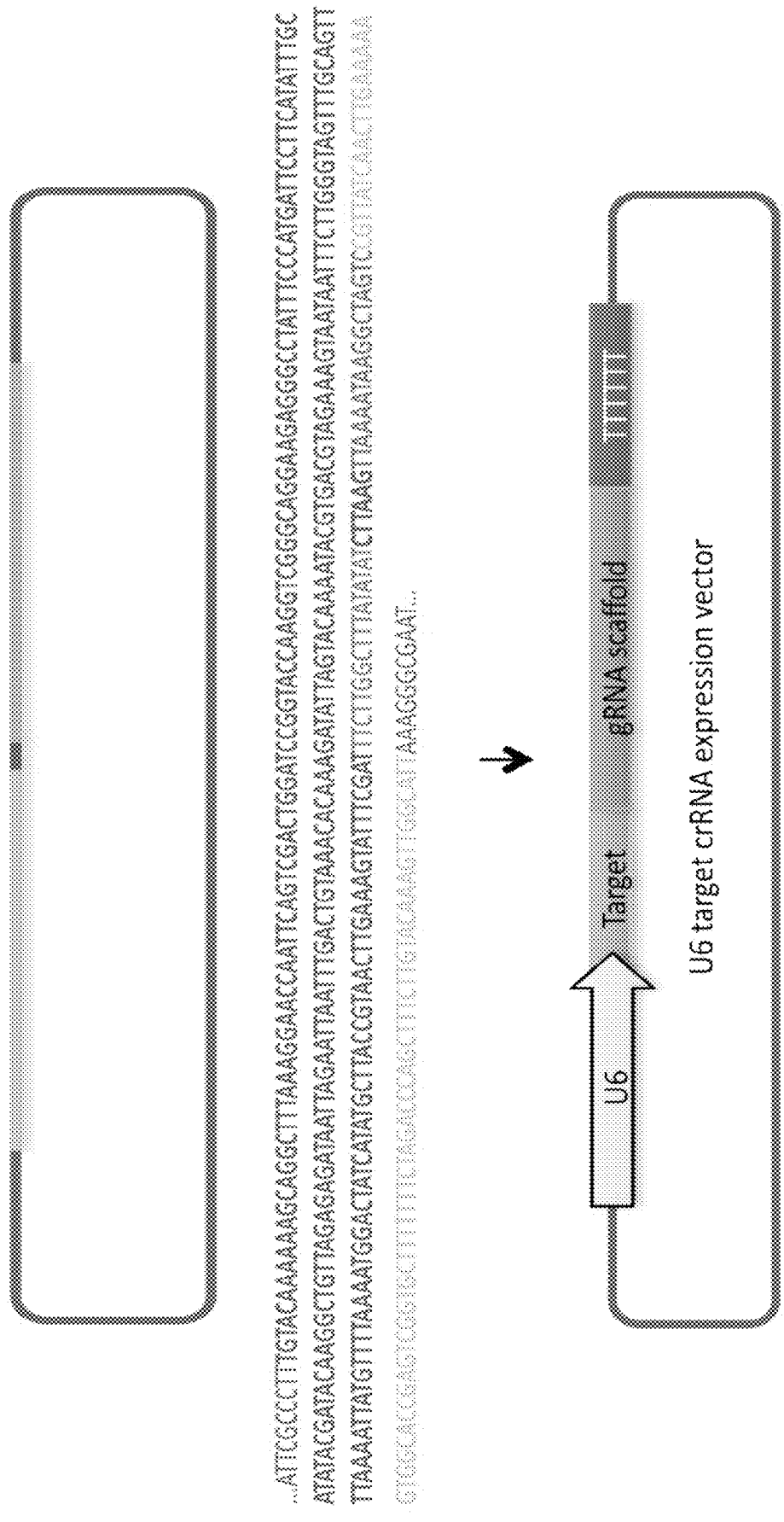

According to one aspect, an RNA-guided genome editing system is provided which can readily be adapted to modify other genomic sites by simply modifying the sequence of the gRNA expression vector to match a compatible sequence in the locus of interest. According to this aspect, 190,000 specifically gRNA-targetable sequences targeting about 40.5% exons of genes in the human genome were generated. These target sequences were incorporated into a 200 bp format compatible with multiplex synthesis on DNA arrays (see reference (14)) (FIGS. 13A-1 and 13A-2). According to this aspect, a ready genome-wide reference of potential target sites in the human genome and a methodology for multiplex gRNA synthesis is provided.

According to one aspect, methods are provided for multiplexing genomic alterations in a cell by using one or more or a plurality of RNA/enzyme systems described herein to alter the genome of a cell at a plurality of locations. According to one aspect, target sites perfectly match the PAM sequence NGG and the 8-12 base "seed sequence" at the 3' end of the gRNA. According to certain aspects, perfect match is not required of the remaining 8-12 bases. According to certain aspects, Cas9 will function with single mismatches at the 5' end. According to certain aspects, the target locus's underlying chromatin structure and epigenetic state may affect efficiency of Cas9 function. According to certain aspects, Cas9 homologs having higher specificity are included as useful enzymes. One of skill in the art will be able to identify or engineer suitable Cas9 homologs. According to one aspect, CRISPR-targetable sequences include those having different PAM requirements (see reference (9)), or directed evolution. According to one aspect, inactivating one of the Cas9 nuclease domains increases the ratio of HR to NHEJ and may reduce toxicity (FIGS. 3A-1 and 3A-2, FIG. 5) (4, 5), while inactivating both domains may enable Cas9 to function as a retargetable DNA binding protein. Embodiments of the present disclosure have broad utility in synthetic biology (see references (21, 22)), the direct and multiplexed perturbation of gene networks (see references (13, 23)), and targeted ex vivo (see references (24-26)) and in vivo gene therapy (see reference (27)).

According to certain aspects, a "re-engineerable organism" is provided as a model system for biological discovery and in vivo screening. According to one aspect, a "re-engineerable mouse" bearing an inducible Cas9 transgene is provided, and localized delivery (using adeno-associated viruses, for example) of libraries of gRNAs targeting multiple genes or regulatory elements allow one to screen for mutations that result in the onset of tumors in the target tissue type. Use of Cas9 homologs or nuclease-null variants bearing effector domains (such as activators) allow one to multiplex activate or repress genes in vivo. According to this aspect, one could screen for factors that enable phenotypes such as: tissue-regeneration, trans-differentiation etc. According to certain aspects, (a) use of DNA-arrays enables multiplex synthesis of defined gRNA libraries (refer FIGS. 13A and 13B); and (b) gRNAs being small in size (refer FIG. 3b) are packaged and delivered using a multitude of non-viral or viral delivery methods.

According to one aspect, the lower toxicities observed with "nickases" for genome engineering applications is achieved by inactivating one of the Cas9 nuclease domains, either the nicking of the DNA strand base-paired with the RNA or nicking its complement. Inactivating both domains allows Cas9 to function as a retargetable DNA binding protein. According to one aspect, the Cas9 retargetable DNA binding protein is attached (a) to transcriptional activation or repression domains for modulating target gene expression, including but not limited to chromatin remodeling, histone modification, silencing, insulation, direct interactions with the transcriptional machinery;
(b) to nuclease domains such as FokI to enable 'highly specific' genome editing contingent upon dimerization of adjacent gRNA-Cas9 complexes;
(c) to fluorescent proteins for visualizing genomic loci and chromosome dynamics; or
(d) to other fluorescent molecules such as protein or nucleic acid bound organic fluorophores, quantum dots, molecular beacons and echo probes or molecular beacon replacements;
(e) to multivalent ligand-binding protein domains that enable programmable manipulation of genome-wide 3D architecture.

According to one aspect, the transcriptional activation and repression components can employ CRISPR systems naturally or synthetically orthogonal, such that the gRNAs only bind to the activator or repressor class of Cas. This allows a large set of gRNAs to tune multiple targets.

According to certain aspects, the use of gRNAs provide the ability to multiplex than mRNAs in part due to the smaller size—100 vs. 2000 nucleotide lengths respectively. This is particularly valuable when nucleic acid delivery is size limited, as in viral packaging. This enables multiple instances of cleavage, nicking, activation, or repression—or combinations thereof. The ability to easily target multiple regulatory targets allows the coarse-or-fine-tuning or regulatory networks without being constrained to the natural regulatory circuits downstream of specific regulatory factors (e.g. the 4 mRNAs used in reprogramming fibroblasts into IPSCs). Examples of multiplexing applications include:

1. Establishing (major and minor) histocompatibility alleles, haplotypes, and genotypes for human (or animal) tissue/organ transplantation. This aspect results e.g. in HLA homozygous cell lines or humanized animal breeds—or—a set of gRNAs capable of superimposing such HLA alleles onto an otherwise desirable cell lines or breeds.
2. Multiplex cis-regulatory element (CRE=signals for transcription, splicing, translation, RNA and protein folding, degradation, etc.) mutations in a single cell (or a collection of cells) can be used for efficiently studying the complex sets of regulatory interaction that can occur in normal development or pathological, synthetic or pharmaceutical scenarios. According to one aspect, the CREs are (or can be made) somewhat orthogonal (i.e. low cross talk) so that many can be tested in one setting—e.g. in an expensive animal embryo time series. One exemplary application is with RNA fluorescent in situ sequencing (FISSeq).
3. Multiplex combinations of CRE mutations and/or epigenetic activation or repression of CREs can be used to alter or reprogram iPSCs or ESCs or other stem cells or non-stem cells to any cell type or combination of cell types for use in organs-on-chips or other cell and organ cultures for purposes of testing pharmaceuticals (small molecules, proteins, RNAs, cells, animal, plant or microbial cells, aerosols and other delivery methods), transplantation strategies, personalization strategies, etc.
4. Making multiplex mutant human cells for use in diagnostic testing (and/or DNA sequencing) for medical genetics. To the extent that the chromosomal location and context of a human genome allele (or epigenetic mark) can influence the accuracy of a clinical genetic diagnosis, it is important to have alleles present in the correct location in a reference genome—rather than in an ectopic (aka transgenic) location or in a separate piece of synthetic DNA. One embodiment is a series of independent cell lines one per each diagnostic human SNP, or structural variant. Alternatively, one embodiment includes multiplex sets of alleles in the same cell. In some cases multiplex changes in one gene (or multiple genes) will be desirable under the assumption of independent testing. In other cases, particular haplotype combinations of alleles allows testing of sequencing (genotyping) methods which accurately establish haplotype phase (i.e. whether one or both copies of a gene are affected in an individual person or somatic cell type.
5. Repetitive elements or endogenous viral elements can be targeted with engineered Cas+gRNA systems in microbes, plants, animals, or human cells to reduce deleterious transposition or to aid in sequencing or other analytic genomic/transcriptomic/proteomic/diagnostic tools (in which nearly identical copies can be problematic).

The following references identified by number in the foregoing section are hereby incorporated by reference in their entireties.

1. B. Wiedenheft, S. H. Sternberg, J. A. Doudna, *Nature* 482, 331 (Feb. 16, 2012).
2. D. Bhaya, M. Davison, R. Barrangou, *Annual review of genetics* 45, 273 (2011).
3. M. P. Terns, R. M. Terns, *Current opinion in microbiology* 14, 321 (June, 2011).
4. M. Jinek et al., *Science* 337, 816 (Aug. 17, 2012).
5. G. Gasiunas, R. Barrangou, P. Horvath, V. Siksnys, *Proceedings of the National Academy of Sciences of the United States of America* 109, E2579 (Sep. 25, 2012).
6. R. Sapranauskas et al., *Nucleic acids research* 39, 9275 (November, 2011).
7. T. R. Brummelkamp, R. Bernards, R. Agami, *Science* 296, 550 (Apr. 19, 2002).
8. M. Miyagishi, K. Taira, *Nature biotechnology* 20, 497 (May, 2002).
9. E. Deltcheva et al., *Nature* 471, 602 (Mar. 31, 2011).
10. J. Zou, P. Mali, X. Huang, S. N. Dowey, L. Cheng, *Blood* 118, 4599 (Oct. 27, 2011).
11. N. E. Sanjana et al., *Nature protocols* 7, 171 (January, 2012).
12. J. H. Lee et al., *PLoS Genet* 5, e1000718 (November, 2009).
13. D. Hockemeyer et al., *Nature biotechnology* 27, 851 (September, 2009).
14. S. Kosuri et al., *Nature biotechnology* 28, 1295 (December, 2010).
15. V. Pattanayak, C. L. Ramirez, J. K. Joung, D. R. Liu, *Nature methods* 8, 765 (September, 2011).
16. N. M. King, O. Cohen-Haguenauer, *Molecular therapy: the journal of the American Society of Gene Therapy* 16, 432 (March, 2008).
17. Y. G. Kim, J. Cha, S. Chandrasegaran, *Proceedings of the National Academy of Sciences of the United States of America* 93, 1156 (Feb. 6, 1996).
18. E. J. Rebar, C. O. Pabo, *Science* 263, 671 (Feb. 4, 1994).
19. J. Boch et al., *Science* 326, 1509 (Dec. 11, 2009).
20. M. J. Moscou, A. J. Bogdanove, *Science* 326, 1501 (Dec. 11, 2009).
21. A. S. Khalil, J. J. Collins, *Nature reviews. Genetics* 11, 367 (May, 2010).
22. P. E. Purnick, R. Weiss, *Nature reviews. Molecular cell biology* 10, 410 (June, 2009).

23. J. Zou et al., *Cell stem cell* 5, 97 (Jul. 2, 2009).
24. N. Holt et al., *Nature biotechnology* 28, 839 (August, 2010).
25. F. D. Urnov et al., *Nature* 435, 646 (Jun. 2, 2005).
26. A. Lombardo et al., *Nature biotechnology* 25, 1298 (November, 2007).
27. H. Li et al., *Nature* 475, 217 (Jul. 14, 2011).

The following examples are set forth as being representative of the present disclosure. These examples are not to be construed as limiting the scope of the present disclosure as these and other equivalent embodiments will be apparent in view of the present disclosure, figures and accompanying claims.

Example I

The Type II CRISPR-Cas System

According to one aspect, embodiments of the present disclosure utilize short RNA to identify foreign nucleic acids for activity by a nuclease in a eukaryotic cell. According to a certain aspect of the present disclosure, a eukaryotic cell is altered to include within its genome nucleic acids encoding one or more short RNA and one or more nucleases which are activated by the binding of a short RNA to a target DNA sequence. According to certain aspects, exemplary short RNA/enzyme systems may be identified within bacteria or archaea, such as (CRISPR)/CRISPR-associated (Cas) systems that use short RNA to direct degradation of foreign nucleic acids. CRISPR ("clustered regularly interspaced short palindromic repeats") defense involves acquisition and integration of new targeting "spacers" from invading virus or plasmid DNA into the CRISPR locus, expression and processing of short guiding CRISPR RNAs (crRNAs) consisting of spacer-repeat units, and cleavage of nucleic acids (most commonly DNA) complementary to the spacer.

Three classes of CRISPR systems are generally known and are referred to as Type I, Type II or Type III). According to one aspect, a particular useful enzyme according to the present disclosure to cleave dsDNA is the single effector enzyme, Cas9, common to Type II. (See reference (1)). Within bacteria, the Type II effector system consists of a long pre-crRNA transcribed from the spacer-containing CRISPR locus, the multifunctional Cas9 protein, and a tracrRNA important for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. According to one aspect, eukaryotic cells of the present disclosure are engineered to avoid use of RNase III and the crRNA processing in general. See reference (2).

According to one aspect, the enzyme of the present disclosure, such as Cas9 unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain aspects, different protospacer-adjacent motif can be utilized. For example, the *S. pyogenes* system requires an NGG sequence, where N can be any nucleotide. *S. thermophilus* Type II systems require NGGNG (see reference (3)) and NNAGAAW (see reference (4)), respectively, while different *S. mutans* systems tolerate NGG or NAAR (see reference (5)). Bioinformatic analyses have generated extensive databases of CRISPR loci in a variety of bacteria that may serve to identify additional useful PAMs and expand the set of CRISPR-targetable sequences (see references (6, 7)). In *S. thermophilus*, Cas9 generates a blunt-ended double-stranded break 3 bp prior to the 3' end of the protospacer (see reference (8)), a process mediated by two catalytic domains in the Cas9 protein: an HNH domain that cleaves the complementary strand of the DNA and a RuvC-like domain that cleaves the non-complementary strand (See FIG. 1A and FIGS. 3A-1 and 3A-2). While the *S. pyogenes* system has not been characterized to the same level of precision, DSB formation also occurs towards the 3' end of the protospacer. If one of the two nuclease domains is inactivated, Cas9 will function as a nickase in vitro (see reference (2)) and in human cells (see FIG. 5).

According to one aspect, the specificity of gRNA-directed Cas9 cleavage is used as a mechanism for genome engineering in a eukaryotic cell. According to one aspect, hybridization of the gRNA need not be 100 percent in order for the enzyme to recognize the gRNA/DNA hybrid and affect cleavage. Some off-target activity could occur. For example, the *S. pyogenes* system tolerates mismatches in the first 6 bases out of the 20 bp mature spacer sequence in vitro. According to one aspect, greater stringency may be beneficial in vivo when potential off-target sites matching (last 14 bp) NGG exist within the human reference genome for the gRNAs. The effect of mismatches and enzyme activity in general are described in references (9), (2), (10), and (4).

According to certain aspects, specificity may be improved. When interference is sensitive to the melting temperature of the gRNA-DNA hybrid, AT-rich target sequences may have fewer off-target sites. Carefully choosing target sites to avoid pseudo-sites with at least 14 bp matching sequences elsewhere in the genome may improve specificity. The use of a Cas9 variant requiring a longer PAM sequence may reduce the frequency of off-target sites. Directed evolution may improve Cas9 specificity to a level sufficient to completely preclude off-target activity, ideally requiring a perfect 20 bp gRNA match with a minimal PAM. Accordingly, modification to the Cas9 protein is a representative embodiment of the present disclosure. As such, novel methods permitting many rounds of evolution in a short timeframe (see reference (11) and envisioned. CRISPR systems useful in the present disclosure are described in references (12, 13).

Example II

Plasmid Construction

The Cas9 gene sequence was human codon optimized and assembled by hierarchical fusion PCR assembly of 9 500 bp gBlocks ordered from IDT. FIGS. 3A-1 and 3A-2 for the engineered type II CRISPR system for human cells shows the expression format and full sequence of the cas9 gene insert. The RuvC-like and HNH motifs, and the C-terminus SV40 NLS are respectively highlighted by blue, brown and orange colors. Cas9_D10A was similarly constructed. The resulting full-length products were cloned into the pcDNA3.3-TOPO vector (Invitrogen). The target gRNA expression constructs were directly ordered as individual 455 bp gBlocks from IDT and either cloned into the pCR-BluntII-TOPO vector (Invitrogen) or per amplified. FIG. 3B shows the U6 promoter based expression scheme for the guide RNAs and predicted RNA transcript secondary structure. The use of the U6 promoter constrains the $1^{st}$ position in the RNA transcript to be a 'G' and thus all genomic sites of the form GN$_{20}$GG can be targeted using this approach. FIG. 3C shows the 7 gRNAs used.

The vectors for the HR reporter assay involving a broken GFP were constructed by fusion PCR assembly of the GFP sequence bearing the stop codon and 68 bp AAVS1 fragment (or mutants thereof; see FIGS. 6A and 6B), or 58 bp fragments from the DNMT3a and DNMT3b genomic loci (see FIG. 8A) assembled into the EGIP lentivector from Addgene (plasmid #26777). These lentivectors were then used to establish the GFP reporter stable lines. TALENs used in this study were constructed using the protocols described in (14). All DNA reagents developed in this study are available at Addgene.

Example III

Cell Culture

PGP1 iPS cells were maintained on Matrigel (BD Biosciences)-coated plates in mTeSR1 (Stemcell Technologies). Cultures were passaged every 5-7 d with TrypLE Express (Invitrogen). K562 cells were grown and maintained in RPMI (Invitrogen) containing 15% FBS. HEK 293T cells were cultured in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). All cells were maintained at 37° C. and 5% CO$_2$ in a humidified incubator.

Example IV

Gene Targeting of PGP1 iPS, K562 and 293Ts

PGP1 iPS cells were cultured in Rho kinase (ROCK) inhibitor (Calbiochem) 2 h before nucleofection. Cells were harvest using TrypLE Express (Invitrogen) and 2×10$^6$ cells were resuspended in P3 reagent (Lonza) with 1 µg Cas9 plasmid, 1 µg gRNA and/or 1 µg DNA donor plasmid, and nucleofected according to manufacturer's instruction (Lonza). Cells were subsequently plated on an mTeSR1-coated plate in mTeSR1 medium supplemented with ROCK inhibitor for the first 24 h. For K562s, 2×10$^6$ cells were resuspended in SF reagent (Lonza) with 1 µg Cas9 plasmid, 1 µg gRNA and/or 1 µg DNA donor plasmid, and nucleofected according to manufacturer's instruction (Lonza). For 293Ts, 0.1×10$^6$ cells were transfected with 1 µg Cas9 plasmid, 1 µg gRNA and/or 1 µg DNA donor plasmid using Lipofectamine 2000 as per the manufacturer's protocols. The DNA donors used for endogenous AAVS1 targeting were either a dsDNA donor (FIG. 2C) or a 90mer oligonucleotide. The former has flanking short homology arms and a SA-2A-puromycin-CaGGS-eGFP cassette to enrich for successfully targeted cells.

The targeting efficiency was assessed as follows. Cells were harvested 3 days after nucleofection and the genomic DNA of ~1×10$^6$ cells was extracted using prepGEM (ZyGEM). PCR was conducted to amplify the targeting region with genomic DNA derived from the cells and amplicons were deep sequenced by MiSeq Personal Sequencer (Illumina) with coverage>200,000 reads. The sequencing data was analyzed to estimate NHEJ efficiencies. The reference AAVS1 sequence analyzed is:

(SEQ ID NO: 1)
CACTTCAGGACAGCATGTTTGCTGCCTCCAGGGATCCTGTGTCCCCGAGC

TGGGACCACCTTATATTCCCAGGGCCGGTTAATGTGGCTCTGGTTCTGGG

TACTTTTATCTGTCCCCTCCACCCCACAGTGGGGCCACTAGGGACAGGAT

TGGTGACAGAAAAGCCCCATCCTTAGGCCTCCTCCTTCCTAGTCTCCTGA

TATTGGGTCTAACCCCCACCTCCTGTTAGGCAGATTCCTTATCTGGTGAC

ACACCCCCATTTCCTGGA

The PCR primers for amplifying the targeting regions in the human genome are:

AAVS1-R
(SEQ ID NO: 2)
CTCGGCATTCCTGCTGAACCGCTCTTCCGATCTacaggaggtgggggtta gac

AAVS1-F.1
(SEQ ID NO: 3)
ACACTCTTTCCCTACACGACGCTCTTCCGATCTCGTGATtatattcccag ggccggtta AAVS1-F.2
(SEQ ID NO: 4)
ACACTCTTTCCCTACACGACGCTCTTCCGATCTACATCGtatattcccag ggccggtta AAVS1-F.3
(SEQ ID NO: 5)
ACACTCTTTCCCTACACGACGCTCTTCCGATCTGCCTAAtatattcccag ggccggtta AAVS1-F.4
(SEQ ID NO: 6)
ACACTCTTTCCCTACACGACGCTCTTCCGATCTTGGTCAtatattcccag ggccggtta AAVS1-F.5
(SEQ ID NO: 7)
ACACTCTTTCCCTACACGACGCTCTTCCGATCTCACTGTtatattcccag ggccggtta AAVS1-F.6
(SEQ ID NO: 8)
ACACTCTTTCCCTACACGACGCTCTTCCGATCTATTGGCtatattcccag ggccggtta AAVS1-F.7
(SEQ ID NO: 9)
ACACTCTTTCCCTACACGACGCTCTTCCGATCTGATCTGtatattcccag ggccggtta AAVS1-F.8
(SEQ ID NO: 10)
ACACTCTTTCCCTACACGACGCTCTTCCGATCTTCAAGTtatattcccag ggccggtta AAVS1-F.9
(SEQ ID NO: 11)
ACACTCTTTCCCTACACGACGCTCTTCCGATCTCTGATCtatattcccag ggccggtta AAVS1-F.10
(SEQ ID NO: 12)
ACACTCTTTCCCTACACGACGCTCTTCCGATCTAAGCTAtatattcccag ggccggtta -continued AAVS1-F.11
(SEQ ID NO: 13)
ACACTCTTTCCCTACACGACGCTCTTCCGATCTGTAGCCtatattcccag ggccggtta AAVS1-F.12
(SEQ ID NO: 14)
ACACTCTTTCCCTACACGACGCTCTTCCGATCTTACAAGtatattcccag ggccggtta To analyze the HR events using the DNA donor in FIG. 2C, the primers used were:

```
HR_AAVS1-F
                                         (SEQ ID NO: 15)
CTGCCGTCTCTCTCCTGAGT

HR_Puro-R
                                         (SEQ ID NO: 16)
GTGGGCTTGTACTCGGTCAT
```

Example V

Bioinformatics Approach for Computing Human Exon CRISPR Targets and Methodology for their Multiplexed Synthesis A set of gRNA gene sequences that maximally target specific locations in human exons but minimally target other locations in the genome were determined as follows. According to one aspect, maximally efficient targeting by a gRNA is achieved by 23 nt sequences, the 5'-most 20 nt of which exactly complement a desired location, while the three 3'-most bases must be of the form NGG. Additionally, the 5'-most nt must be a G to establish a pol-III transcription start site. However, according to (2), mispairing of the six 5'-most nt of a 20 bp gRNA against its genomic target does not abrogate Cas9-mediated cleavage so long as the last 14 nt pairs properly, but mispairing of the eight 5'-most nt along with pairing of the last 12 nt does, while the case of the seven 5-most nt mispairs and 13 3' pairs was not tested. To be conservative regarding off-target effects, one condition was that the case of the seven 5'-most mispairs is, like the case of six, permissive of cleavage, so that pairing of the 3'-most 13 nt is sufficient for cleavage. To identify CRISPR target sites within human exons that should be cleavable without off-target cuts, all 23 bp sequences of the form 5'-GBBBB BBBBB BBBBB BBBBB NGG-3' (form 1) were examined, where the B's represent the bases at the exon location, for which no sequence of the form 5'-NNNNN NNBBB BBBBB BBBBB NGG-3' (form 2) existed at any other location in the human genome. Specifically, (i) a BED file of locations of coding regions of all RefSeq genes the GRCh37/hg19 human genome from the UCSC Genome Browser (15-17) was downloaded. Coding exon locations in this BED file comprised a set of 346089 mappings of RefSeq mRNA accessions to the hg19 genome. However, some RefSeq mRNA accessions mapped to multiple genomic locations (probable gene duplications), and many accessions mapped to subsets of the same set of exon locations (multiple isoforms of the same genes). To distinguish apparently duplicated gene instances and consolidate multiple references to the same genomic exon instance by multiple RefSeq isoform accessions, (ii) unique numerical suffixes to 705 RefSeq accession numbers that had multiple genomic locations were added, and (iii) the mergeBed function of BEDTools (18) (v2.16.2-zip-87e3926) was used to consolidate overlapping exon locations into merged exon regions. These steps reduced the initial set of 346089 RefSeq exon locations to 192783 distinct genomic regions. The hg19 sequence for all merged exon regions were downloaded using the UCSC Table Browser, adding 20 bp of padding on each end. (iv) Using custom perl code, 1657793 instances of form 1 were identified within this exonic sequence. (v) These sequences were then filtered for the existence of off-target occurrences of form 2: For each merged exon form 1 target, the 3'-most 13 bp specific (B) "core" sequences were extracted and, for each core generated the four 16 bp sequences 5'-BBB BBBBB BBBBB NGG-3' (N=A, C, G, and T), and searched the entire hg19 genome for exact matches to these 6631172 sequences using Bowtie version 0.12.8 (19) using the parameters -l 16 -v 0 -k 2. Any exon target site for which there was more than a single match was rejected. Note that because any specific 13 bp core sequence followed by the sequence NGG confers only 15 bp of specificity, there should be on average ~5.6 matches to an extended core sequence in a random ~3 Gb sequence (both strands). Therefore, most of the 1657793 initially identified targets were rejected; however 189864 sequences passed this filter. These comprise the set of CRISPR-targetable exonic locations in the human genome. The 189864 sequences target locations in 78028 merged exonic regions (~40.5% of the total of 192783 merged human exon regions) at a multiplicity of ~2.4 sites per targeted exonic region. To assess targeting at a gene level, RefSeq mRNA mappings were clustered so that any two RefSeq accessions (including the gene duplicates distinguished in (ii)) that overlap a merged exon region are counted as a single gene cluster, the 189864 exonic specific CRISPR sites target 17104 out of 18872 gene clusters (~90.6% of all gene clusters) at a multiplicity of ~11.1 per targeted gene cluster. (Note that while these gene clusters collapse RefSeq mRNA accessions that represent multiple isoforms of a single transcribed gene into a single entity, they will also collapse overlapping distinct genes as well as genes with antisense transcripts.) At the level of original RefSeq accessions, the 189864 sequences targeted exonic regions in 30563 out of a total of 43726 (~69.9%) mapped RefSeq accessions (including distinguished gene duplicates) at a multiplicity of ~6.2 sites per targeted mapped RefSeq accession.

According to one aspect, the database can be refined by correlating performance with factors, such as base composition and secondary structure of both gRNAs and genomic targets (20, 21), and the epigenetic state of these targets in human cell lines for which this information is available (22).

Example VI

Multiplex Synthesis

The target sequences were incorporated into a 200 bp format that is compatible for multiplex synthesis on DNA arrays (23, 24). According to one aspect the method allows for targeted retrieval of a specific or pools of gRNA sequences from the DNA array based oligonucleotide pool and its rapid cloning into a common expression vector (FIGS. 13A-1 and 13A-2). Specifically, a 12 k oligonucleotide pool from CustomArray Inc. was synthesized. Furthermore, gRNAs of choice from this library (FIG. 13B) were successfully retrieved. We observed an error rate of ~4 mutations per 1000 bp of synthesized DNA.

Example VII

RNA-Guided Genome Editing Requires Both Cas9 and Guide RNA for Successful Targeting Using the GFP reporter assay described in FIG. 1B, all possible combinations of the repair DNA donor, Cas9 protein, and gRNA were tested for their ability to effect successful HR (in 293Ts). As shown in FIG. 4, GFP+ cells were observed only when all the 3 components were present, validating that these CRISPR components are essential for RNA-guided genome editing. Data is mean+/−SEM (N=3).

Example VIII

Analysis of gRNA and Cas9 Mediated Genome Editing

Figure 5A:
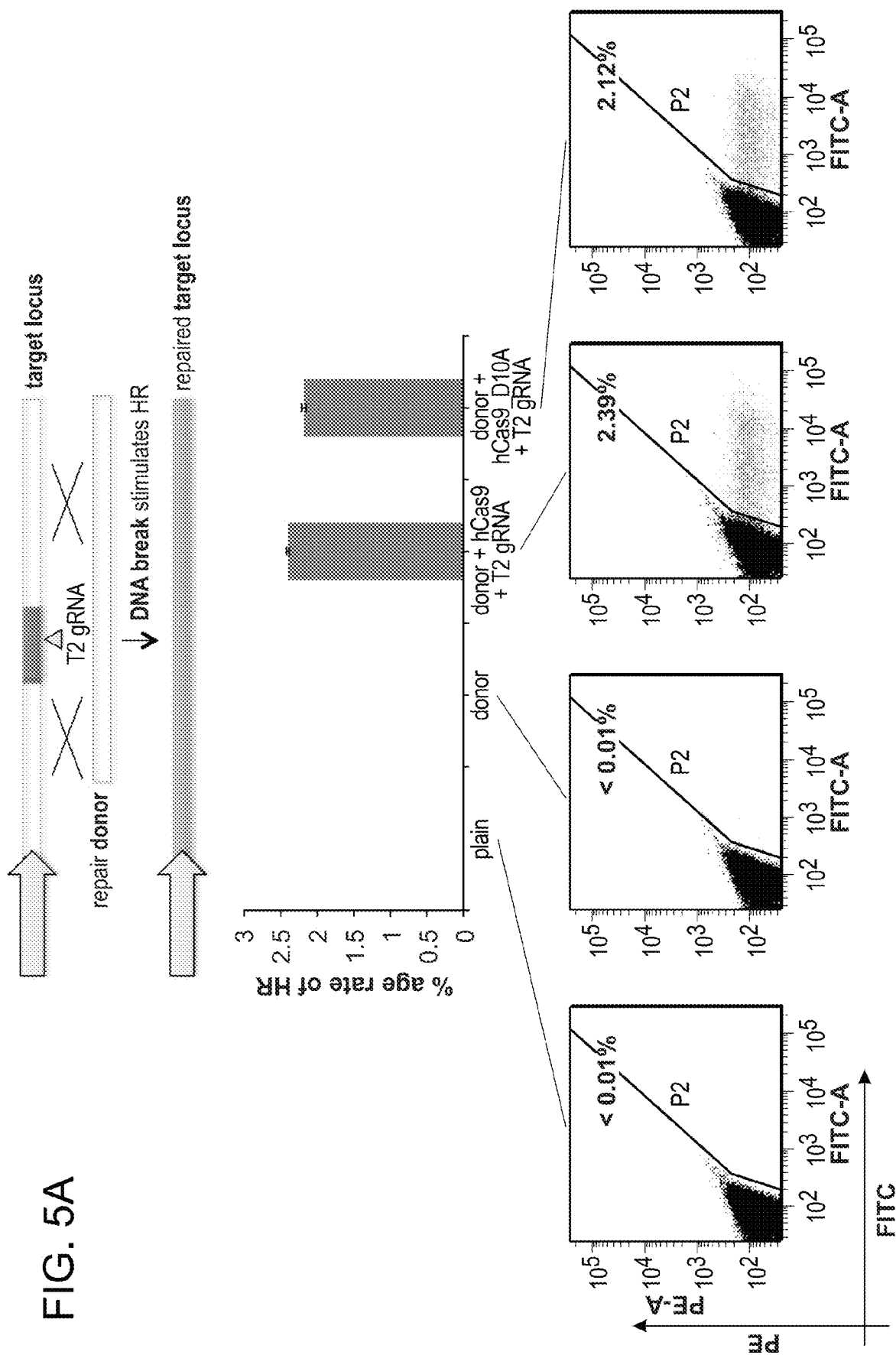
FIG. 5A-5B depict the analysis of gRNA and Cas9 mediated genome editing (SEQ ID NO:19).
Figure 5B:
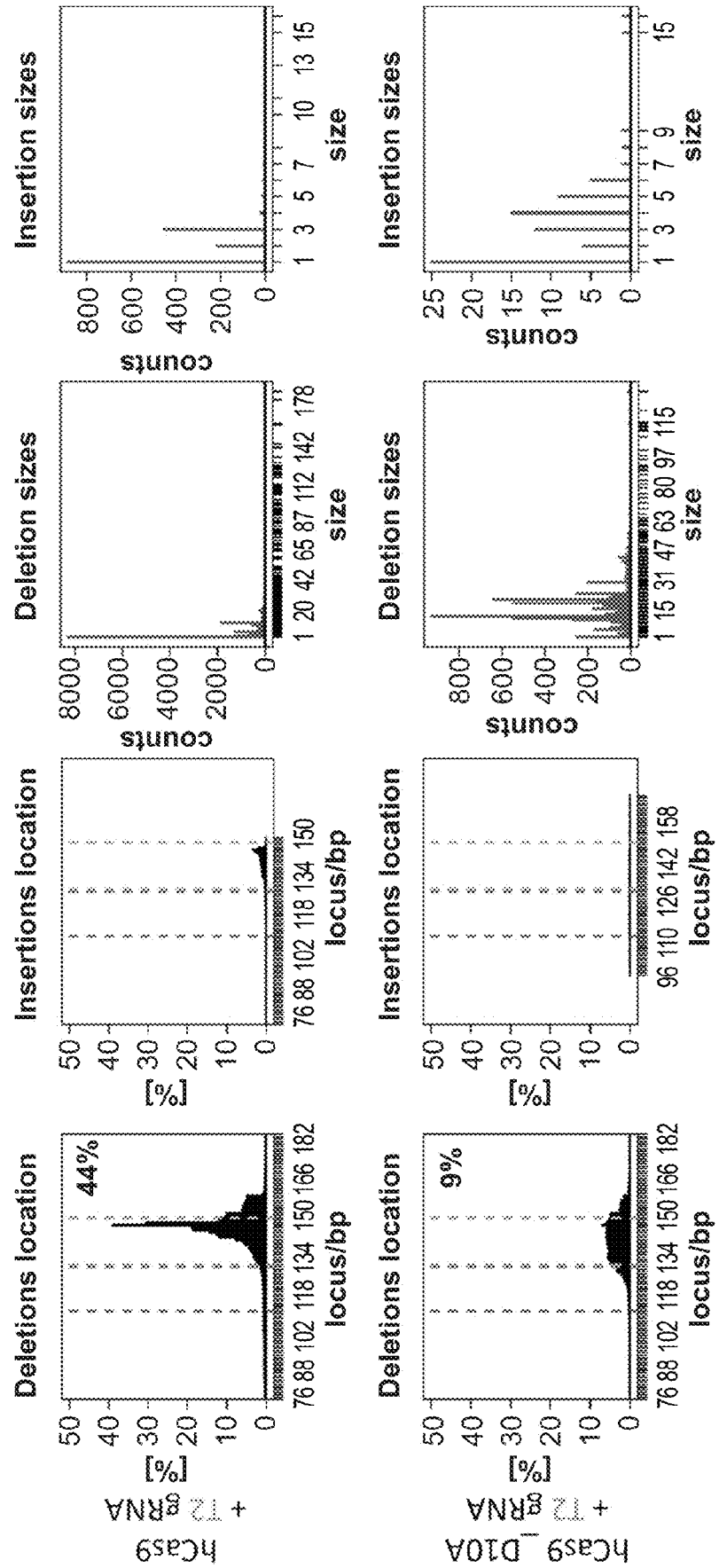

The CRISPR mediated genome editing process was examined using either (A) a GFP reporter assay as described earlier results of which are shown in FIG. 5A, and (B) deep sequencing of the targeted loci (in 293Ts), results of which are shown in FIG. 5B. As comparison, a D10A mutant for Cas9 was tested that has been shown in earlier reports to function as a nickase in in vitro assays. As shown in FIG. 5, both Cas9 and Cas9D10A can effect successful HR at nearly similar rates. Deep sequencing however confirms that while Cas9 shows robust NHEJ at the targeted loci, the D10A mutant has significantly diminished NHEJ rates (as would be expected from its putative ability to only nick DNA). Also, consistent with the known biochemistry of the Cas9 protein, NHEJ data confirms that most base-pair deletions or insertions occurred near the 3' end of the target sequence: the peak is ~3-4 bases upstream of the PAM site, with a median deletion frequency of ~9-10 bp. Data is mean+/−SEM (N=3).

Example IX

RNA-Guided Genome Editing is Target Sequence Specific

Figures 2, 2B, 3:
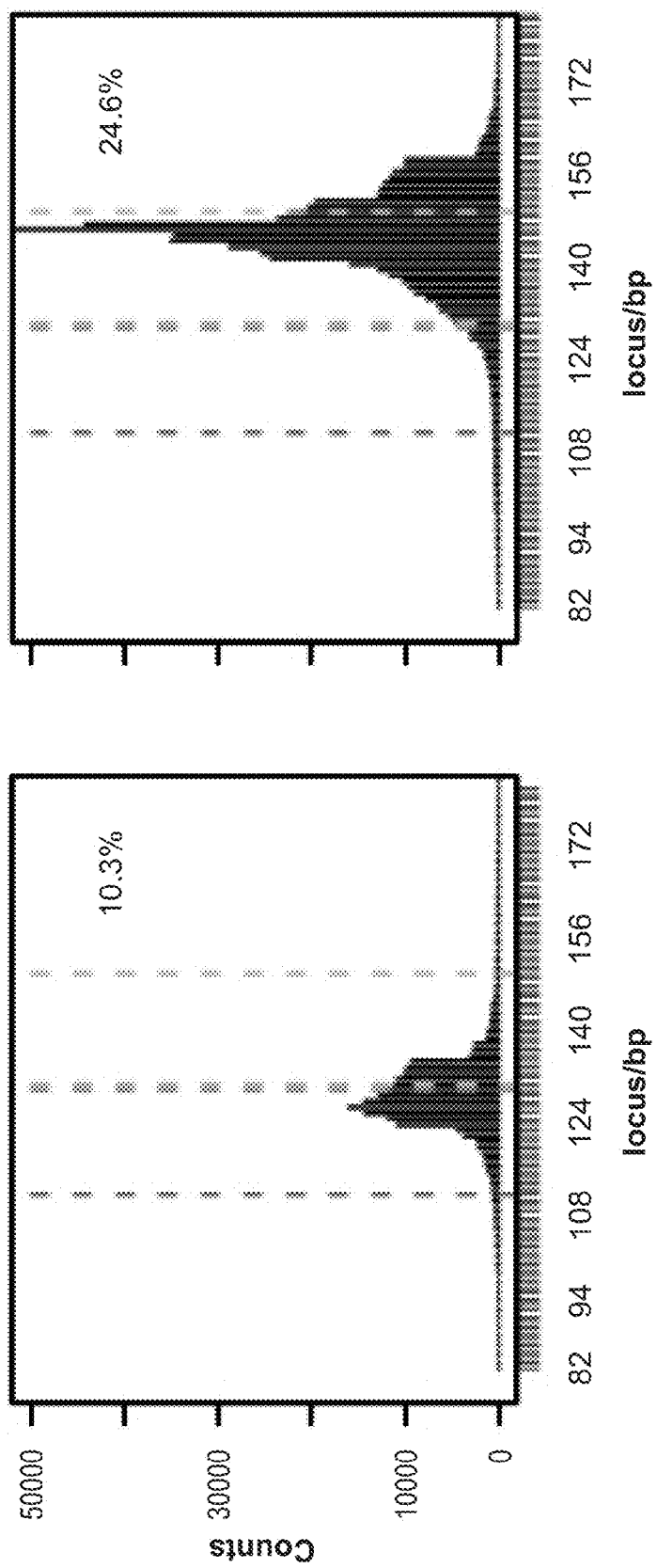
Figure 2D:
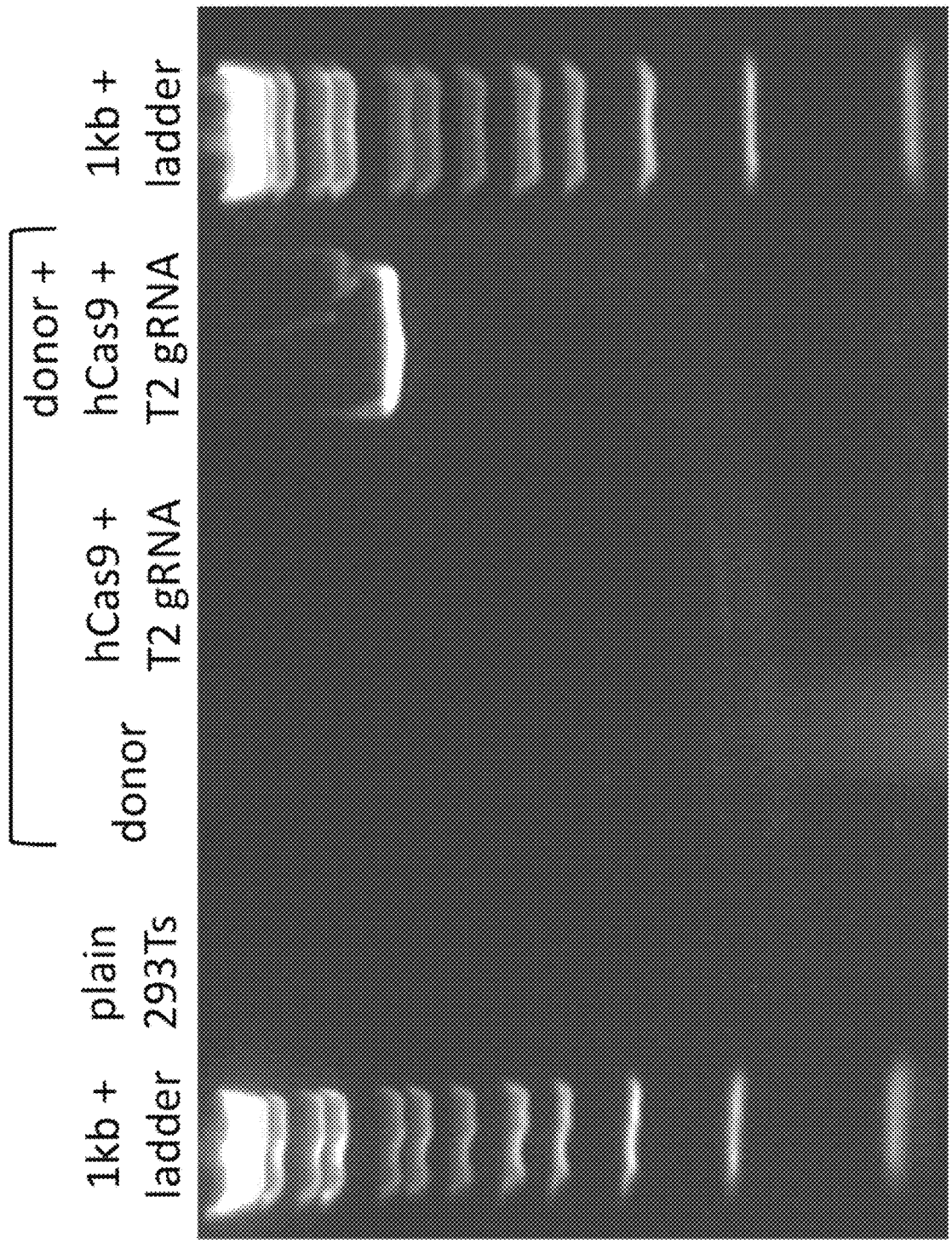
FIG. 2D depicts PCR assay three days post transfection.
Figure 2E:
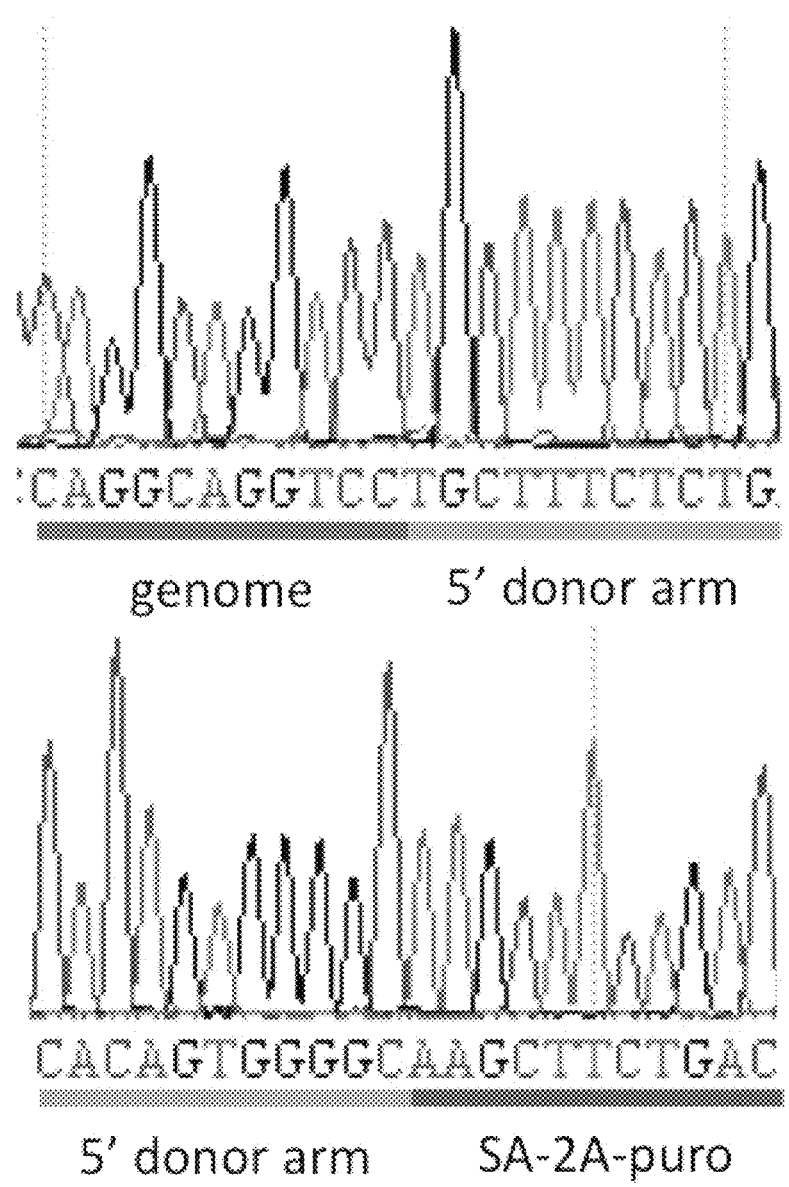
FIG. 2E depicts successful HR confirmed by Sanger sequencing of the PCR amplicon (SEQ ID NOs:20-21).
Figure 2F:
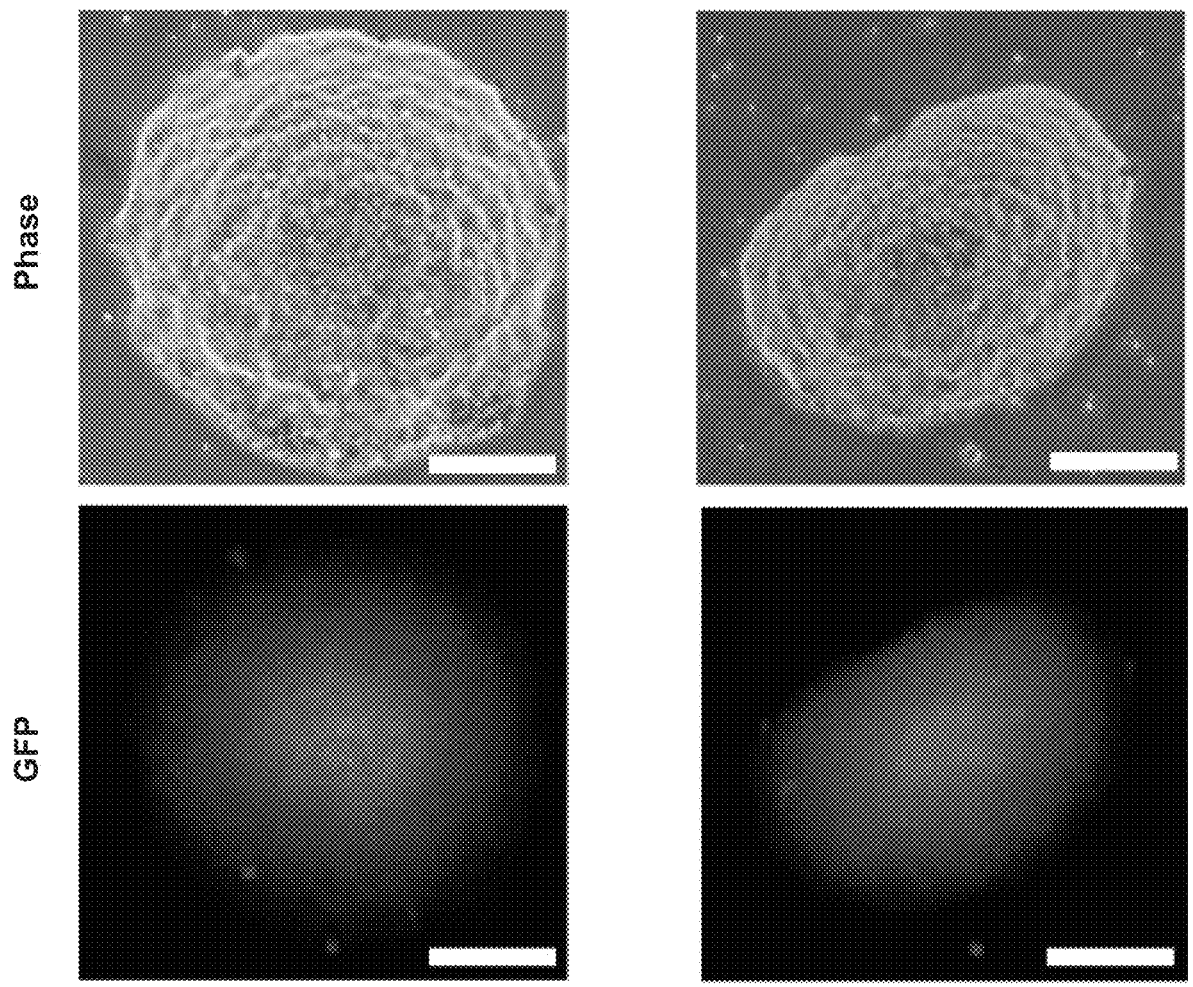
FIG. 2F depicts images of targeted clones of 293T cells.
Figures 1, 3A:
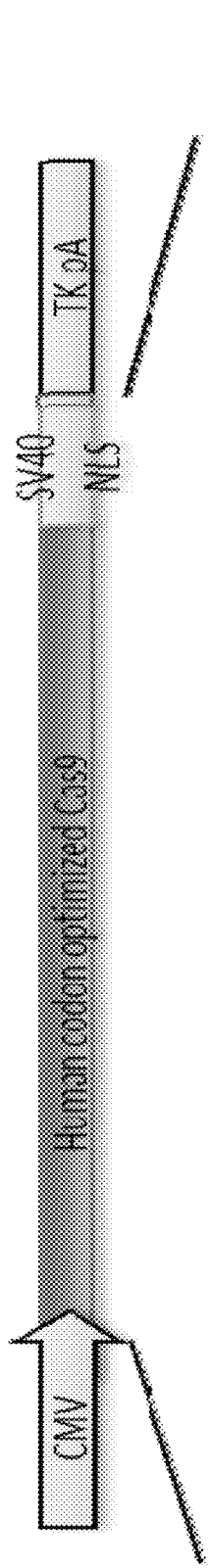

Similar to the GFP reporter assay described in FIG. 1B, 3 293T stable lines each bearing a distinct GFP reporter construct were developed. These are distinguished by the sequence of the AAVS1 fragment insert (as indicated in the FIGS. 6A and 6B). One line harbored the wild-type fragment while the two other lines were mutated at 6 bp (highlighted in red). Each of the lines was then targeted by one of the following 4 reagents: a GFP-ZFN pair that can target all cell types since its targeted sequence was in the flanking GFP fragments and hence present in along cell lines; a AAVS1 TALEN that could potentially target only the wt-AAVS1 fragment since the mutations in the other two lines should render the left TALEN unable to bind their sites; the T1 gRNA which can also potentially target only the wt-AAVS1 fragment, since its target site is also disrupted in the two mutant lines; and finally the T2 gRNA which should be able to target all 3 cell lines since, unlike the T1 gRNA, its target site is unaltered among the 3 lines. ZFN modified all 3 cell types, the AAVS1 TALENs and the T1 gRNA only targeted the wt-AAVS1 cell type, and the T2 gRNA successfully targets all 3 cell types. These results together confirm that the guide RNA mediated editing is target sequence specific. Data is mean+/−SEM (N=3).

Example X

Guide RNAs Targeted to the GFP Sequence Enable Robust Genome Editing

In addition to the 2 gRNAs targeting the AAVS1 insert, two additional gRNAs targeting the flanking GFP sequences of the reporter described in FIG. 1B (in 293Ts) were tested. As shown in FIG. 7, these gRNAs were also able to effect robust HR at this engineered locus. Data is mean+/−SEM (N=3).

Example XI

Figure 8B:
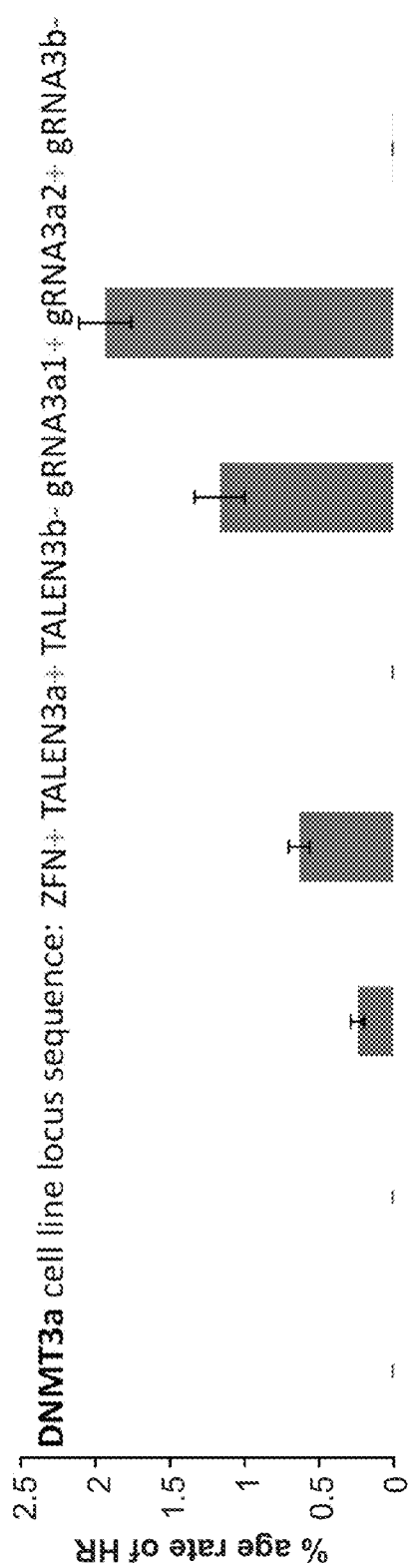

RNA-Guided Genome Editing is Target Sequence Specific, and Demonstrates Similar Targeting Efficiencies as ZFNs or TALENs Similar to the GFP reporter assay described in FIG. 1B, two 293T stable lines each bearing a distinct GFP reporter construct were developed. These are distinguished by the sequence of the fragment insert (as indicated in FIG. 8A). One line harbored a 58 bp fragment from the DNMT3a gene while the other line bore a homologous 58 bp fragment from the DNMT3b gene. The sequence differences are highlighted in red. Each of the lines was then targeted by one of the following 6 reagents: a GFP-ZFN pair that can target all cell types since its targeted sequence was in the flanking GFP fragments and hence present in along cell lines; a pair of TALENs that potentially target either DNMT3a or DNMT3b fragments; a pair of gRNAs that can potentially target only the DNMT3a fragment; and finally a gRNA that should potentially only target the DNMT3b fragment. As indicated in FIG. 8B, the ZFN modified all 3 cell types, and the TALENs and gRNAs only their respective targets. Furthermore the efficiencies of targeting were comparable across the 6 targeting reagents. These results together confirm that RNA-guided editing is target sequence specific and demonstrates similar targeting efficiencies as ZFNs or TALENs. Data is mean+/−SEM (N=3).

Example XII

RNA-Guided NHEJ in Human iPS Cells

Human iPS cells (PGP1) were nucleofected with constructs indicated in the left panel of FIGS. 9A, 9B, and 9C. 4 days after nucleofection, NHEJ rate was measured by assessing genomic deletion and insertion rate at double-strand breaks (DSBs) by deep sequencing. Panel 1: Deletion rate detected at targeting region. Red dash lines: boundary of T1 RNA targeting site; green dash lines: boundary of T2 RNA targeting site. The deletion incidence at each nucleotide position was plotted in black lines and the deletion rate as the percentage of reads carrying deletions was calculated. Panel 2: Insertion rate detected at targeting region. Red dash lines: boundary of T1 RNA targeting site; green dash lines: boundary of T2 RNA targeting site. The incidence of insertion at the genomic location where the first insertion junction was detected was plotted in black lines and the insertion rate as the percentage of reads carrying insertions was calculated. Panel 3: Deletion size distribution. The frequencies of different size deletions among the whole NHEJ population was plotted. Panel 4: insertion size distribution. The frequencies of different sizes insertions among the whole NHEJ population was plotted. iPS targeting by both gRNAs is efficient (2-4%), sequence specific (as shown by the shift in position of the NHEJ deletion distributions), and reaffirming the results of FIG. 4, the NGS-based analysis also shows that both the Cas9 protein and the gRNA are essential for NHEJ events at the target locus.

Example XIII

RNA-Guided NHEJ in K562 Cells

Figure 10A:
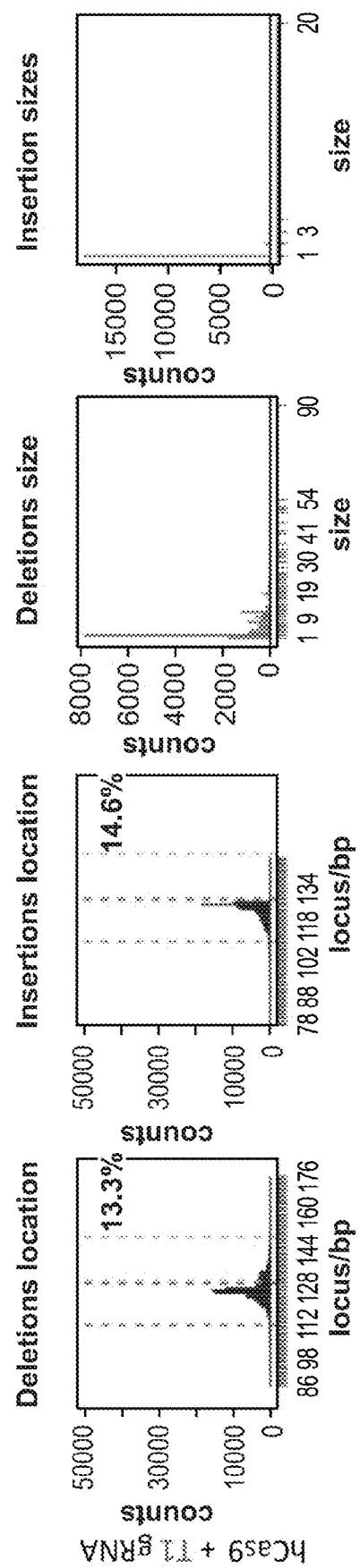
FIGS. 10A-10B depict RNA-guided NHEJ in K562 cells (SEQ ID NO:19).
Figure 10B:
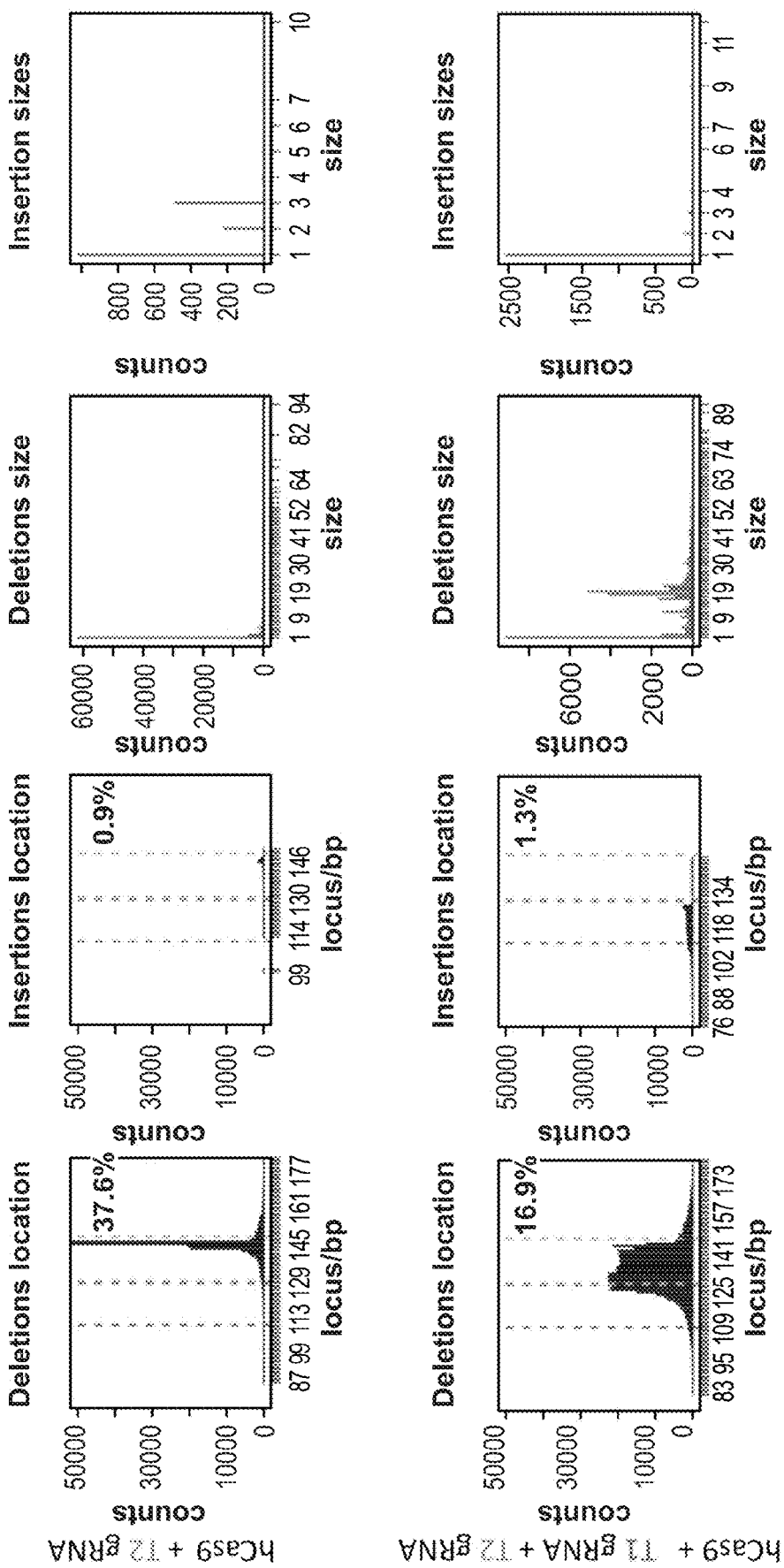

K562 cells were nucleated with constructs indicated in the left panel of FIGS. 10A and 10B. 4 days after nucleofection, NHEJ rate was measured by assessing genomic deletion and insertion rate at DSBs by deep sequencing. Panel 1: Deletion rate detected at targeting region. Red dash lines: boundary of T1 RNA targeting site; green dash lines: boundary of T2 RNA targeting site. The deletion incidence at each nucleotide position was plotted in black lines and the deletion rate as the percentage of reads carrying deletions was calculated. Panel 2: Insertion rate detected at targeting region. Red dash lines: boundary of T1 RNA targeting site; green dash lines: boundary of T2 RNA targeting site. The incidence of insertion at the genomic location where the first insertion junction was detected was plotted in black lines and the insertion rate as the percentage of reads carrying insertions was calculated. Panel 3: Deletion size distribution. The frequencies of different size deletions among the whole NHEJ population was plotted. Panel 4: insertion size distribution. The frequencies of different sizes insertions among the whole NHEJ population was plotted. K562 targeting by both gRNAs is efficient (13-38%) and sequence specific (as shown by the shift in position of the NHEJ deletion distributions). Importantly, as evidenced by the peaks in the histogram of observed frequencies of deletion sizes, simultaneous introduction of both T1 and T2 guide RNAs resulted in high efficiency deletion of the intervening 19 bp fragment, demonstrating that multiplexed editing of genomic loci is also feasible using this approach.

Example XIV

Figure 11B:
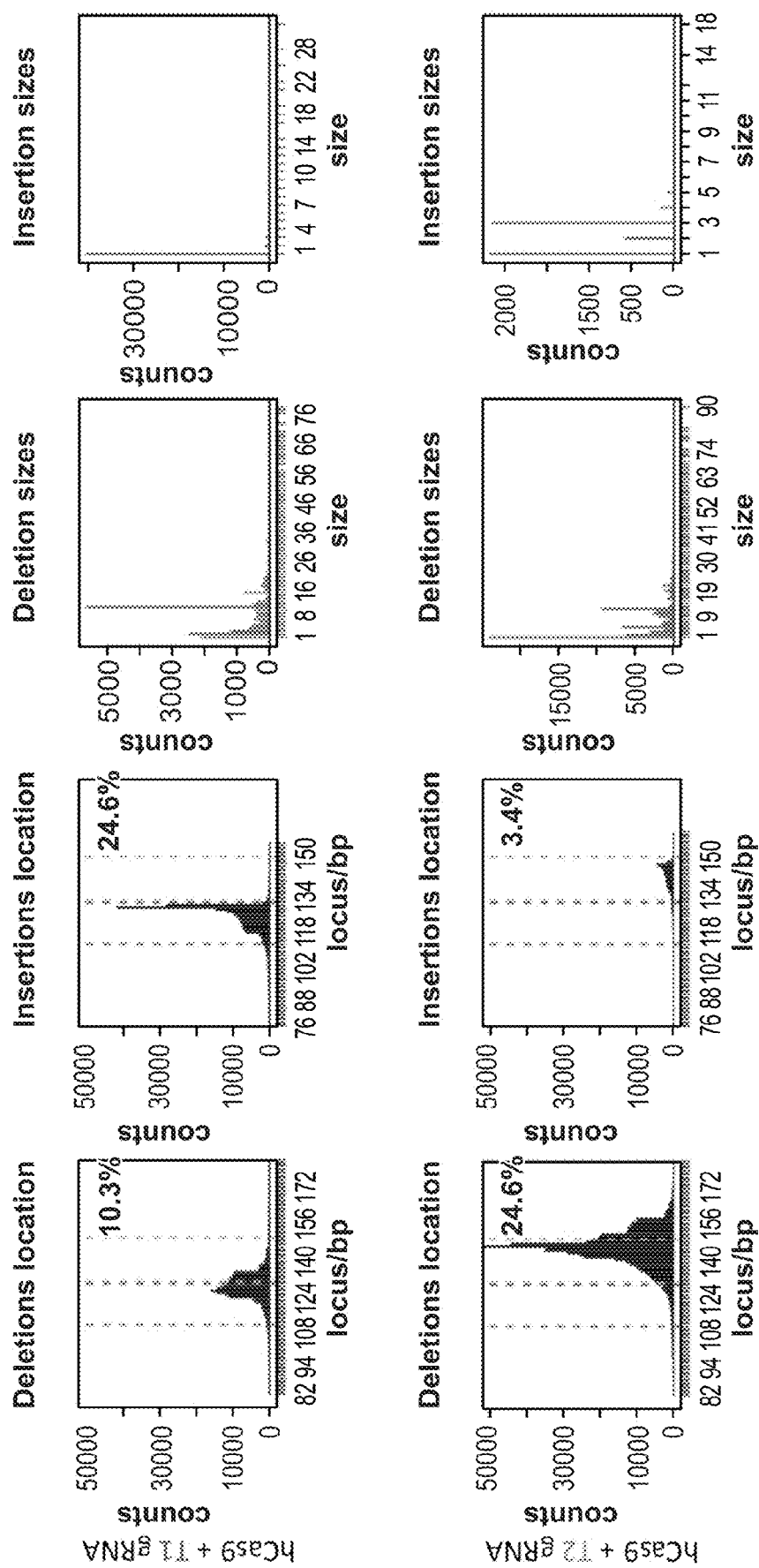

RNA-Guided NHEJ in 293T Cells 293T cells were transfected with constructs indicated in the left panel of FIGS. 11A and 11B. 4 days after nucleofection, NHEJ rate was measured by assessing genomic deletion and insertion rate at DSBs by deep sequencing. Panel 1: Deletion rate detected at targeting region. Red dash lines: boundary of T1 RNA targeting site; green dash lines: boundary of T2 RNA targeting site. The deletion incidence at each nucleotide position was plotted in black lines and the deletion rate as the percentage of reads carrying deletions was calculated. Panel 2: Insertion rate detected at targeting region. Red dash lines: boundary of T1 RNA targeting site; green dash lines: boundary of T2 RNA targeting site. The incidence of insertion at the genomic location where the first insertion junction was detected was plotted in black lines and the insertion rate as the percentage of reads carrying insertions was calculated. Panel 3: Deletion size distribution. The frequencies of different size deletions among the whole NHEJ population was plotted. Panel 4: insertion size distribution. The frequencies of different sizes insertions among the whole NHEJ population was plotted. 293T targeting by both gRNAs is efficient (10-24%) and sequence specific (as shown by the shift in position of the NHEJ deletion distributions).

Example XV

HR at the Endogenous AAVS1 Locus Using Either a dsDNA Donor or a Short Oligonucleotide Donor As shown in FIG. 12A, PCR screen (with reference to FIG. 2C) confirmed that 21/24 randomly picked 293T clones were successfully targeted. As shown in FIG. 12B, similar PCR screen confirmed 3/7 randomly picked PGP1-iPS clones were also successfully targeted. As shown in FIG. 12C, short 90mer oligos could also effect robust targeting at the endogenous AAVS1 locus (shown here for K562 cells).

Example XVI

Figure 13B:
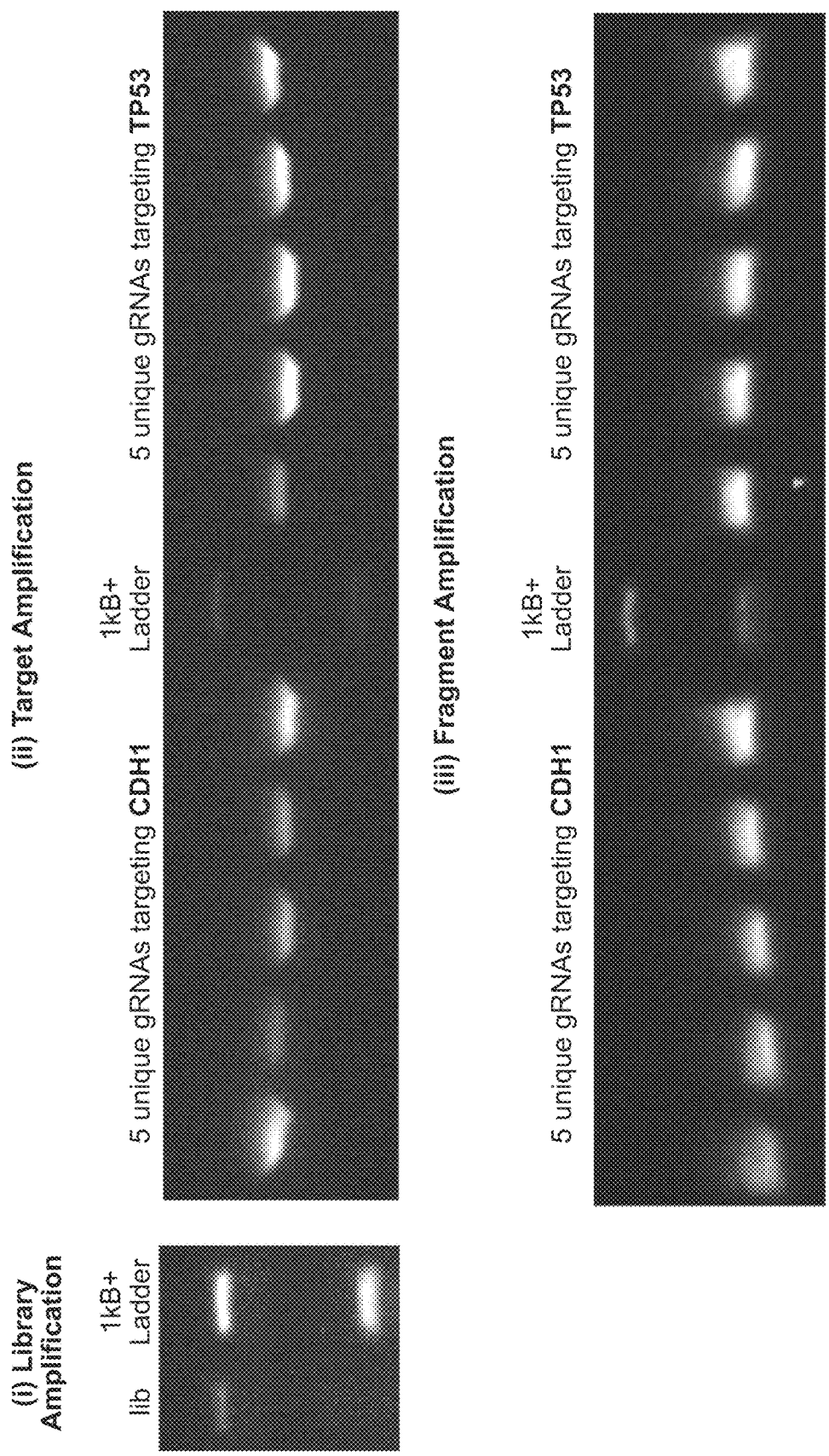
Figure 14B:
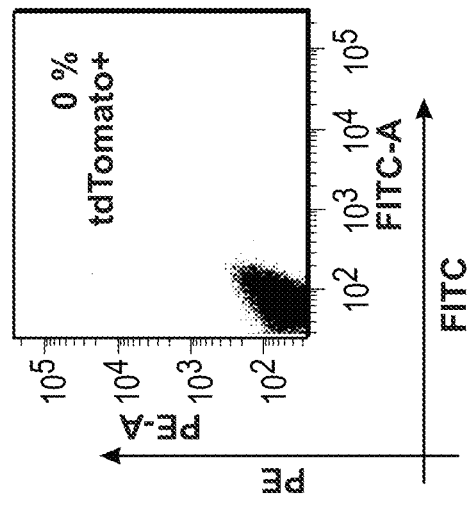
Figure 14D:
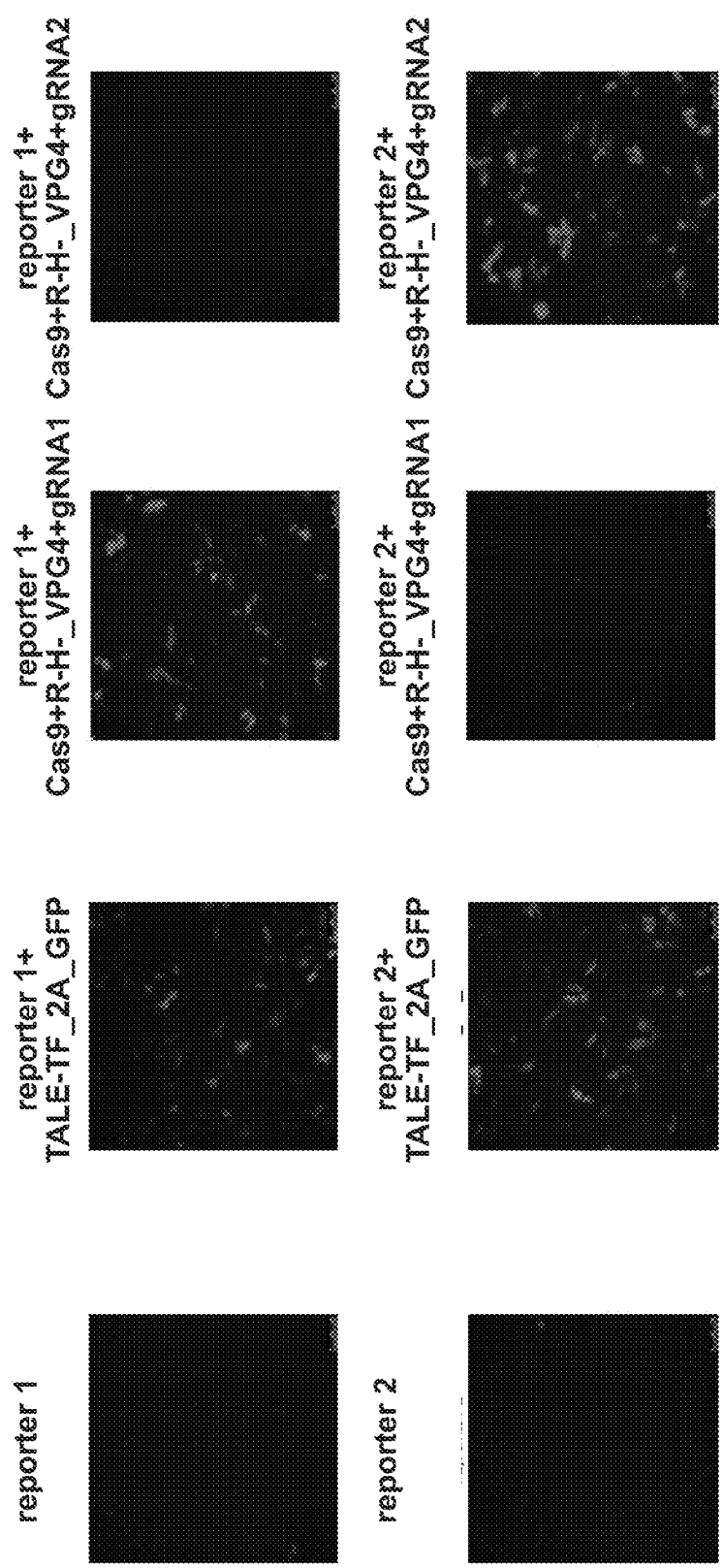

Methodology for Multiplex Synthesis, Retrieval and U6 Expression Vector Cloning of Guide RNAs Targeting Genes in the Human Genome A resource of about 190 k bioinformatically computed unique gRNA sites targeting ~40.5% of all exons of genes in the human genome was generated. As shown in FIG. 13A-1 and FIG. 13A-2, the gRNA target sites were incorporated into a 200 bp format that is compatible for multiplex synthesis on DNA arrays. Specifically, the design allows for (i) targeted retrieval of a specific or pools of gRNA targets from the DNA array oligonucleotide pool (through 3 sequential rounds of nested PCR as indicated in the figure schematic); and (ii) rapid cloning into a common expression vector which upon linearization using an AflII site serves as a recipient for Gibson assembly mediated incorporation of the gRNA insert fragment. As shown in FIG. 13B, the method was used to accomplish targeted retrieval of 10 unique gRNAs from a 12 k oligonucleotide pool synthesized by CustomArray Inc.

Example XVII

CRISPR Mediated RNA-Guided Transcriptional Activation

The CRISPR-Cas system has an adaptive immune defense system in bacteria and functions to 'cleave' invading nucleic acids. According to one aspect, the CRISPR-CAS system is engineered to function in human cells, and to 'cleave' genomic DNA. This is achieved by a short guide RNA directing a Cas9 protein (which has nuclease function) to a target sequence complementary to the spacer in the guide RNA. The ability to 'cleave' DNA enables a host of applications related to genome editing, and also targeted genome regulation. Towards this, the Cas9 protein was mutated to make it nuclease-null by introducing mutations that are predicted to abrogate coupling to Mg2+ (known to be important for the nuclease functions of the RuvC-like and HNH-like domains): specifically, combinations of D10A, D839A, H840A and N863A mutations were introduced. The thus generated Cas9 nuclease-null protein (as confirmed by its ability to not cut DNA by sequencing analysis) and hereafter referred to as Cas9R-H-, was then coupled to a transcriptional activation domain, here VP64, enabling the CRISPR-cas system to function as a RNA guided transcription factor (see FIGS. 14A-D). The Cas9R-H-+VP64 fusion enables RNA-guided transcriptional activation at the two reporters shown. Specifically, both FACS analysis and immunofluorescence imaging demonstrates that the protein enables gRNA sequence specific targeting of the corresponding reporters, and furthermore, the resulting transcription activation as assayed by expression of a dTomato fluorescent protein was at levels similar to those induced by a convention TALE-VP64 fusion protein.

Example XVIII gRNA Sequence Flexibility and Applications Thereof

Figure 15B:
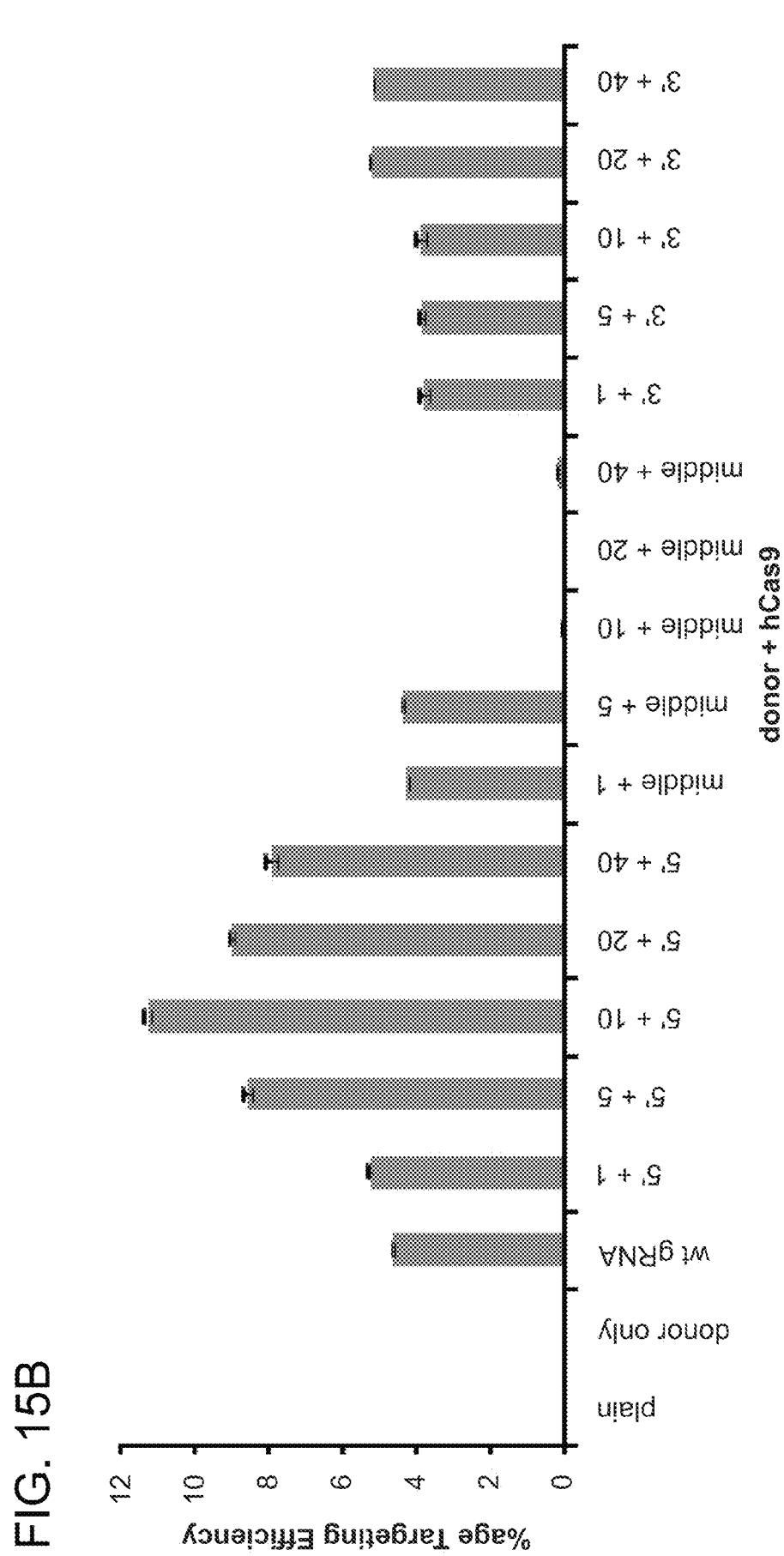

Flexibility of the gRNA scaffold sequence to designer sequence insertions was determined by systematically assaying for a range of the random sequence insertions on the 5', middle and 3' portions of the gRNA: specifically, 1 bp, 5 bp, 10 bp, 20 bp, and 40 bp inserts were made in the gRNA sequence at the 5', middle, and 3' ends of the gRNA (the exact positions of the insertion are highlighted in 'red' in FIG. 15A). This gRNA was then tested for functionality by its ability to induce HR in a GFP reporter assay (as described herein). It is evident that gRNAs are flexible to sequence insertions on the 5' and 3' ends (as measured by retained HR inducing activity). Accordingly, aspects of the present disclosure are directed to tagging of small-molecule responsive RNA aptamers that may trigger onset of gRNA activity, or gRNA visualization. Additionally, aspects of the present disclosure are directed to tethering of ssDNA donors to gRNAs via hybridization, thus enabling coupling of genomic target cutting and immediate physical localization of repair template which can promote homologous recombination rates over error-prone non-homologous end-joining.

The following references identified in the Examples section by number are hereby incorporated by reference in their entireties for all purposes.

REFERENCES

1. K. S. Makarova et al., Evolution and classification of the CRISPR-Cas systems. *Nature reviews. Microbiology* 9, 467 (June, 2011).
2. M. Jinek et al., A programmable dual-RNA-guided DNA endonuclease in adaptive bacterial immunity. *Science* 337, 816 (Aug. 17, 2012).
3. P. Horvath, R. Barrangou, CRISPR/Cas, the immune system of bacteria and archaea. *Science* 327, 167 (Jan. 8, 2010).
4. H. Deveau et al., Phage response to CRISPR-encoded resistance in *Streptococcus thermophilus*. *Journal of bacteriology* 190, 1390 (February, 2008).
5. J. R. van der Ploeg, Analysis of CRISPR in *Streptococcus mutans* suggests frequent occurrence of acquired immunity against infection by M102-like bacteriophages. *Microbiology* 155, 1966 (June, 2009).
6. M. Rho, Y. W. Wu, H. Tang, T. G. Doak, Y. Ye, Diverse CRISPRs evolving in human microbiomes. *PLoS genetics* 8, e1002441 (2012).
7. D. T. Pride et al., Analysis of streptococcal CRISPRs from human saliva reveals substantial sequence diversity within and between subjects over time. *Genome research* 21, 126 (January, 2011).
8. G. Gasiunas, R. Barrangou, P. Horvath, V. Siksnys, Cas9-crRNA ribonucleoprotein complex mediates specific DNA cleavage for adaptive immunity in bacteria. *Proceedings of the National Academy of Sciences of the United States of America* 109, E2579 (Sep. 25, 2012).
9. R. Sapranauskas et al., The *Streptococcus thermophilus* CRISPR/Cas system provides immunity in *Escherichia coli*. *Nucleic acids research* 39, 9275 (November, 2011).
10. J. E. Garneau et al., The CRISPR/Cas bacterial immune system cleaves bacteriophage and plasmid DNA. *Nature* 468, 67 (Nov. 4, 2010).
11. K. M. Esvelt, J. C. Carlson, D. R. Liu, A system for the continuous directed evolution of biomolecules. *Nature* 472, 499 (Apr. 28, 2011).
12. R. Barrangou, P. Horvath, CRISPR: new horizons in phage resistance and strain identification. *Annual review of food science and technology* 3, 143 (2012).
13. B. Wiedenheft, S. H. Sternberg, J. A. Doudna, RNA-guided genetic silencing systems in bacteria and archaea. *Nature* 482, 331 (Feb. 16, 2012).
14. N. E. Sanjana et al., A transcription activator-like effector toolbox for genome engineering. *Nature protocols* 7, 171 (January, 2012).
15. W. J. Kent et al., The human genome browser at UCSC. *Genome Res* 12, 996 (June, 2002).
16. T. R. Dreszer et al., The UCSC Genome Browser database: extensions and updates 2011. *Nucleic Acids Res* 40, D918 (January, 2012).
17. D. Karolchik et al., The UCSC Table Browser data retrieval tool. *Nucleic Acids Res* 32, D493 (Jan. 1, 2004).
18. A. R. Quinlan, I. M. Hall, BEDTools: a flexible suite of utilities for comparing genomic features. *Bioinformatics* 26, 841 (Mar. 15, 2010).
19. B. Langmead, C. Trapnell, M. Pop, S. L. Salzberg, Ultrafast and memory-efficient alignment of short DNA sequences to the human genome. *Genome Biol* 10, R25 (2009).
20. R. Lorenz et al., ViennaRNA Package 2.0. *Algorithms for molecular biology: AMB* 6, 26 (2011).
21. D. H. Mathews, J. Sabina, M. Zuker, D. H. Turner, Expanded sequence dependence of thermodynamic parameters improves prediction of RNA secondary structure. *Journal of molecular biology* 288, 911 (May 21, 1999).
22. R. E. Thurman et al., The accessible chromatin landscape of the human genome. *Nature* 489, 75 (Sep. 6, 2012).
23. S. Kosuri et al., Scalable gene synthesis by selective amplification of DNA pools from high-fidelity microchips. *Nature biotechnology* 28, 1295 (December, 2010).
24. Q. Xu, M. R. Schlabach, G. J. Hannon, S. J. Elledge, Design of 240,000 orthogonal 25mer DNA barcode probes. *Proceedings of the National Academy of Sciences of the United States of America* 106, 2289 (Feb. 17, 2009).

The invention claimed is:

1. An RNA-guided genome editing system for use in a eukaryotic cell comprising
   (1) a guide RNA sequence or a first nucleic acid sequence encoding the guide RNA sequence and
   (2) a Cas enzyme of a Type II CRISPR system that forms a complex with the guide RNA sequence, or a second nucleic acid sequence encoding the Cas enzyme of a Type II CRISPR system,
   wherein the guide RNA sequence comprises a spacer sequence complementary to a target nucleic acid sequence within the eukaryotic cell and a scaffold sequence, and wherein the guide RNA sequence is a crRNA-tracrRNA fusion transcript of between 100 and 250 nucleotides,
   wherein the guide RNA has a secondary structure comprising a first hairpin connected to the spacer sequence and a second 3' hairpin.

2. An ex vivo eukaryotic cell containing the RNA-guided genome editing system of claim 1.

3. The eukaryotic cell of claim 2 wherein the eukaryotic cell is a yeast cell, a plant cell, a mammalian cell or a human cell.

4. The eukaryotic cell of claim 2 wherein the eukaryotic cell is a stem cell.

5. The eukaryotic cell of claim 2 wherein the eukaryotic cell is a human induced pluripotent stem cell.

6. The RNA-guided genome editing system of claim 1 comprising (1) the first nucleic acid sequence encoding the guide RNA sequence and further comprising a regulatory element operable in a eukaryotic cell operably linked to the first nucleic acid sequence encoding the guide RNA sequence.

7. The RNA-guided genome editing system of claim 1 comprising (1) the first nucleic acid sequence encoding the guide RNA sequence and further comprising a human U6 polymerase III promoter operably linked to the first nucleic acid sequence encoding the guide RNA sequence.

8. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid.

9. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a nuclear localization signal.

10. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal nuclear localization signal.

11. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal SV40 nuclear localization signal.

12. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a regulatory element operable in a eukaryotic cell.

13. The RNA-guided genome editing system of claim 1 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a human U6 polymerase III promoter.

14. The RNA-guided genome editing system of claim 1 wherein the Cas enzyme of a Type II CRISPR system is Cas9.

15. The RNA-guided genome editing system of claim 1 wherein the eukaryotic cell is a yeast cell, a plant cell, a mammalian cell or a human cell.

16. The RNA-guided genome editing system of claim 1 wherein the eukaryotic cell is a stem cell.

17. The RNA-guided genome editing system of claim 1 wherein the eukaryotic cell is a human induced pluripotent stem cell.

18. An RNA-guided genome editing system for use in a eukaryotic cell comprising
   (1) a guide RNA sequence or a first nucleic acid sequence encoding the guide RNA sequence and
   (2) a Cas enzyme of a Type II CRISPR system that forms a complex with the guide RNA sequence, or a second nucleic acid sequence encoding the Cas enzyme of a Type II CRISPR system, wherein the guide RNA sequence is a crRNA-tracrRNA fusion transcript comprising a spacer sequence complementary to a target nucleic acid sequence within the eukaryotic cell and a scaffold sequence, and wherein the scaffold sequence comprises GUUUUAGAGCUA-GAAAUAGCAAGUUAAAAUAAGGCUAGU-CCGUUAUCAACUUGA AAAAGUGGCACCGA-GUCGGUGC (SEQ ID NO:46).

19. The RNA-guided genome editing system of claim 18 comprising (1) the first nucleic acid sequence encoding the guide RNA sequence and further comprising a regulatory element operable in a eukaryotic cell operably linked to the first nucleic acid sequence encoding the guide RNA sequence.

20. The RNA-guided genome editing system of claim 18 comprising (1) the first nucleic acid sequence encoding the guide RNA sequence and further comprising a human U6 polymerase III promoter operably linked to the first nucleic acid sequence encoding the guide RNA sequence.

21. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid.

22. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a nuclear localization signal.

23. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal nuclear localization signal.

24. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal SV40 nuclear localization signal.

25. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a regulatory element operable in a eukaryotic cell.

26. The RNA-guided genome editing system of claim 18 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a human U6 polymerase III promoter.

27. The RNA-guided genome editing system of claim 18 wherein the eukaryotic cell is a yeast cell, a plant cell, a mammalian cell or a human cell.

28. The RNA-guided genome editing system of claim 18 wherein the eukaryotic cell is a stem cell.

29. The RNA-guided genome editing system of claim 18 wherein the eukaryotic cell is a human induced pluripotent stem cell.

30. An ex vivo eukaryotic cell containing the RNA-guided genome editing system of claim 18.

31. The eukaryotic cell of claim 30 wherein the eukaryotic cell is a yeast cell, a plant cell, a mammalian cell or a human cell.

32. The eukaryotic cell of claim 30 wherein the eukaryotic cell is a stem cell.

33. The eukaryotic cell of claim 30 wherein the eukaryotic cell is a human induced pluripotent stem cell.

34. The RNA-guided genome editing system of claim 18 wherein the Cas enzyme of a Type II CRISPR system is Cas9.

35. An RNA-guided genome editing system for use in a eukaryotic cell comprising
(1) a guide RNA sequence or a first nucleic acid sequence encoding the guide RNA sequence and
(2) a Cas enzyme of a Type II CRISPR system that forms a complex with the guide RNA sequence, or a second nucleic acid sequence encoding the Cas enzyme of a Type II CRISPR system,
wherein the guide RNA sequence is a crRNA-tracrRNA fusion transcript comprising a spacer sequence complementary to a target nucleic acid sequence within the eukaryotic cell and a scaffold sequence, and wherein the scaffold sequence comprises GUUUUAGAGCUA-GAAAUAGCAAGUUAAAAUAAGGCUAGU-CCGUUAUCAACUUGA AAAAGUGGCACCGA-GUCGGUGCUUUU (SEQ ID NO:45).

36. The RNA-guided genome editing system of claim 35 comprising (1) the first nucleic acid sequence encoding the guide RNA sequence and further comprising a regulatory element operable in a eukaryotic cell operably linked to the first nucleic acid sequence encoding the guide RNA sequence.

37. The RNA-guided genome editing system of claim 35 comprising (1) the first nucleic acid sequence encoding the guide RNA sequence and further comprising a human U6 polymerase III promoter operably linked to the first nucleic acid sequence encoding the guide RNA sequence.

38. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid.

39. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a nuclear localization signal.

40. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal nuclear localization signal.

41. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid and encodes a C-terminal SV40 nuclear localization signal.

42. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a regulatory element operable in a eukaryotic cell.

43. The RNA-guided genome editing system of claim 35 comprising (2) the second nucleic acid sequence encoding the Cas enzyme of a Type II CRISPR system, wherein the second nucleic acid sequence encoding the Cas enzyme of a Type II CRISPR system is a human codon optimized nucleic acid comprising a human U6 polymerase III promoter.

44. The RNA-guided genome editing system of claim 35 wherein the eukaryotic cell is a yeast cell, a plant cell, a mammalian cell or a human cell.

45. The RNA-guided genome editing system of claim 35 wherein the eukaryotic cell is a stem cell.

46. The RNA-guided genome editing system of claim 35 wherein the eukaryotic cell is a human induced pluripotent stem cell.

47. An ex vivo eukaryotic cell containing the RNA-guided genome editing system of claim 35.

48. The eukaryotic cell of claim 47 wherein the eukaryotic cell is a yeast cell, a plant cell, a mammalian cell or a human cell.

49. The eukaryotic cell of claim 47 wherein the eukaryotic cell is a stem cell.

50. The eukaryotic cell of claim 47 wherein the eukaryotic cell is a human induced pluripotent stem cell.

51. The RNA-guided genome editing system of claim 35 wherein the Cas enzyme of a Type II CRISPR system is Cas9.

52. An RNA-guided genome editing system for use in a eukaryotic cell comprising
  (1) a human U6 polymerase III promoter operably linked to a first nucleic acid sequence encoding a guide RNA sequence and
  (2) a Cas enzyme of a Type II CRISPR system that forms a complex with the guide RNA sequence, or a second nucleic acid sequence encoding the Cas enzyme of a Type II CRISPR system,
  wherein the guide RNA sequence comprises a spacer sequence complementary to a target nucleic acid sequence within the eukaryotic cell and a scaffold sequence, and wherein the guide RNA sequence is a crRNA-tracrRNA fusion transcript of between 100 and 250 nucleotides.

53. The RNA-guided genome editing system of claim 52 wherein the Cas enzyme of a Type II CRISPR system is Cas9.

54. An RNA-guided genome editing system for use in a eukaryotic cell comprising
  (1) a guide RNA sequence or a first nucleic acid sequence encoding the guide RNA sequence and
  (2) a human codon optimized nucleic acid sequence encoding a Cas enzyme of a Type II CRISPR system,
  wherein the guide RNA sequence comprises a spacer sequence complementary to a target nucleic acid sequence within the eukaryotic cell and a scaffold sequence, and wherein the guide RNA sequence is a crRNA-tracrRNA fusion transcript of between 100 and 250 nucleotides.

55. The RNA-guided genome editing system of claim 54 wherein the human codon optimized nucleic acid encoding the Cas enzyme of a Type II CRISPR system further encodes a nuclear localization signal.

56. The RNA-guided genome editing system of claim 55 wherein the nuclear localization signal is a C-terminal nuclear localization signal.

57. The RNA-guided genome editing system of claim 55 wherein the C-terminal nuclear localization signal is a C-terminal SV40 nuclear localization signal.

58. The RNA-guided genome editing system of claim 54 wherein the human codon optimized nucleic acid encoding the Cas enzyme comprises a regulatory element operable in a eukaryotic cell.

59. The RNA-guided genome editing system of claim 58 wherein the regulatory element is a human U6 polymerase III promoter.

60. The RNA-guided genome editing system of claim 54 wherein the Cas enzyme of a Type II CRISPR system is Cas9.

61. An RNA-guided genome editing system for use in a eukaryotic cell comprising
  (1) a guide RNA sequence or a first nucleic acid sequence encoding the guide RNA sequence and
  (2) a Cas enzyme of a Type II CRISPR system that forms a complex with the guide RNA sequence, or a second nucleic acid sequence encoding the Cas enzyme of a Type II CRISPR system,
  wherein the guide RNA sequence comprises a spacer sequence complementary to a target nucleic acid sequence within the eukaryotic cell and a scaffold sequence, and wherein the guide RNA sequence is a crRNA-tracrRNA fusion transcript of between 100 and 250 nucleotides,
  wherein the eukaryotic cell is a stem cell.

62. The RNA-guided genome editing system of claim 61 wherein the stem cell is a human induced pluripotent stem cell.

63. The RNA-guided genome editing system of claim 61 wherein the Cas enzyme of a Type II CRISPR system is Cas9.

64. A ex vivo eukaryotic cell containing an RNA-guided genome editing system comprising
  (1) a guide RNA sequence or a first nucleic acid sequence encoding the guide RNA sequence and
  (2) a Cas enzyme of a Type II CRISPR system that forms a complex with the guide RNA sequence, or a second nucleic acid sequence encoding the Cas enzyme of a Type II CRISPR system,
  wherein the guide RNA sequence comprises a spacer sequence complementary to a target nucleic acid sequence within the eukaryotic cell and a scaffold sequence, and wherein the guide RNA sequence is a crRNA-tracrRNA fusion transcript of between 100 and 250 nucleotides,
  wherein the eukaryotic cell is a stem cell.

65. The ex vivo eukaryotic cell of claim 64 wherein the stem cell is a human induced pluripotent stem cell.

66. The ex vivo eukaryotic cell containing an RNA-guided genome editing system of claim 64 wherein the Cas enzyme of a Type II CRISPR system is Cas9.

67. A guide RNA for use in a eukaryotic cell comprising a spacer sequence complementary to a target nucleic acid sequence within the eukaryotic cell and a scaffold sequence, and wherein the scaffold sequence comprises GUUUUA-GAGCUAGAAAUAGCAAGUUAAAAUAAGGCUAGU-CCGUUAUCAACUUGA AAAAGUGGCACCGAGUCG-GUGC (SEQ ID NO:46).

68. A guide RNA for use in a eukaryotic cell comprising a spacer sequence complementary to a target nucleic acid sequence within the eukaryotic cell and a scaffold sequence, and wherein the scaffold sequence comprises GUUUUA-GAGCUAGAAAUAGCAAGUUAAAAUAAGGCUAGU-

CCGUUAUCAACUUGA AAAAGUGGCACCGAGUCGGUGCUUUU (SEQ ID NO:45).

* * * * *

UNITED STATES PATENT AND TRADEMARK OFFICE
CERTIFICATE OF CORRECTION

| | | |
|---|---|---|
| PATENT NO. | : 11,359,211 B2 | Page 1 of 1 |
| APPLICATION NO. | : 16/397423 | |
| DATED | : June 14, 2022 | |
| INVENTOR(S) | : Church et al. | |

It is certified that error appears in the above-identified patent and that said Letters Patent is hereby corrected as shown below:

In the Specification

Column 1, Line 13:
Please delete:
"61/799,169"
And insert:
--61/779,169--

Signed and Sealed this
Seventeenth Day of September, 2024

Katherine Kelly Vidal
*Director of the United States Patent and Trademark Office*

SEQUENCE LISTING

<160> NUMBER OF SEQ ID NOS: 46

<210> SEQ ID NO 1
<211> LENGTH: 268
<212> TYPE: DNA
<213> ORGANISM: Homo sapiens

<400> SEQUENCE: 1
cacttcagga cagcatgttt gctgcctcca gggatcctgt gtcccgagc tgggaccacc    60 ttatattccc agggccggtt aatgtggctc tggttctggg tacttttatc tgtcccctcc   120
accccacagt ggggccacta gggacaggat tggtgacaga aaagcccat cctttaggcct   180 cctccttcct agtctcctga tattgggtct aaccccacc tcctgttagg cagattcctt   240
atctggtgac acaccccat ttcctgga                                       268

<210> SEQ ID NO 2
<211> LENGTH: 53
<212> TYPE: DNA
<213> ORGANISM: Artificial
<220> FEATURE:
<223> OTHER INFORMATION: PCR primer

<400> SEQUENCE: 2
ctcggcattc ctgctgaacc gctcttccga tctacaggag gtgggggtta gac           53

<210> SEQ ID NO 3
<211> LENGTH: 59
<212> TYPE: DNA
<213> ORGANISM: Artificial
<220> FEATURE:
<223> OTHER INFORMATION: PCR primer

<400> SEQUENCE: 3
acactctttc cctacacgac gctcttccga tctcgtgatt atattcccag ggccggtta    59

<210> SEQ ID NO 4
<211> LENGTH: 59
<212> TYPE: DNA
<213> ORGANISM: Artificial
<220> FEATURE:
<223> OTHER INFORMATION: PCR primer

<400> SEQUENCE: 4
acactctttc cctacacgac gctcttccga tctacatcgt atattcccag ggccggtta    59

<210> SEQ ID NO 5
<211> LENGTH: 59
<212> TYPE: DNA
<213> ORGANISM: Artificial
<220> FEATURE:
<223> OTHER INFORMATION: PCR primer

<400> SEQUENCE: 5
acactctttc cctacacgac gctcttccga tctgcctaat atattcccag ggccggtta    59

<210> SEQ ID NO 6
<211> LENGTH: 59
<212> TYPE: DNA
<213> ORGANISM: Artificial
<220> FEATURE:
<223> OTHER INFORMATION: PCR primer

<400> SEQUENCE: 6
acactctttc cctacacgac gctcttccga tcttggtcat atattcccag ggccggtta    59

<210> SEQ ID NO 7
<211> LENGTH: 59
<212> TYPE: DNA
<213> ORGANISM: Artificial
<220> FEATURE:
<223> OTHER INFORMATION: PCR primer

```
<400> SEQUENCE: 7
acactctttc cctacacgac gctcttccga tctcactgtt atattcccag ggccggtta      59

<210> SEQ ID NO 8
<211> LENGTH: 59
<212> TYPE: DNA
<213> ORGANISM: Artificial
<220> FEATURE:
<223> OTHER INFORMATION: PCR primer

<400> SEQUENCE: 8
acactctttc cctacacgac gctcttccga tctattggct atattcccag ggccggtta      59

<210> SEQ ID NO 9
<211> LENGTH: 59
<212> TYPE: DNA
<213> ORGANISM: Artificial
<220> FEATURE:
<223> OTHER INFORMATION: PCR primer

<400> SEQUENCE: 9
acactctttc cctacacgac gctcttccga tctgatctgt atattcccag ggccggtta      59

<210> SEQ ID NO 10
<211> LENGTH: 59
<212> TYPE: DNA
<213> ORGANISM: Artificial
<220> FEATURE:
<223> OTHER INFORMATION: PCR primer

<400> SEQUENCE: 10
acactctttc cctacacgac gctcttccga tcttcaagtt atattcccag ggccggtta      59

<210> SEQ ID NO 11
<211> LENGTH: 59
<212> TYPE: DNA
<213> ORGANISM: Artificial
<220> FEATURE:
<223> OTHER INFORMATION: PCR primer

<400> SEQUENCE: 11
acactctttc cctacacgac gctcttccga tctctgatct atattcccag ggccggtta      59

<210> SEQ ID NO 12
<211> LENGTH: 59
<212> TYPE: DNA
<213> ORGANISM: Artificial
<220> FEATURE:
<223> OTHER INFORMATION: PCR primer

<400> SEQUENCE: 12
acactctttc cctacacgac gctcttccga tctaagctat atattcccag ggccggtta      59

<210> SEQ ID NO 13
<211> LENGTH: 59
<212> TYPE: DNA
<213> ORGANISM: Artificial
<220> FEATURE:
<223> OTHER INFORMATION: PCR primer

<400> SEQUENCE: 13
acactctttc cctacacgac gctcttccga tctgtagcct atattcccag ggccggtta      59
```

```
<210> SEQ ID NO 14
<211> LENGTH: 59
<212> TYPE: DNA
<213> ORGANISM: Artificial
<220> FEATURE:
<223> OTHER INFORMATION: PCR primer

<400> SEQUENCE: 14
acactctttc cctacacgac gctcttccga tcttacaagt atattcccag ggccggtta      59

<210> SEQ ID NO 15
<211> LENGTH: 20
<212> TYPE: DNA
<213> ORGANISM: Artificial
<220> FEATURE:
<223> OTHER INFORMATION: PCR primer

<400> SEQUENCE: 15
ctgccgtctc tctcctgagt                                                 20

<210> SEQ ID NO 16
<211> LENGTH: 20
<212> TYPE: DNA
<213> ORGANISM: Artificial
<220> FEATURE:
<223> OTHER INFORMATION: PCR primer

<400> SEQUENCE: 16
gtgggcttgt actcggtcat                                                 20

<210> SEQ ID NO 17
<211> LENGTH: 80
<212> TYPE: RNA
<213> ORGANISM: Artificial
<220> FEATURE:
<223> OTHER INFORMATION: guide RNA

<400> SEQUENCE: 17
guuuuagagc uagaaauagc aaguuaaaau aaggcuaguc cguuaucaac uugaaaaagu      60
ggcaccgagu cggugcuuuu                                                 80

<210> SEQ ID NO 18
<211> LENGTH: 71
<212> TYPE: DNA
<213> ORGANISM: Homo sapiens

<400> SEQUENCE: 18
taatactttt atcttgtccc ctccacccca cagtggggcc actagggaca ggattggtga     60
cagaaagccc c                                                          71

<210> SEQ ID NO 19
<211> LENGTH: 52
<212> TYPE: DNA
<213> ORGANISM: Homo sapiens

<400> SEQUENCE: 19
ttatctgtcc cctccacccc acagtggggc cactagggaa caggattggt ga             52

<210> SEQ ID NO 20
<211> LENGTH: 22
<212> TYPE: DNA
<213> ORGANISM: Homo sapiens
```

```
<400> SEQUENCE: 20
caggcaggtc ctgctttctc tg                                              22

<210> SEQ ID NO 21
<211> LENGTH: 22
<212> TYPE: DNA
<213> ORGANISM: Homo sapiens

<400> SEQUENCE: 21
cacagtgggg caagcttctg ac                                              22

<210> SEQ ID NO 22
<211> LENGTH: 4146
<212> TYPE: DNA
<213> ORGANISM: Homo sapiens

<400> SEQUENCE: 22
gccaccatgg acaagaagta ctccattggg ctcgatatcg gcacaaacag cgtcggctgg      60
gccgtcatta cggacgagta caaggtgccg agcaaaaaat tcaaagttct gggcaatacc     120
gatcgccaca gcataaagaa gaacctcatt ggcgccctcc tgttcgactc cggggagacg     180
gccgaagcca cgcggctcaa agaacagcca cggcgcagat atacccgcag aaagaatcgg     240
atctgctacc tgcaggagat ctttagtaat gagatggcta aggtggatga ctctttcttc     300
cataggctgg aggagtcctt tttggtggag gaggataaaa gcacgagcg ccacccaatc      360 tttggcaata tcgtggacga ggtggcgtac catgaaaagt acccaaccat atatcatctg     420
aggaagaagc ttgtagacag tactgataag gctgacttgc ggttgatcta tctcgcgctg     480
gcgcatatga tcaaatttcg gggacacttc ctcatcgagg gggacctgaa cccagacaac     540
agcgatgtcg acaaactctt tatccaactg gttcagactt acaatcagct tttcgaagag     600
aacccgatca acgcatccgg agttgacgcc aaagcaatcc tgagcgctag gctgtccaaa     660
tcccggcggc tcgaaaacct catcgcacag ctccctgggg agaagaagaa cggcctgttt     720
ggtaatctta tcgccctgtc actcgggctg accccccaact ttaaatctaa cttcgacctg     780
gccgaagatg ccaagcttca actgagcaaa gacacctacg atgatgatct cgacaatctg     840
ctggcccaga tcggcgacca gtacgcagac ctttttttgg cggcaaagaa cctgtcagac     900
gccattctgc tgagtgatat tctgcgagtg aacacggaga tcaccaaagc tccgctgagc     960
gctagtatga tcaagcgcta tgatgagcac caccaagact tgactttgct gaaggccctt    1020
gtcagacagc aactgcctga aagtacaag gaaattttct tcgatcagtc taaaaatggc    1080
tacgccggat acattgacgg cggagcaagc caggaggaat tttacaaatt tattaagccc    1140
atcttggaaa aaatggacgg caccgaggag ctgctggtaa agcttaacag agaagatctg    1200
ttgcgcaaac agcgcacttt cgacaatgga agcatccccc accagattca cctgggcgaa    1260
ctgcacgcta tcctcaggcg gcaagaggat ttctacccct ttttgaaaga taacagggaa    1320
aagattgaga aaatcctcac atttcggata cctactatg taggcccct cgccgggga      1380 aattccagat cgcgtggat gactcgcaaa tcagaagaga ccatcactcc ctggaacttc    1440
gaggaagtcg tggataaggg ggcctctgcc cagtccttca tcgaaaggat gactaacttt    1500
gataaaaatc tgcctaacga aaaggtgctt cctaaacact ctctgctgta cgagtacttc    1560
acagttttat acgagctcac caaggtcaaa tacgtcacag aagggatgag aaagccagca    1620
ttcctgtctg gagagcagaa gaaagctatc gtggacctcc tcttcaagac gaaccggaaa    1680
gttaccgtga acagctcaa agaagactat ttcaaaaaga ttgaatgttt cgactctgtt    1740
```

```
gaaatcagcg gagtggagga tcgcttcaac gcatccctgg aacgtatca cgatctcctg   1800 aaaatcatta aagacaagga cttcctggac aatgaggaga acgaggacat tcttgaggac   1860
attgtcctca cccttacgtt gtttgaagat agggagatga ttgaagaacg cttgaaaact   1920
tacgctcatc tcttcgacga caaagtcatg aaacagctca agaggcgccg atatacagga   1980
tgggggcggc tgtcaagaaa actgatcaat gggatccgag acaagcagag tggaaagaca   2040
atcctggatt ttcttaagtc cgatggattt gccaaccgga acttcatgca gttgatccat   2100
gatgactctc tcacctttaa ggaggacatc cagaaagcac aagtttctgg ccaggggac    2160 agtcttcacg agcacatcgc taatcttgca ggtagcccag ctatcaaaaa gggaatactg   2220
cagaccgtta aggtcgtgga tgaactcgtc aaagtaatgg aaggcataa gcccgagaat    2280 atcgttatcg agatggcccg agagaaccaa actacccaga agggacagaa gaacagtagg   2340
gaaaggatga agaggattga agagggtata aaagaactgg ggtcccaaat ccttaaggaa   2400
cacccagttg aaaacaccca gcttcagaat gagaagctct acctgtacta cctgcagaac   2460
ggcagggaca tgtacgtgga tcaggaactg acatcaatc ggctctccga ctacgacgtg    2520
gatcatatcg tgccccagtc ttttctcaaa gatgattcta ttgataataa agtgttgaca   2580
agatccgata aaaatagagg gaagagtgat aacgtcccct cagaagaagt tgtcaagaaa   2640
atgaaaaatt attggcggca gctgctgaac gccaaactga tcacacaacg gaagttcgat   2700
aatctgacta aggctgaacg aggtggcctg tctgagttgg ataaagccgg cttcatcaaa   2760
aggcagcttg ttgagacacg ccagatcacc aagcacgtgg cccaaattct cgattcacgc   2820
atgaacacca gtacgatga aaatgacaaa ctgattcgag aggtgaaagt tattactctg     2880
aagtctaagc tggtctcaga tttcagaaag gactttcagt tttataaggt gagagagatc   2940
aacaattacc accatgcgca tgatgcctac ctgaatgcag tggtaggcac tgcacttatc   3000
aaaaaatatc caagcttga atctgaattt gtttacggag actataaagt gtacgatgtt    3060
aggaaaatga tcgcaaagtc tgagcaggaa ataggcaagg ccaccgctaa gtacttcttt   3120
tacagcaata ttatgaattt tttcaagacc gagattacac tggccaatgg agagattcgg   3180
aagcgaccac ttatcgaaac aaacggagaa acaggagaaa tcgtgtggga caagggtagg   3240
gatttcgcga cagtccggaa ggtcctgtcc atgccgcagg tgaacatcgt taaaaagacc   3300
gaagtacaga ccggaggctt ctccaaggaa agtatcctcc cgaaaaggaa cagcgacaag   3360
ctgatcgcac gcaaaaaaga ttgggacccc aagaaatacg gcggattcga ttctcctaca   3420
gtcgcttaca gtgtactggt tgtggccaaa gtggagaaag ggaagtctaa aaaactcaaa   3480
agcgtcaagg aactgctggg catcacaatc atggagcgat caagcttcga aaaaaacccc   3540
atcgactttc tcgaggcgaa aggatataaa gaggtcaaaa aagacctcat cattaagctt   3600
cccaagtact ctctctttga gcttgaaaac ggccggaaac gaatgctcgc tagtgcgggc   3660
gagctgcaga aaggtaacga gctggcactg ccctctaaat acgttaattt cttgtatctg   3720
gccagccact atgaaaagct caaagggtct cccgaagata tgagcagaa gcagctgttc    3780 gtggaacaac acaaacacta ccttgatgag atcatcgagc aaataagcga attctccaaa   3840
agagtgatcc tcgccgacgc taacctcgat aaggtgcttt ctgcttacaa taagcacagg   3900
gataagccca tcagggagca ggcagaaaac attatccact tgtttactct gaccaacttg   3960
ggcgcgcctc agccttcaa gtacttcgac accaccatag acagaaagcg gtacacctct   4020
acaaaggagg tcctggacgc cacactgatt catcagtcaa ttacggggct ctatgaaaca   4080
```

```
agaatcgacc tctctcagct cggtggagac agcagggctg accccaagaa gaagaggaag    4140
gtgtga                                                               4146

<210> SEQ ID NO 23
<211> LENGTH: 455
<212> TYPE: DNA
<213> ORGANISM: Homo sapiens
<220> FEATURE:
<221> NAME/KEY: misc_feature
<222> LOCATION: (320)..(338)
<223> OTHER INFORMATION: n is a, c, g, or t

<400> SEQUENCE: 23
tgtacaaaaa agcaggcttt aaaggaacca attcagtcga ctggatccgg taccaaggtc     60
gggcaggaag agggcctatt tcccatgatt ccttcatatt tgcatatacg atacaaggct    120
gttagagaga taattagaat taatttgact gtaaacacaa agatattagt acaaaatacg    180
tgacgtagaa agtaataatt tcttgggtag tttgcagttt taaaattatg ttttaaaatg    240
gactatcata tgcttaccgt aacttgaaag tatttcgatt tcttggcttt atatatcttg    300
tggaaaggac gaaacaccgn nnnnnnnnnn nnnnnnnngt tttagagcta gaaatagcaa    360
gttaaaataa ggctagtccg ttatcaactt gaaaaagtgg caccgagtcg gtgctttttt    420
tctagaccca gctttcttgt acaaagttgg catta                               455

<210> SEQ ID NO 24
<211> LENGTH: 99
<212> TYPE: RNA
<213> ORGANISM: Artificial
<220> FEATURE:
<223> OTHER INFORMATION: guide RNA
<220> FEATURE:
<221> NAME/KEY: misc_feature
<222> LOCATION: (2)..(20)
<223> OTHER INFORMATION: wherein N is G, A, C or U

<400> SEQUENCE: 24
gnnnnnnnnn nnnnnnnnnn guuuuagagc uagaaauagc aaguuaaaag aaggguagug     60
gguuaucaac uugaaaaagc ggcaccgagu caauacuuu                            99

<210> SEQ ID NO 25
<211> LENGTH: 23
<212> TYPE: DNA
<213> ORGANISM: Homo sapiens

<400> SEQUENCE: 25
gtgaaccgca tcgagctgaa ggg                                             23

<210> SEQ ID NO 26
<211> LENGTH: 23
<212> TYPE: DNA
<213> ORGANISM: Homo sapiens

<400> SEQUENCE: 26
ggagcgcacc atcttcttca agg                                             23

<210> SEQ ID NO 27
<211> LENGTH: 23
<212> TYPE: DNA
<213> ORGANISM: Homo sapiens

<400> SEQUENCE: 27
gtcccctcca ccccacagtg ggg                                             23
```

```
<210> SEQ ID NO 28
<211> LENGTH: 23
<212> TYPE: DNA
<213> ORGANISM: Homo sapiens

<400> SEQUENCE: 28 gggccacta gggacaggat tgg                                              23

<210> SEQ ID NO 29
<211> LENGTH: 23
<212> TYPE: DNA
<213> ORGANISM: Homo sapiens

<400> SEQUENCE: 29
gcatgatgcg cggcccaagg agg                                             23

<210> SEQ ID NO 30
<211> LENGTH: 23
<212> TYPE: DNA
<213> ORGANISM: Homo sapiens

<400> SEQUENCE: 30
gagatgatcg cccttcttc tgg                                              23

<210> SEQ ID NO 31
<211> LENGTH: 23
<212> TYPE: DNA
<213> ORGANISM: Homo sapiens

<400> SEQUENCE: 31
gaattactca cgccccaagg agg                                             23

<210> SEQ ID NO 32
<211> LENGTH: 72
<212> TYPE: DNA
<213> ORGANISM: Homo sapiens

<400> SEQUENCE: 32
taatactttt atcttgtccc ctccacccca cagtggggcc actagggaca ggattggtga     60
cagaaaagcc cc                                                         72

<210> SEQ ID NO 33
<211> LENGTH: 70
<212> TYPE: DNA
<213> ORGANISM: Homo sapiens

<400> SEQUENCE: 33
taatactttt atctgtcaaa aaacccccac agtggggcca ctaggacagg attggtgaca     60
gaaaagcccc                                                            70

<210> SEQ ID NO 34
<211> LENGTH: 71
<212> TYPE: DNA
<213> ORGANISM: Homo sapiens

<400> SEQUENCE: 34
taatactttt atctgtcggg gggaccccac agtggggcca ctagggacag gattggtgac     60
agaaaagccc c                                                          71
```

<210> SEQ ID NO 35
<211> LENGTH: 61
<212> TYPE: DNA
<213> ORGANISM: Homo sapiens

<400> SEQUENCE: 35
taatgcatga tgcgcggccc aaggagggag atgatcgccc cttcttctgg ctctttgaga    60
a                                                                   61

<210> SEQ ID NO 36
<211> LENGTH: 61
<212> TYPE: DNA
<213> ORGANISM: Homo sapiens

<400> SEQUENCE: 36
taatgaatta ctcacgcccc aaggagggtg atgaccggcc gttcttctgg atgtttgaga    60
a                                                                   61

<210> SEQ ID NO 37
<211> LENGTH: 110
<212> TYPE: DNA
<213> ORGANISM: Homo sapiens

<400> SEQUENCE: 37
ggtactttta tctgtcccct ccacccaca gtgggccact cgggacagga ttggtgacag    60
aaaagcccca tccttaggcc tcctccttcc tagtctcctg atattgggtc              110

<210> SEQ ID NO 38
<211> LENGTH: 90
<212> TYPE: DNA
<213> ORGANISM: Homo sapiens

<400> SEQUENCE: 38
ttatctgtcc cctccacccc acagtggggc cactagggac aggaaaggtg acagaaaagc    60
cccatcctta ggcctcctcc ttcctagtct                                    90

<210> SEQ ID NO 39
<211> LENGTH: 23
<212> TYPE: DNA
<213> ORGANISM: Homo sapiens
<220> FEATURE:
<221> NAME/KEY: misc_feature
<222> LOCATION: (2)..(21)
<223> OTHER INFORMATION: wherein N is G, A, T or C

<400> SEQUENCE: 39
gnnnnnnnnn nnnnnnnnnn ngg                                           23

<210> SEQ ID NO 40
<211> LENGTH: 201
<212> TYPE: DNA
<213> ORGANISM: Homo sapiens
<220> FEATURE:
<221> NAME/KEY: misc_feature
<222> LOCATION: (27)..(51)
<223> OTHER INFORMATION: wherein N is G, A, T or C
<220> FEATURE:
<221> NAME/KEY: misc_feature
<222> LOCATION: (93)..(111)
<223> OTHER INFORMATION: wherein N is G, A, T or C
<220> FEATURE:
<221> NAME/KEY: misc_feature
<222> LOCATION: (152)..(176)
<223> OTHER INFORMATION: wherein N is G, A, T or C

```
<400> SEQUENCE: 40
tatgaggacg aatctccccg cttatannnn nnnnnnnnnn nnnnnnnnnn nttcttggct    60
ttatatatct tgtggaaagg acgaaaacac cgnnnnnnnn nnnnnnnnnn ngttttagag   120
ctagaaatag caagttaaaa taaggctagt cnnnnnnnnn nnnnnnnnnn nnnnnngtac   180
aagcacacgt ttgtcaagac c                                            201

<210> SEQ ID NO 41
<211> LENGTH: 415
<212> TYPE: DNA
<213> ORGANISM: Homo sapiens

<400> SEQUENCE: 41 attcgcccctt tgtacaaaaa agcaggcttt aaaggaacca attcagtcga ctggatccgg    60
taccaaggtc gggcaggaag agggcctatt tcccatgatt ccttcatatt tcatatacga   120
tacaaggctg ttagagagat aataagaatt aatttgactg taaacacaaa gatattagta   180
caaaatacgt gacgtagaaa gtaataattt cttgggtagt ttgcagtttt aaaattatgt   240
tttaaaatgg actatcatat gcttaccgta acttgaaagt atttcgattt cttggcttta   300
tatatcttaa gttaaaataa ggctagtccg ttatcaactt gaaaaagtgg caccgagtcg   360
gtgctttttt tctagaccca gctttcttgt acaagttgg cattaaaggg cgaat          415

<210> SEQ ID NO 42
<211> LENGTH: 23
<212> TYPE: DNA
<213> ORGANISM: Artificial
<220> FEATURE:
<223> OTHER INFORMATION: reporter oligonucleotide

<400> SEQUENCE: 42
gtcccctcca ccccacagtg ggg                                           23

<210> SEQ ID NO 43
<211> LENGTH: 23
<212> TYPE: DNA
<213> ORGANISM: Artificial
<220> FEATURE:
<223> OTHER INFORMATION: reporter oligonucleotide

<400> SEQUENCE: 43
ggggccacta gggacaggat tgg                                           23

<210> SEQ ID NO 44
<211> LENGTH: 100
<212> TYPE: DNA
<213> ORGANISM: Artificial
<220> FEATURE:
<223> OTHER INFORMATION: guide RNA

<400> SEQUENCE: 44
ggggccacta gggacaccat guuuuagagc uagaaauagc aaguuaaaau aaggcuaguc    60
cguuaucaac uucaaaaaca cccacccaga cggugcuuuu                         100

<210> SEQ ID NO 45
<211> LENGTH: 80
<212> TYPE: DNA
<213> ORGANISM: Artificial
<220> FEATURE:
<223> OTHER INFORMATION: guide RNA scaffold
```

```
<400> SEQUENCE: 45
guuuuagagc uagaaauagc aaguuaaaau aaggcuaguc cguuaucaac uugaaaaagu      60
ggcaccgagu cggugcuuuu                                                 80

<210> SEQ ID NO 46
<211> LENGTH: 76
<212> TYPE: DNA
<213> ORGANISM: Artificial
<220> FEATURE:
<223> OTHER INFORMATION: guide RNA scaffold

<400> SEQUENCE: 46
guuuuagagc uagaaauagc aaguuaaaau aaggcuaguc cguuaucaac uugaaaaagu      60
ggcaccgagu cggugc                                                     76
```